US011458038B2

(12) United States Patent
Vergara et al.

(10) Patent No.: US 11,458,038 B2
(45) Date of Patent: Oct. 4, 2022

(54) HEAT EXCHANGE MODULE, SYSTEM AND METHOD

(71) Applicants: THE REGENTS OF THE UNIVERSITY OF CALIFORNIA, Oakland, CA (US); HYPOTHERMIA DEVICES, INC., Los Angeles, CA (US)

(72) Inventors: Julio L. Vergara, Los Angeles, CA (US); Daniel M. Estrada, Los Angeles, CA (US); Mayank Kalra, Los Angeles, CA (US); Andrew Padula, Laguna Niguel, CA (US); Daniel E. Cuadra, Los Angeles, CA (US); Ryan C. Cohn, Los Angeles, CA (US)

(73) Assignees: THE REGENTS OF THE UNIVERSITY OF CALIFORNIA, Oakland, CA (US); HYPOTHERMIA DEVICES, INC., Los Angeles, CA (US)

(*) Notice: Subject to any disclaimer, the term of this patent is extended or adjusted under 35 U.S.C. 154(b) by 730 days.

(21) Appl. No.: 16/365,567

(22) Filed: Mar. 26, 2019

(65) Prior Publication Data
US 2019/0262169 A1 Aug. 29, 2019

Related U.S. Application Data

(63) Continuation of application No. PCT/US2017/054196, filed on Sep. 28, 2017.
(Continued)

(51) Int. Cl.
A61F 7/00 (2006.01)
A61F 7/08 (2006.01)
A61F 7/02 (2006.01)

(52) U.S. Cl.
CPC .............. *A61F 7/0053* (2013.01); *A61F 7/08* (2013.01); *A61F 2007/0008* (2013.01);
(Continued)

(58) Field of Classification Search
CPC combination set(s) only.
See application file for complete search history.

(56) References Cited

U.S. PATENT DOCUMENTS 2,991,627 A 7/1961 Suits
3,196,524 A 7/1965 Jamison
(Continued)

FOREIGN PATENT DOCUMENTS

CA 2980764 A1 10/2016
CN 101309657 A 11/2008
(Continued)

OTHER PUBLICATIONS

IPEA/US, United States Patent and Tradmark Office (USPTO), International Preliminary Report on Patentability dated Oct. 21, 2019, related PCT international application No. PCT/US2017/054196, pp. 1-16, claims, pp. 17-45, Article 34 amendment, pp. 46-53.
(Continued)

*Primary Examiner* — Joseph A Stoklosa
*Assistant Examiner* — Adam J Avigan
(74) *Attorney, Agent, or Firm* — O'Banion & Ritchey LLP; John P. O'Banion

(57) ABSTRACT

A heat exchange module having a heat transfer fluid channel and a heat transfer plate in heat transfer relation with fluid in the channel. The reference side of a thermoelectric cooler (TEC) is in thermal contact with the plate. A heat transfer tile is in thermal contact with a user side of the TEC. The module is configured to be operatively positionable with the tile in heat transfer relation with skin of a patient.

11 Claims, 78 Drawing Sheets

Related U.S. Application Data

(60) Provisional application No. 62/400,986, filed on Sep. 28, 2016.

(52) U.S. Cl.
CPC ............... *A61F 2007/0054* (2013.01); *A61F 2007/0056* (2013.01); *A61F 2007/0075* (2013.01); *A61F 2007/0076* (2013.01); *A61F 2007/0096* (2013.01); *A61F 2007/0233* (2013.01); *A61F 2007/0234* (2013.01)

(56) References Cited

U.S. PATENT DOCUMENTS

| | | | |
|---|---|---|---|
| 3,867,939 | A | 2/1975 | Moore |
| 4,470,263 | A | 9/1984 | Lehovec |
| 4,846,176 | A | 7/1989 | Golden |
| 4,860,748 | A | 8/1989 | Chiurco |
| 4,962,761 | A * | 10/1990 | Golden .............. A61F 7/02 165/46 |
| 5,097,829 | A | 3/1992 | Quisenberry |
| 5,174,285 | A | 12/1992 | Fontenot |
| 5,584,183 | A | 12/1996 | Wright |
| 5,603,728 | A | 2/1997 | Pachys |
| 5,653,741 | A | 8/1997 | Grant |
| 5,800,490 | A | 9/1998 | Patz |
| 5,871,526 | A | 2/1999 | Gibbs |
| 5,887,435 | A | 3/1999 | Morton |
| 5,895,418 | A | 4/1999 | Saringer |
| 5,899,077 | A | 5/1999 | Wright |
| 6,019,783 | A | 2/2000 | Philips |
| 6,205,790 | B1 | 3/2001 | Denkin |
| 6,375,674 | B1 | 4/2002 | Carson |
| 6,739,138 | B2 | 5/2004 | Saunders |
| 6,764,502 | B2 | 7/2004 | Bieberich |
| 6,840,955 | B2 | 1/2005 | Ein |
| 7,022,093 | B2 | 4/2006 | Smith |
| 7,077,858 | B2 | 7/2006 | Fletcher |
| 7,637,263 | B2 | 12/2009 | Fisher |
| 7,666,215 | B2 | 2/2010 | Callister |
| 7,959,657 | B1 | 6/2011 | Harsy |
| 8,065,763 | B2 | 11/2011 | Brykalski et al. |
| 8,192,474 | B2 | 6/2012 | Levinson |
| 8,283,602 | B2 | 10/2012 | Augustine |
| 9,078,478 | B2 | 7/2015 | Ross, Jr. |
| 9,132,031 | B2 | 9/2015 | Levinson |
| 9,192,474 | B2 | 11/2015 | Forsell |
| 9,278,023 | B2 | 3/2016 | Dabrowiak |
| 9,421,123 | B2 | 8/2016 | Lee |
| 9,962,284 | B2 | 5/2018 | Robinson |
| 10,292,859 | B2 | 5/2019 | Levinson |
| 11,240,882 | B2 | 2/2022 | Inaba |
| 2002/0026226 | A1 | 2/2002 | Ein |
| 2002/0120317 | A1 | 8/2002 | Fletcher |
| 2002/0156509 | A1 | 10/2002 | Cheung |
| 2002/0161419 | A1 | 10/2002 | Carson |
| 2003/0097845 | A1 | 5/2003 | Saunders |
| 2004/0158303 | A1 | 8/2004 | Lennox |
| 2004/0159109 | A1 | 8/2004 | Harvie |
| 2005/0065581 | A1 | 3/2005 | Fletcher |
| 2005/0143797 | A1 | 6/2005 | Parish |
| 2006/0280948 | A1 | 12/2006 | Moreshead |
| 2006/0293732 | A1 | 12/2006 | Collins |
| 2008/0046047 | A1 | 2/2008 | Jacobs |
| 2008/0077201 | A1 * | 3/2008 | Levinson ............ A61B 5/6843 607/96 |
| 2008/0077211 | A1 * | 3/2008 | Levinson ............ A61F 7/0085 607/108 |
| 2008/0097560 | A1 | 4/2008 | Radziunas |
| 2008/0097562 | A1 | 4/2008 | Tan |
| 2008/0188915 | A1 | 8/2008 | Mills |
| 2008/0249524 | A1 | 10/2008 | Dunning |
| 2008/0287839 | A1 | 11/2008 | Rosen |
| 2009/0000309 | A1 | 1/2009 | Hershberger |
| 2009/0155838 | A1 | 6/2009 | Hale |
| 2009/0264969 | A1 | 10/2009 | Gammons |
| 2009/0312822 | A1 | 12/2009 | Besner |
| 2010/0132930 | A1 | 6/2010 | Izenson |
| 2010/0198322 | A1 | 8/2010 | Joseph |
| 2010/0280581 | A1 | 11/2010 | Cushman |
| 2011/0030754 | A1 | 2/2011 | Smythe |
| 2011/0071603 | A1 | 3/2011 | Moore |
| 2011/0238050 | A1 | 9/2011 | Allison |
| 2012/0118344 | A1 | 5/2012 | Schluck |
| 2012/0239123 | A1 | 9/2012 | Weber |
| 2013/0012388 | A1 | 1/2013 | Song |
| 2013/0013033 | A1 | 1/2013 | Lowe |
| 2013/0085552 | A1 | 4/2013 | Mandel |
| 2013/0172829 | A1 | 7/2013 | Badawi |
| 2014/0222121 | A1 | 8/2014 | Spence |
| 2014/0228918 | A1 | 8/2014 | Brienza |
| 2014/0276257 | A1 | 9/2014 | Santa Maria |
| 2014/0311543 | A1 | 10/2014 | Takahiro |
| 2014/0326287 | A1 | 11/2014 | Wiant |
| 2014/0352325 | A1 | 12/2014 | Brown |
| 2015/0080989 | A1 | 3/2015 | Mohn |
| 2015/0223971 | A1 | 8/2015 | Zaveri |
| 2015/0238349 | A1 | 8/2015 | Giuliani |
| 2015/0366703 | A1 | 12/2015 | Du |
| 2016/0035957 | A1 | 2/2016 | Casey |
| 2016/0178251 | A1 | 6/2016 | Johnson |
| 2016/0270952 | A1 | 9/2016 | Vergara |
| 2017/0027053 | A1 | 1/2017 | Moczygemba |
| 2018/0098903 | A1 | 4/2018 | Vergara |
| 2018/0204993 | A1 | 7/2018 | Himmer |
| 2019/0099287 | A1 | 4/2019 | Vergara |
| 2019/0099288 | A1 | 4/2019 | Vergara |

FOREIGN PATENT DOCUMENTS

| | | |
|---|---|---|
| CN | 103142217 A | 6/2013 |
| CN | 203341808 U | 12/2013 |
| DE | 4238291 A1 | 5/1994 |
| DE | 202006020386 U1 | 7/2008 |
| EP | 3278047 A1 | 2/2018 |
| JP | H04077915 | 7/1992 |
| JP | H04077915 Y | 7/1992 |
| JP | 2003323219 | 11/2003 |
| JP | 2006230761 | 9/2006 |
| JP | 2006230761 A | 9/2006 |
| JP | 2008546510 A | 12/2008 |
| JP | 2009501067 A | 1/2009 |
| JP | 2010515481 | 5/2010 |
| JP | 2011067638 | 4/2011 |
| KR | 1020080060193 | 1/2008 |
| KR | 1020140140617 | 12/2014 |
| KR | 20150083559 A | 7/2015 |
| SU | 1179987 A1 | 9/1985 |
| TW | 201110282 A | 3/2011 |
| WO | 0195841 A2 | 12/2001 |
| WO | 0195841 A3 | 12/2001 |
| WO | 02064069 A2 | 8/2002 |
| WO | 2002064069 A2 | 8/2002 |
| WO | 2004111741 A1 | 12/2004 |
| WO | 2007005073 A2 | 1/2007 |
| WO | 2008039556 A1 | 4/2008 |
| WO | 2008039557 | 4/2008 |
| WO | 2008039557 A1 | 4/2008 |
| WO | 2008085162 A1 | 7/2008 |
| WO | 2011156643 A1 | 12/2011 |
| WO | 2013124866 A2 | 8/2013 |
| WO | 2013144008 A1 | 10/2013 |
| WO | 2014001789 A1 | 1/2014 |
| WO | 2014057450 A1 | 4/2014 |
| WO | 2015048170 | 4/2015 |
| WO | 2015048170 A | 4/2015 |
| WO | 2015048170 A1 | 4/2015 |
| WO | 2016160691 | 10/2016 |
| WO | 2016160691 A1 | 10/2016 |
| WO | 2017171719 | 10/2017 |
| WO | 2017171719 A1 | 10/2017 |
| WO | 2017172836 | 10/2017 |

(56) References Cited

FOREIGN PATENT DOCUMENTS

| WO | 2018064220 | A1 | 4/2018 |
|---|---|---|---|
| WO | 2018064428 | | 4/2018 |
| WO | 2018064428 | A1 | 4/2018 |

OTHER PUBLICATIONS

European Patent Office (EPO), Communication (extended European search report) dated Sep. 25, 2019, related European patent application No. EP 16897277.6, pp. 1-9, claims searched, pp. 10-12.
European Patent Office (EPO), Communication (extended European search report) dated Oct. 22, 2019, related European patent application No. EP 17776506.2, pp. 1-12, claims searched, pp. 13-15.
European Patent Office (EPO), Communication (extended European search report) dated Apr. 8, 2020, related European patent application No. EP 17857465.3, pp. 1-8, claims searched, pp. 9-11.
Intellectual Property India, Examination Report dated Jan. 24, 2020, related India patent application No. 201647009683, pp. 1-6, claims examined, pp. 7-10.
Japan Patent Office (JPO), official action dated Apr. 21, 2020, related Japanese patent application No. 2016-517424, pp. 1-4, English-language translation pp. 5-8, claims examined pp. 9-12.
State Intellectual Property Office of the People's Republic of China, The Second Office Action dated Mar. 26, 2020, related Chinese patent application No. 201680019132.6, pp. 1-9, English-language translation, pp. 10-24, claims examined, pp. 25-32.
Japan Patent Office (JPO), official action dated Mar. 10, 2020, related Japanese patent application No. 2017-549684, pp. 1-5, English-language translation , pp. 6-10, claims examined, pp. 11-16.
Korean Intellectual Property Office (KIPO), official action dated Mar. 9, 2020, related Korean patent application No. 10-2017-7030302, pp. 1-7, English-language translation, pp. 8-10, claims examined, pp. 11-16.
Japan Patent Office (JPO), official action dated Mar. 17, 2020, related Japanese patent application No. 2018-550772, pp. 1-7, English-language translation, pp. 8-15, claims examined, pp. 16-19.
Japan Patent Office (JPO), official action dated Aug. 31, 2021, related Japanese patent application No. 2019-516508, pp. 1-6, English-language translation, pp. 7-12, claims examined, pp. 13-20.
IPEA/US, United States Patent and Trademark Office, International Preliminary Report on Patentability dated Mar. 8, 2019, related PCT international application No. PCT/US2017/024628, pp. 1-9, claims examined, pp. 10-34.
National Intellectual Property Administration, PRC (CNIPA), The First Office Action dated Jul. 3, 2019, related China Patent Application No. 201680019132.6, Chinese-language document pp. 1-9, English-language translation p. 10-21, claims examined pp. 22-27.
Japan Patent Office (JPO), official action dated Jun. 16, 2020, related Japanese patent application No. 2019-074530, pp. 1-7, English-language translation (partial), pp. 8-12, claims examined, pp. 13-17.
Korean Intellectual Property Office (KIPO), official action dated Jun. 4, 2020, related Korean patent application No. 10-2018-7028057, pp. 1-4, English-language translation, pp. 5-7, claims examined, pp. 8-11.
State Intellectual Property Office of the People's Republic of China, The First Office Action dated Jul. 29, 2020, related Chinese patent application No. 201780020778.0, pp. 1-14, English-language translation, pp. 15-33, claims examined, pp. 34-58.
IP Australia, Examination report No. 1 for standard patent application dated Aug. 26, 2020, related Australian patent application No. 2016243565, pp. 1-5, claims examined, pp. 6-11.
European Patent Office (EPO), Communication pursuant to Article 94(3) EPC dated Jun. 1, 2021, related European patent application No. 14 849 500.5, pp. 1-6, claims examined, pp. 7-10.
Korean Intellectual Property Office, Notice of Preliminary Rejection dated Jul. 16, 2021, related Korean patent application No. 10-2018-7028696, pp. 1-7, English-language translation, pp. 8-11, claims examined, pp. 12-24.

European Patent Office (EPO), extended European search report dated Mar. 29, 2017, related European patent application No. 14849500.5, pp. 1-8, with claims searched, pp. 9-11.
IP Australia, Patent Examination Report 1 dated May 24, 2018, related Australian patent application No. 2014326780, pp. 1-4, with claims examined, pp. 5-7.
IPEA/US, United States Patent and Trademark Office (USPTO), International Preliminary Report on Patentability dated Sep. 10, 2018, related PCT international application No. PCT/US2016/024592, pp. 1-12, claims, pp. 13-20, drawings, pp. 21-46, Article 34 amendment, pp. 47-56.
ISA/US, United States Patent and Trademark Office (USPTO), International Search Report and Written Opinion dated Aug. 28, 2017, related PCT international application No. PCT/US2017/024628, pp. 1-23, with claims searched, pp. 24-46.
ISA/US, United States Patent and Trademark Office (USPTO), International Search Report and Written Opinion dated Feb. 6, 2018, related PCT international application No. PCT/US2017/054196, pp. 1-18, with claims searched, pp. 19-32.
ISA/US, United States Patent and Trademark Office (USPTO), International Search Report and Written Opinion dated Jul. 1, 2016, related PCT international application No. PCT/US2016/024501, pp. 1-19, with claims searched, pp. 20-25.
ISA/US, United States Patent and Trademark Office (USPTO), International Search Report and Written Opinion dated Mar. 8, 2018, related PCT international application No. PCT/US2017/053812, pp. 1-16, with claims searched, pp. 17-35.
ISA/US, United States Patent and Trademark Office (USPTO), International Search Report and Written Opinion dated Sep. 14, 2016, related PCT international application No. PCT/US2016/024592, pp. 1-13, with claims searched, pp. 14-17.
Japan Patent Office (JPO), official action dated Jul. 31, 2018, related Japanese patent application No. 2016-517424, Japanese-language document pp. 1-6, English-language translation pp. 7-12, claims examined pp. 13-16.
Korean Intellectual Property Office (KIPO), International Search Report and Written Opinion, counterpart PCT international patent application No. PCT/US2014/057276, dated Jan. 8, 2015, pp. 1-17, with claims searched, pp. 18-21.
IP Australia, Examination report No. 2 dated Dec. 6, 2018, related Australian patent application No. 2014326780, pp. 1-7, claims examined, pp. 8-11.
Japan Patent Office (JPO), Decision of Refusal dated Dec. 11, 2018, related Japanese patent application No. 2016-517424, Japanese-language document pp. 1-6, English-language translation pp. 7-11, claims examined pp. 12-15.
European Patent Office (EPO), Communication (Extended European Search Report) dated Oct. 18, 2018, related European patent application No. 16773916.8, pp. 1-9, claims searched, pp. 10-12.
European Patent Office (EPO), Communication pursuant to Article 94(3) EPC dated Dec. 12, 2020, repated European patent application No. EP 16773916.8, pp. 1-8, claims examined, p. 9-10.
Canadian Intellectual Property Office, office action dated Dec. 29, 2020, related Canadian patent application No. 2,925,094, pp. 1-8, claims examined, pp. 9-12.
Japan Patent Office, official action dated Jan. 5, 2021, related Japanese patent application No. 2017-549684, pp. 1-4, English-language translation, pp. 5-7, claims examined, pp. 8-12.
P Australia, Examination report No. 2 for standard patent application dated Aug. 26, 2020, related Australian patent application No. 2016243565, pp. 1-6, claims examined, pp. 7-11.
Korean Intellectual Property Office, official action dated Jan. 11, 2021, prepared Korean patent application No. 10-2016-7007807, pp. 1-11, English-language translation, pp. 12-14, claimls examined, pp. 15-18.
The Patent Office of the People's Repubic of China, official action dated Jan. 12, 2021, related Chinese patent application No. 2017800664983, pp. 1-6, Englis-language translation, pp. 7-15, claims examined, pp. 16-29.
State Intellectual Property Office of the People's Republic of China, The Third Office Action dated Feb. 28, 2022, related Chinese patent application No. 201780066498.3, pp. 1-3, English-language translation, pp. 4-8, claims examined, pp. 5-13.

(56) References Cited

OTHER PUBLICATIONS

Japan Patent Office (JPO), official action dated Dec. 20, 2021, related Japanese patent application No. 2018-551821, pp. 1-3, English-language translation pp. 4-6, claims examined, pp. 7-35.

State of Israel Ministry of Justice the Patent Authority, Notification No. 26, issued Dec. 1, 2021, related Israel patent application No. 265686, pp. 1-4, English-language translation, pp. 5-8, claims examined, pp. 9-19.

The Patent Office of the People's Repubic of China, official action dated Jan. 6, 2022, related Chinese patent application No. 201680084088.7, pp. 1-10, English-language machine translation, pp. 11-19, claims examined, pp. 20-23.

Korean Intellectual Property Office, official action dated Feb. 16, 2022, related Korean patent application No. 10-2019-7009157, pp. 1-7, English-language translation, pp. 8-11, claims examined, pp. 12-25.

IP Australia, Examination report No. 1 for standard patent application dated Feb. 21, 2022, related Australian patent application No. 2017335975, pp. 1-5, claims examined, pp. 6-19.

Japan Patent Office (JPO), official action issued May 10, 2022, related Japanese patent application No. 2019-516508, pp. 1-3, English-language translation, pp. 4-6, claims examined, pp. 7-13.

Canadian Intellectual Property Office, office action dated May 27, 2022, related Canadian patent application No. 2,980,764, pp. 1-3, claims examined, pp. 4-9.

* cited by examiner

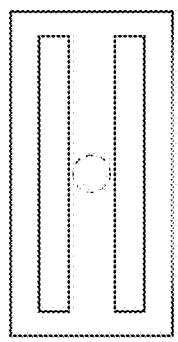
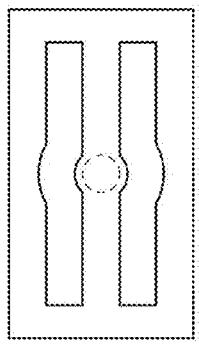
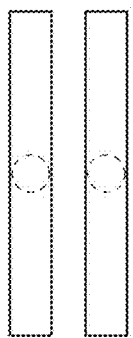
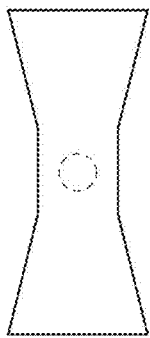

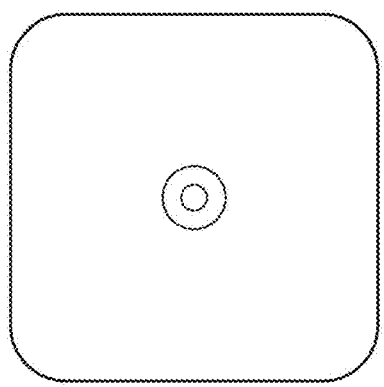
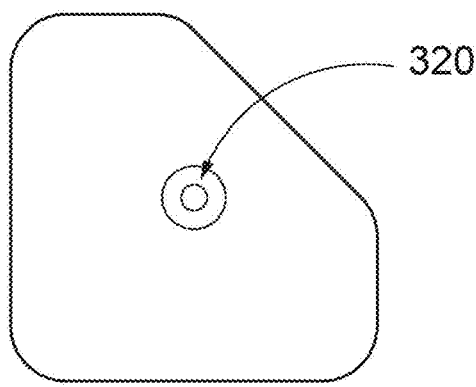
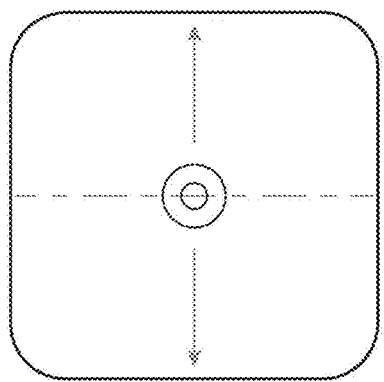
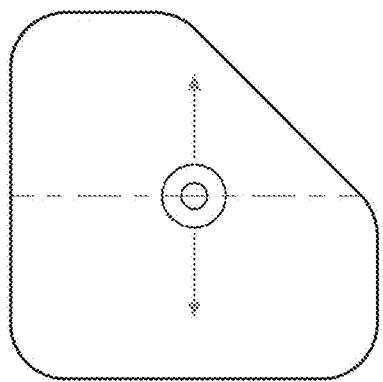
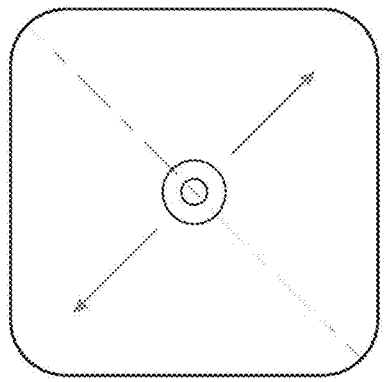
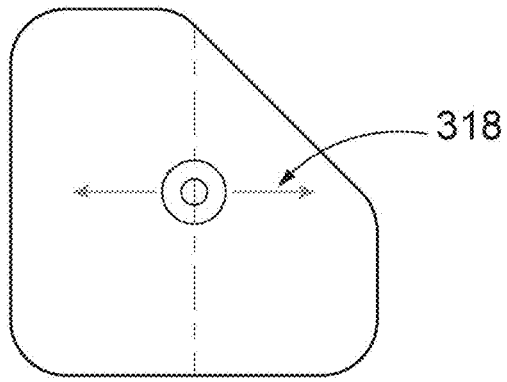
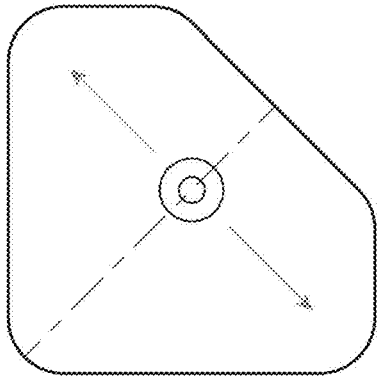
FIG. 59

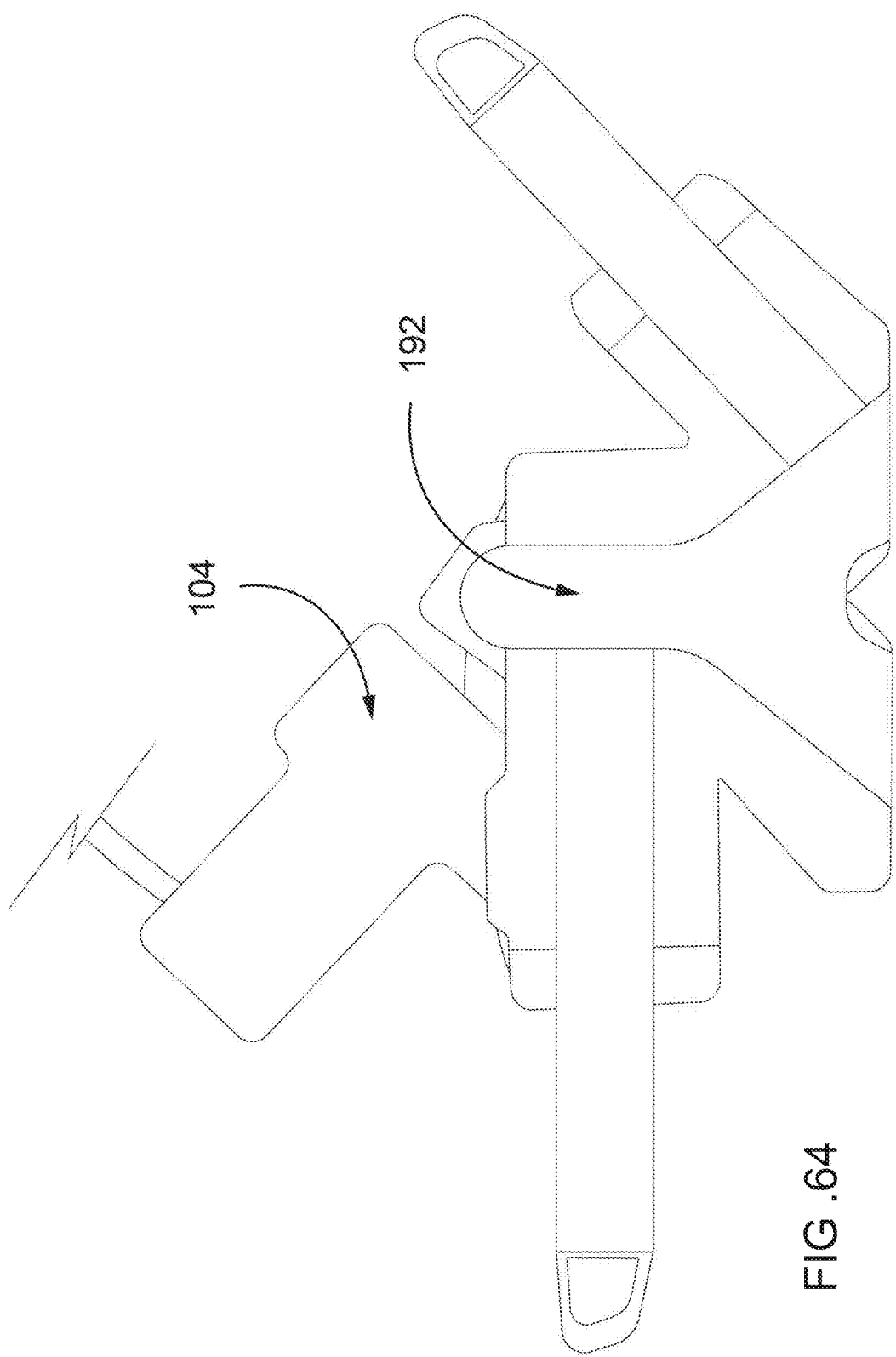

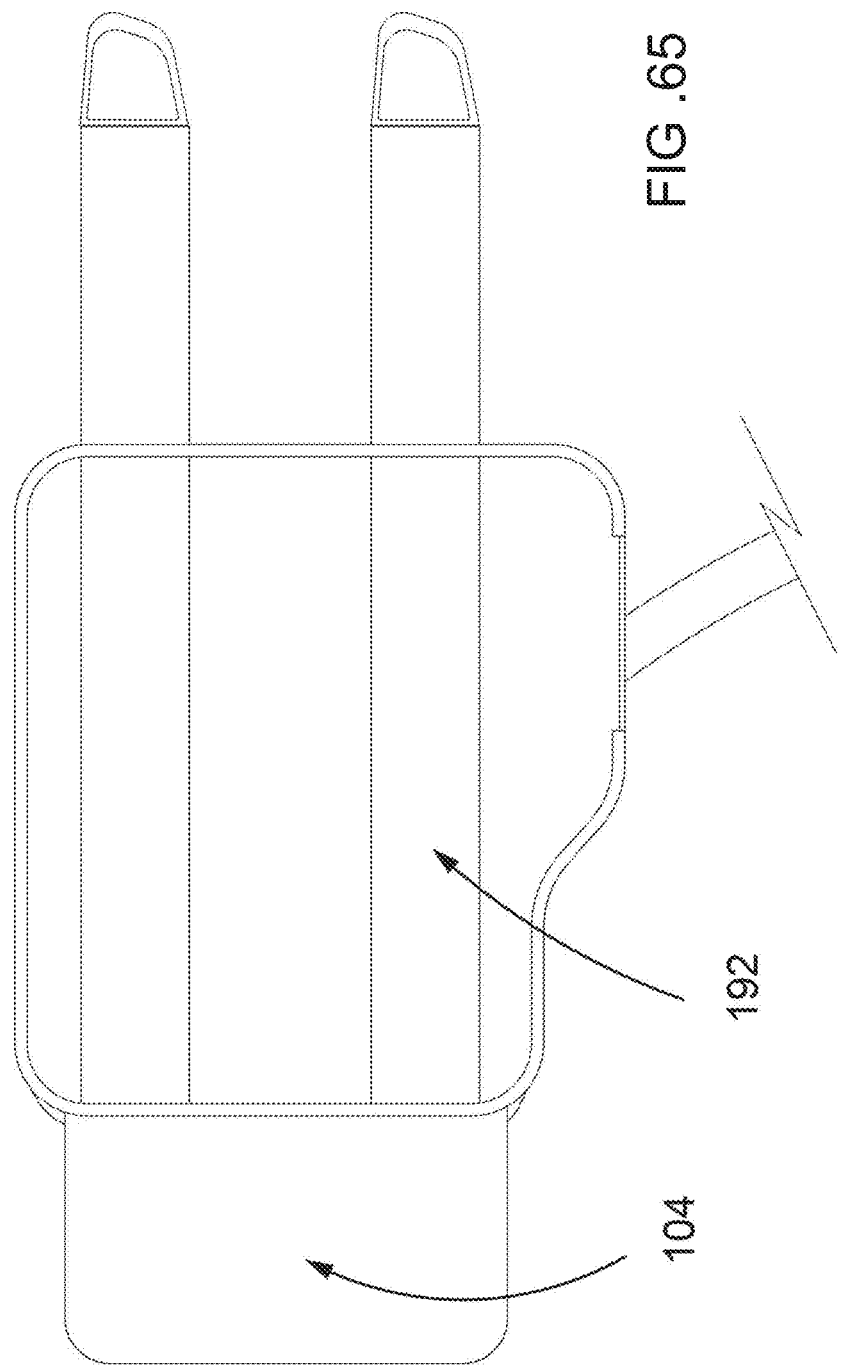

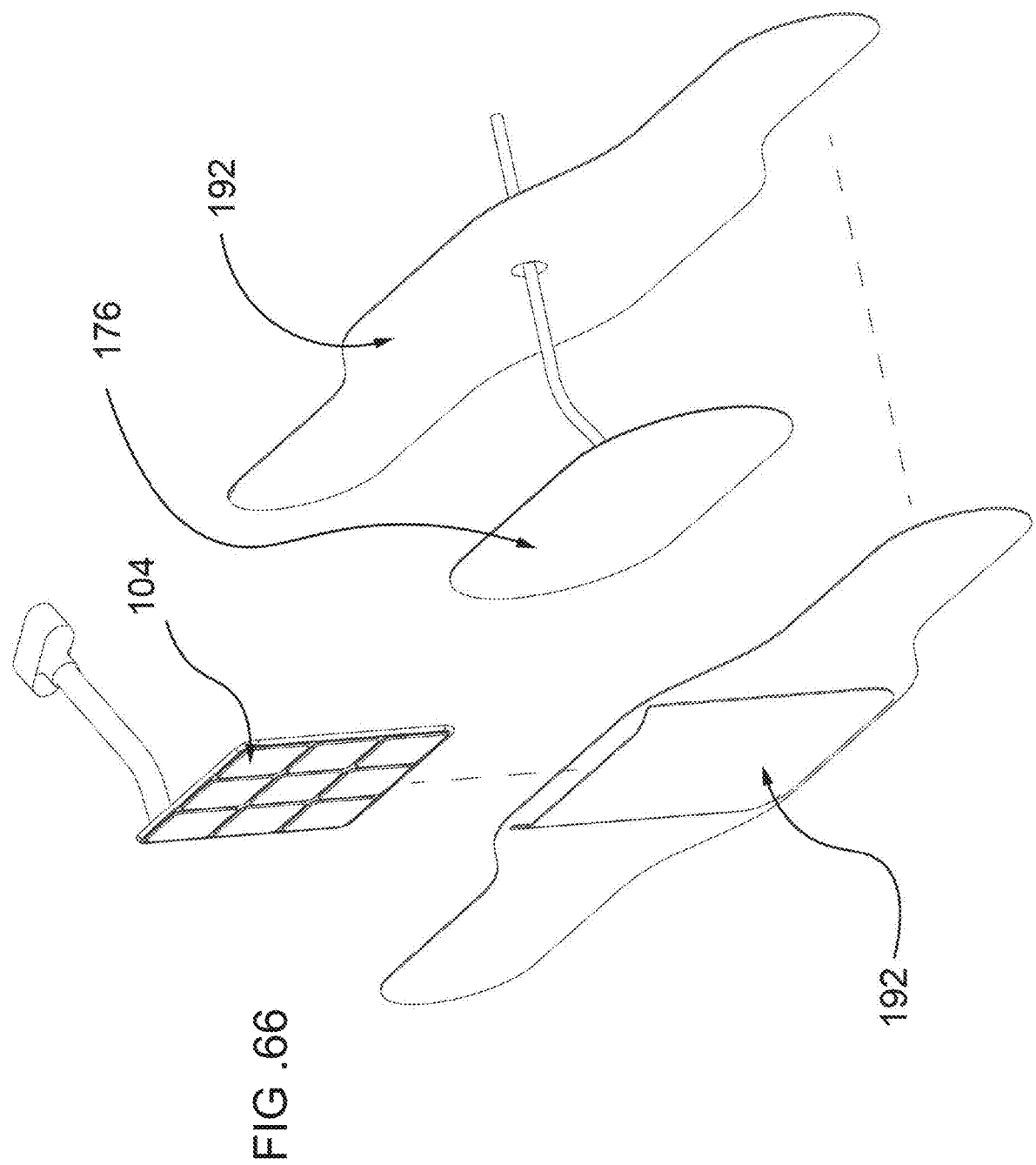

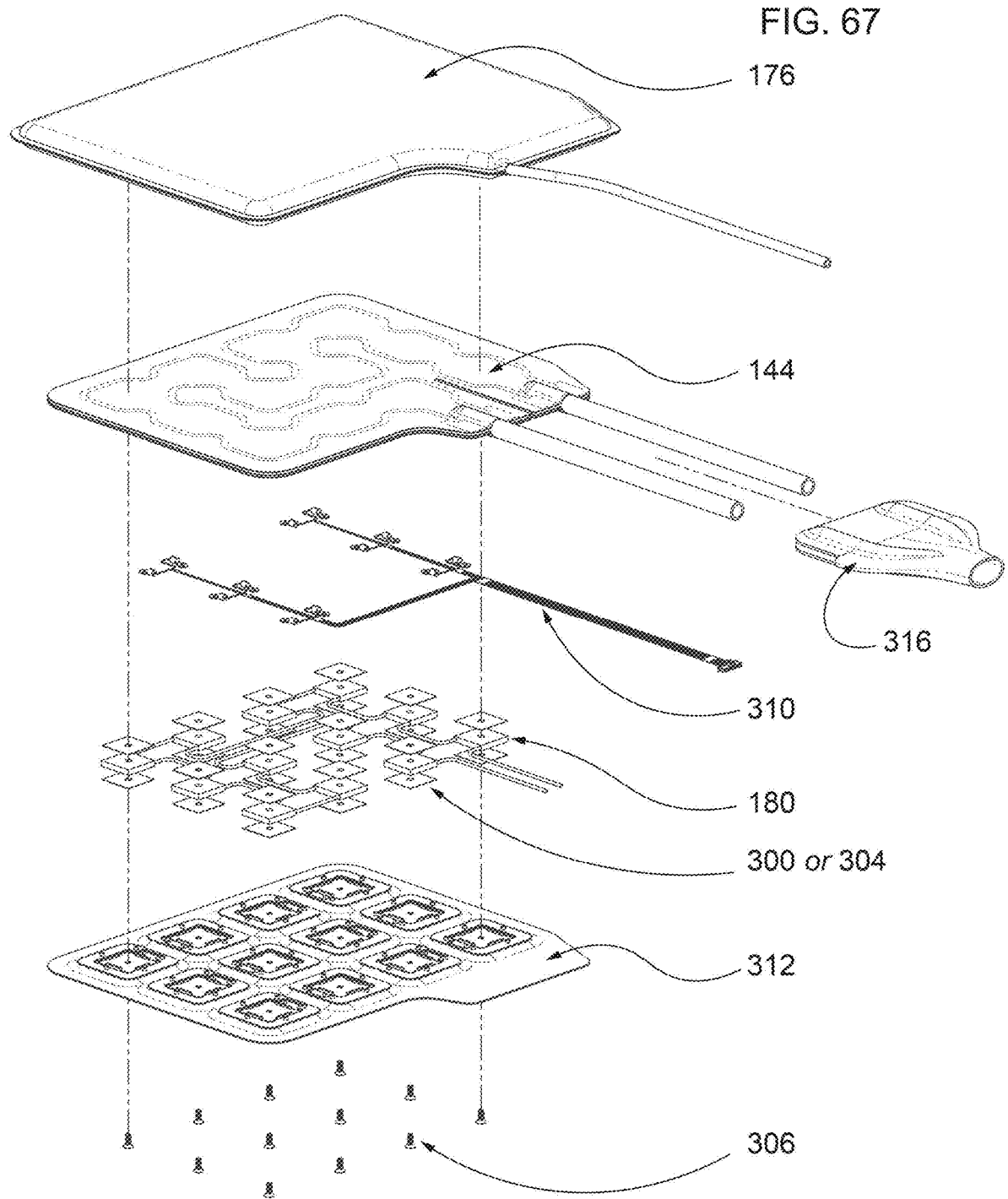

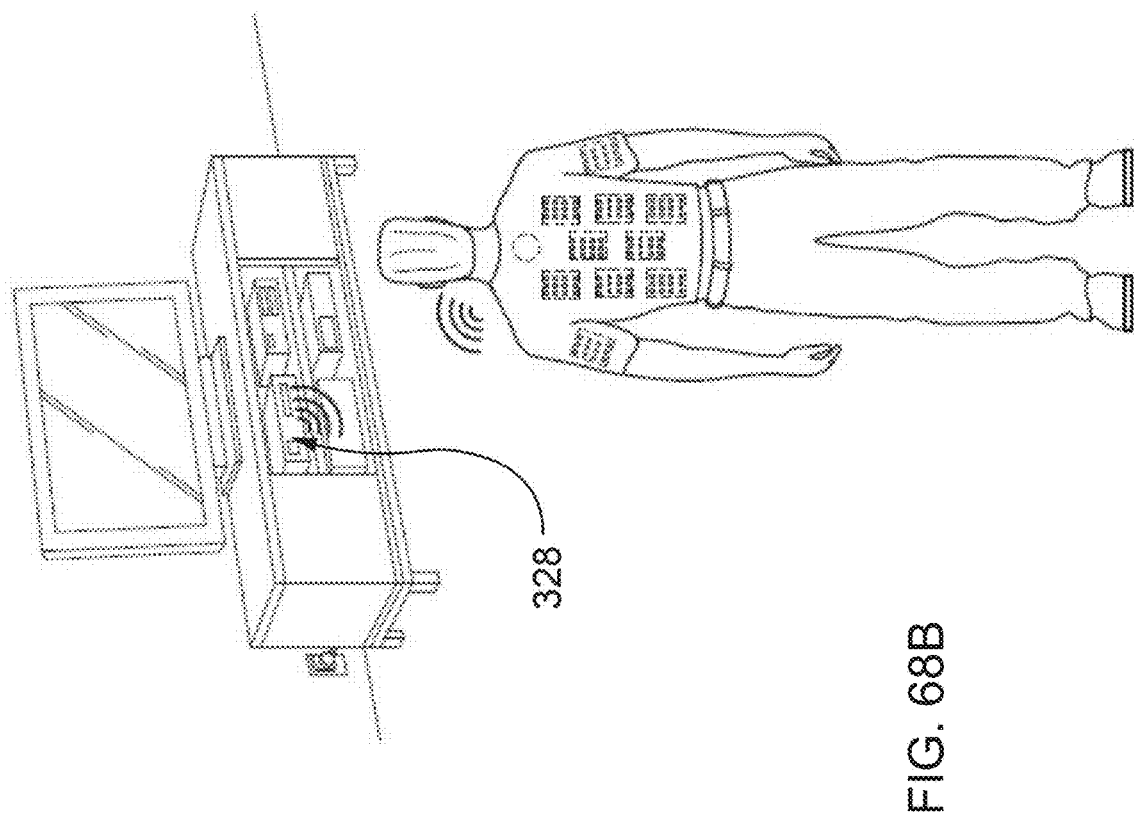
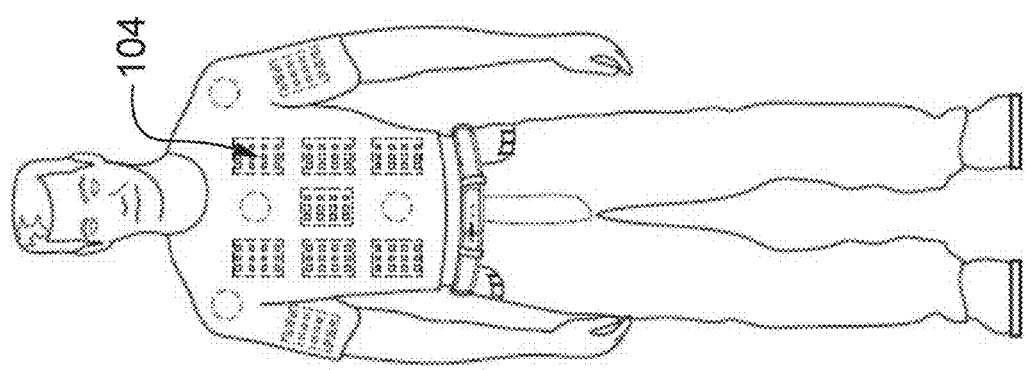
FIG. 68B

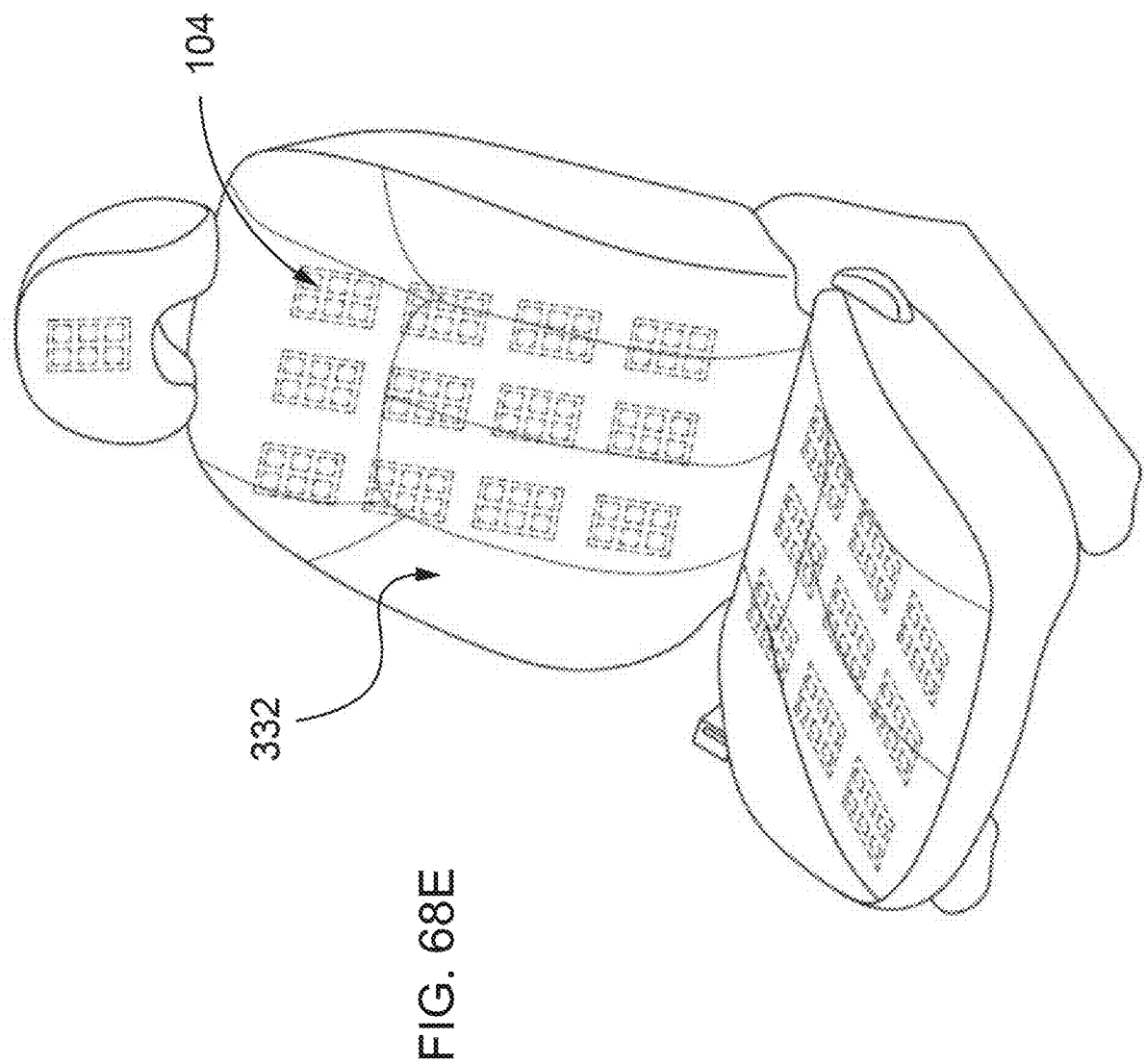

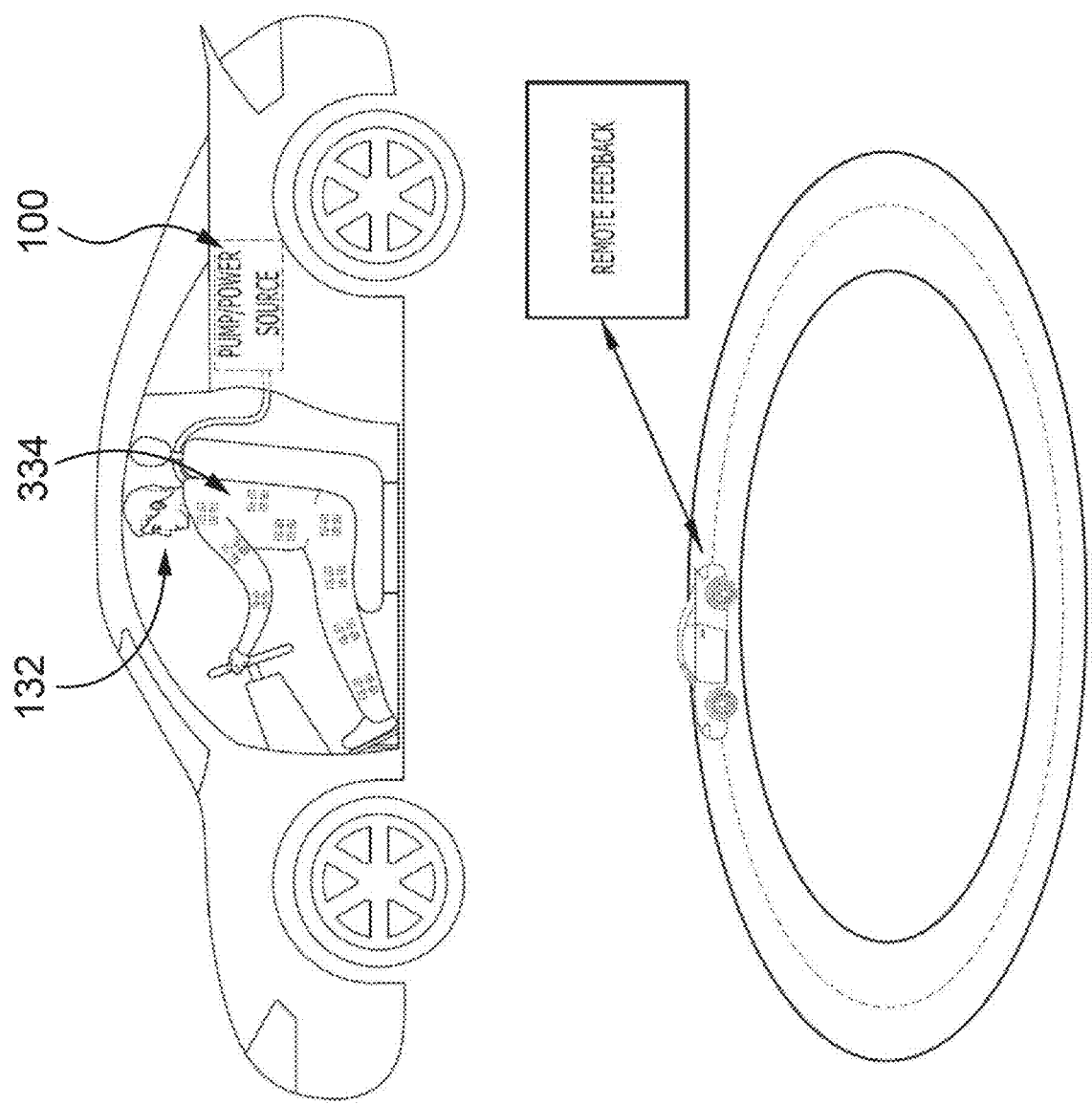

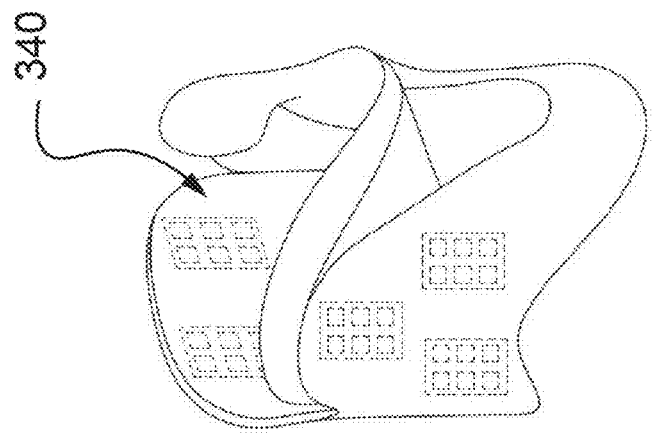
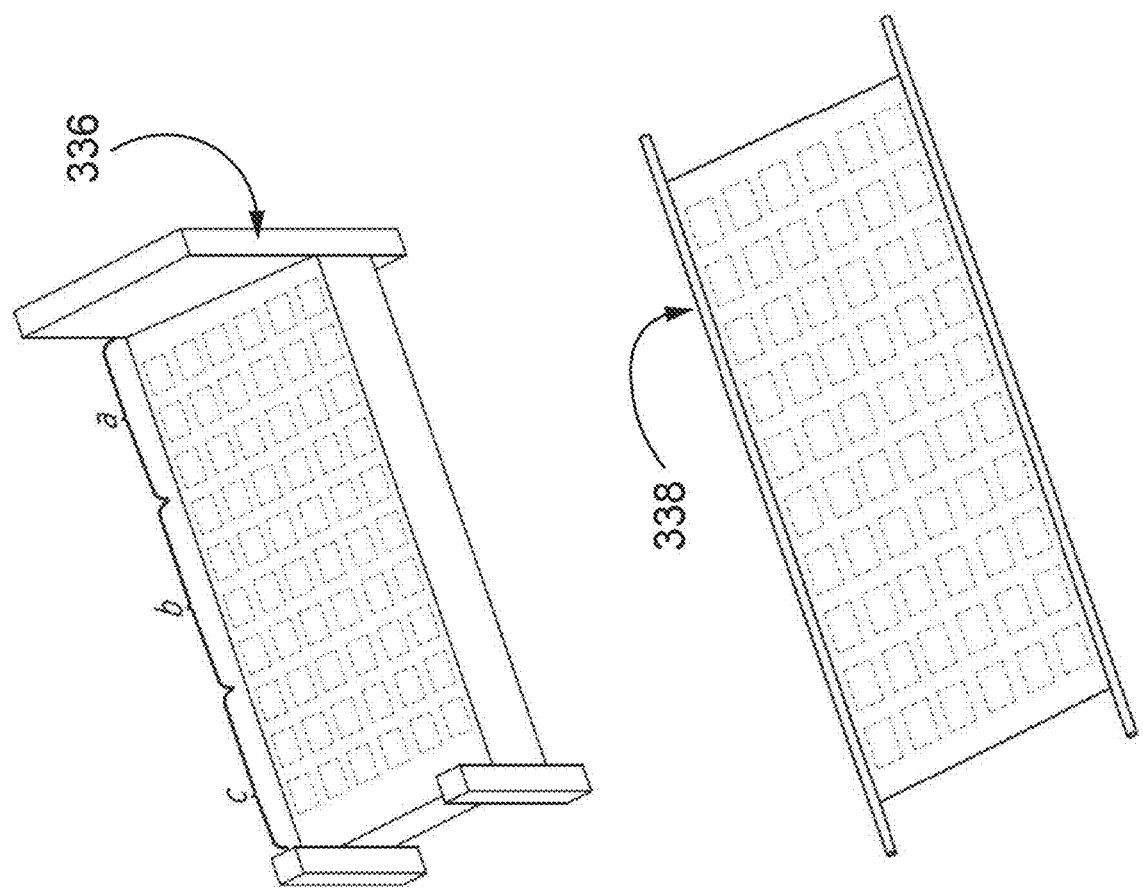
FIG. 68G

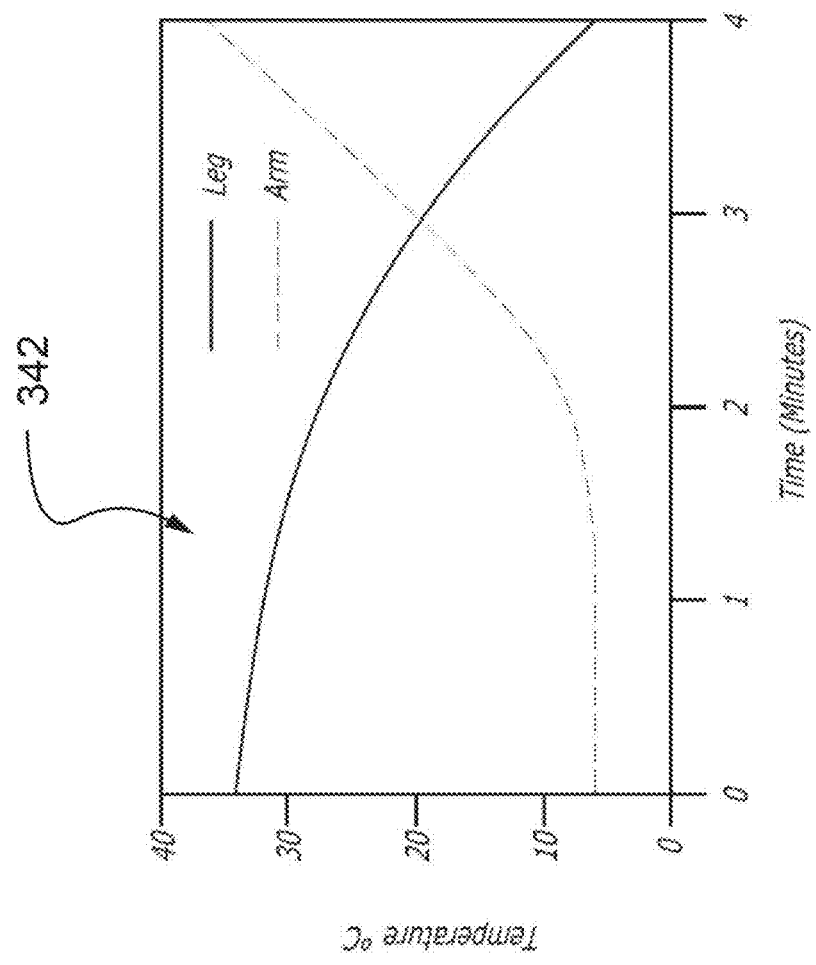
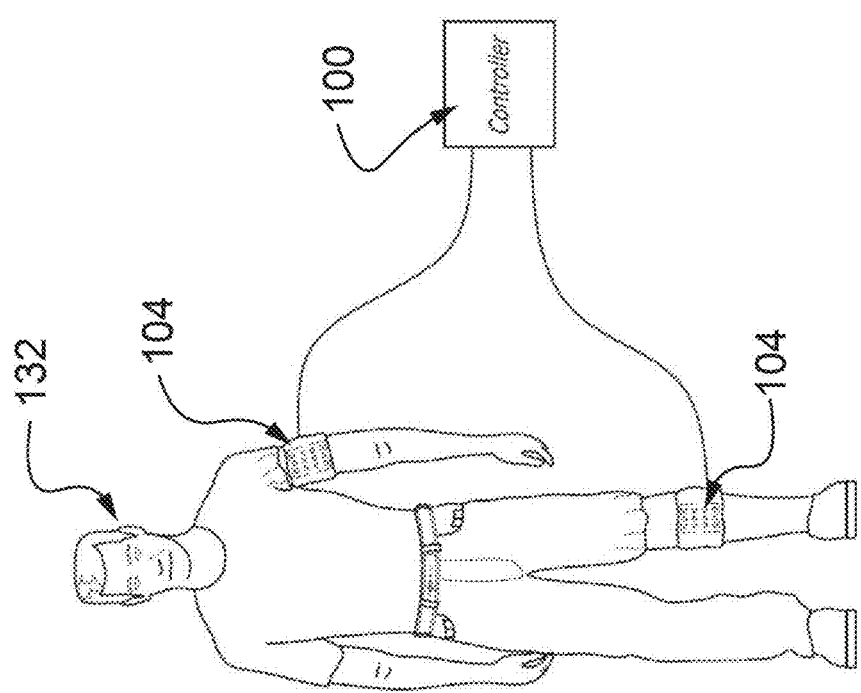
FIG. 68H

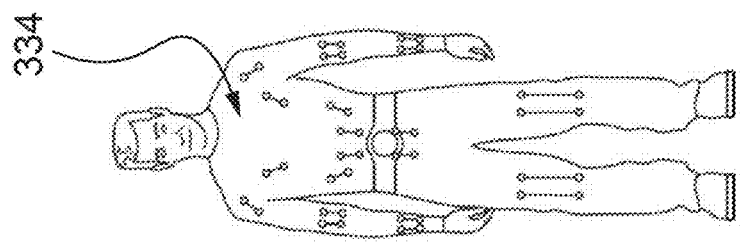
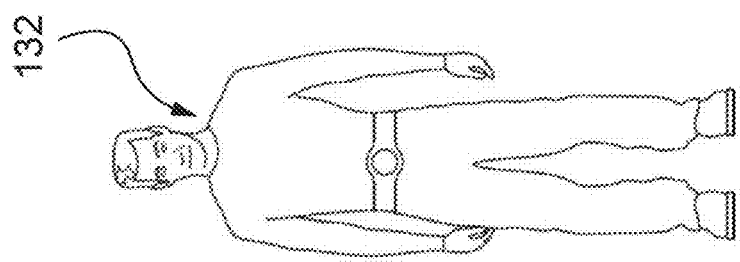
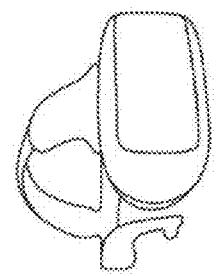
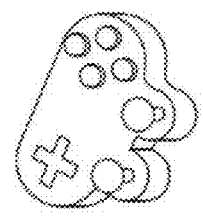
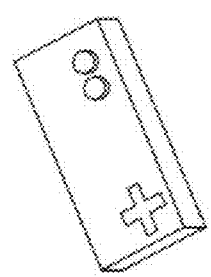
FIG. 68I

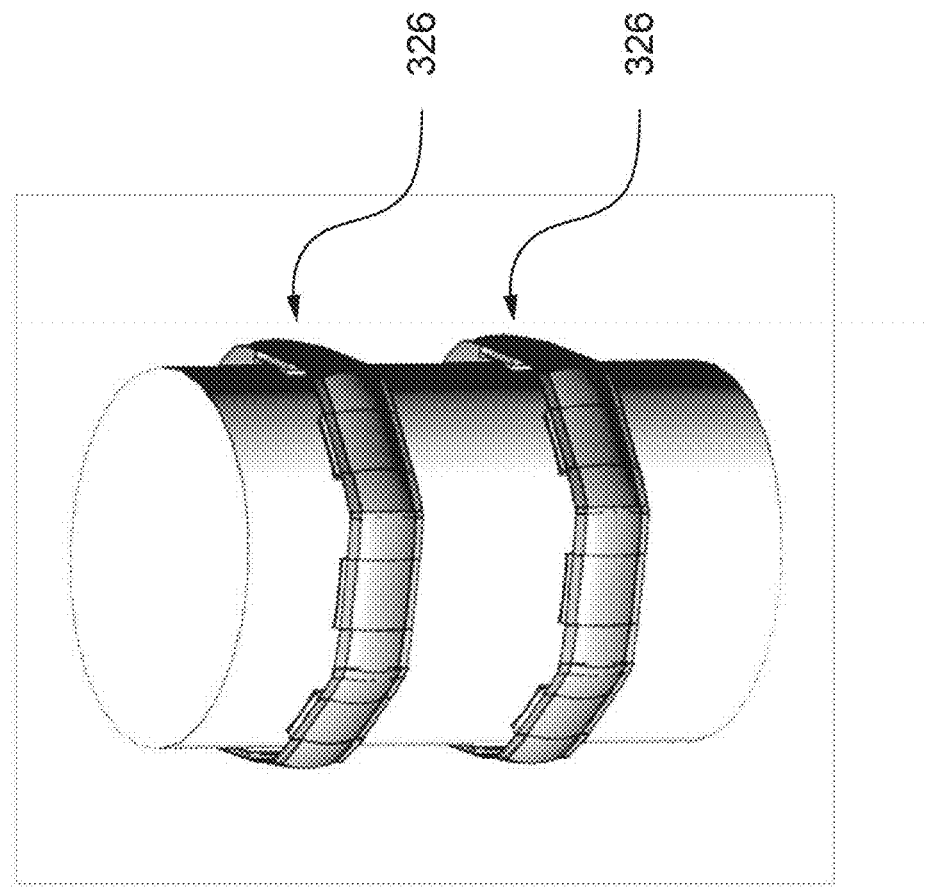
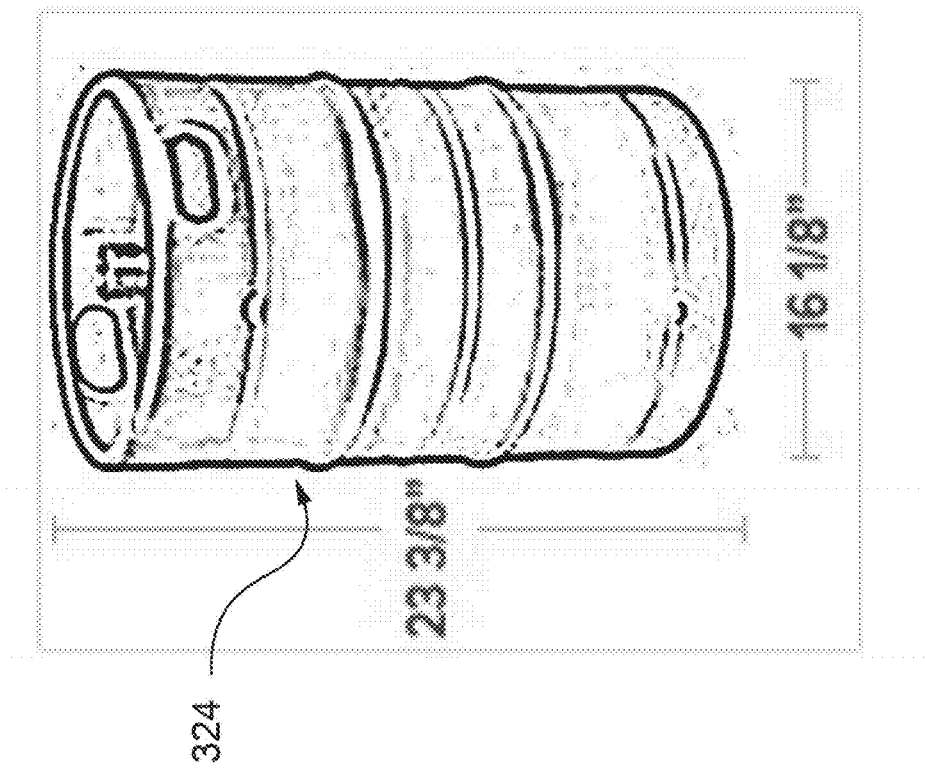
FIG. 69

HEAT EXCHANGE MODULE, SYSTEM AND METHOD

CROSS-REFERENCE TO RELATED APPLICATIONS

This application claims priority to, and is a 35 U.S.C. § 111(a) continuation of, PCT international application number PCT/US2017/054196 filed on Sep. 28, 2017, incorporated herein by reference in its entirety, which claims priority to, and the benefit of, U.S. provisional patent application Ser. No. 62/400,986 filed on Sep. 28, 2016, incorporated herein by reference in its entirety. Priority is claimed to each of the foregoing applications.

The above-referenced PCT international application was published as PCT International Publication No. WO 2018/064428 A1 on Apr. 5, 2018, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

An aspect of the technology of this disclosure pertains generally to flexible heat exchange modules (HEMs) that contain thermoelectric coolers (TECs) and can be used for heating or cooling.

Hypothermia treatment of patients is used for a variety of applications, including but not limited to treatment of brain injuries, spinal cord injuries, muscle injuries, joint injuries, avoidance of side effects during chemotherapy treatment, such as hair loss, and as a neuroprotective agent for cardiac arrest and neonatal hypoxic ischemic encephalopathy. This treatment is typically afforded by the use of ice packs and/or chemical cool packs that provide incomplete and short-lived cooling, or by pads or caps in which cooling is afforded by circulating chilled fluid.

BRIEF SUMMARY

Disclosed herein is a heat exchange module having a heat transfer fluid channel and a heat transfer plate in heat transfer relation with fluid in the channel. The reference side of a thermoelectric cooler (TEC) is in thermal contact with the plate. A heat transfer tile is in thermal contact with a user side of the TEC. The module is configured to be operatively positionable with the tile in heat transfer relation with skin of a patient. A thermistor mounted on the tile measures the temperature of the body part against which the tile is positioned and sends the temperature signal to a controller which controls the operation of the TEC.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

Figure 3:
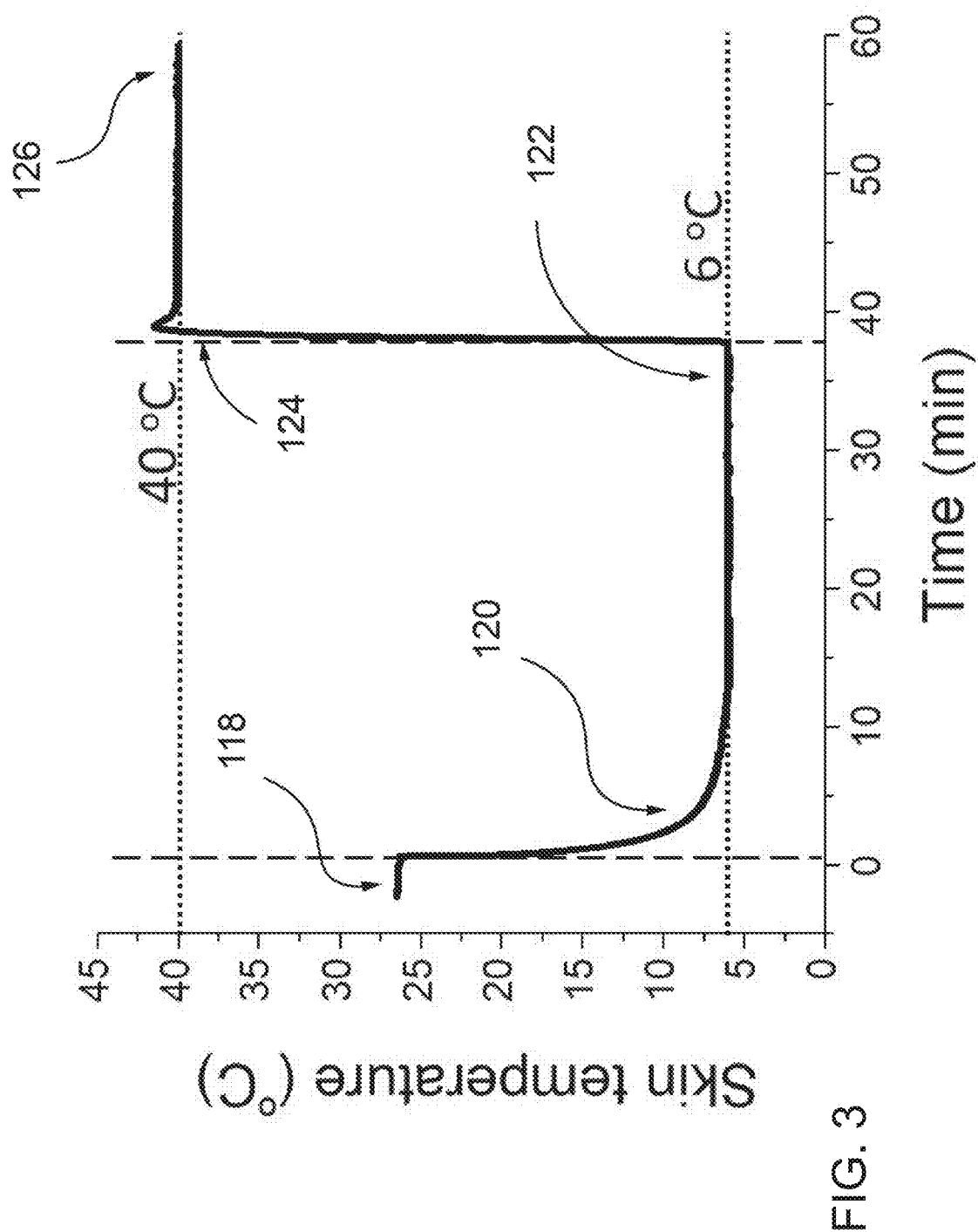

FIG. 3 is a graph showing the time course of temperature changes measured by a skin thermistor on a patient wearing an HEM on the left thigh. Time 0 indicates the initiation of the cooling process with a target temperature of 6 degrees Celsius. After 37 minutes of temperature control at 6 degrees Celsius, the target temperature was changed to 40 degrees Celsius, remaining at that value for 20 minutes.

Figure 4:
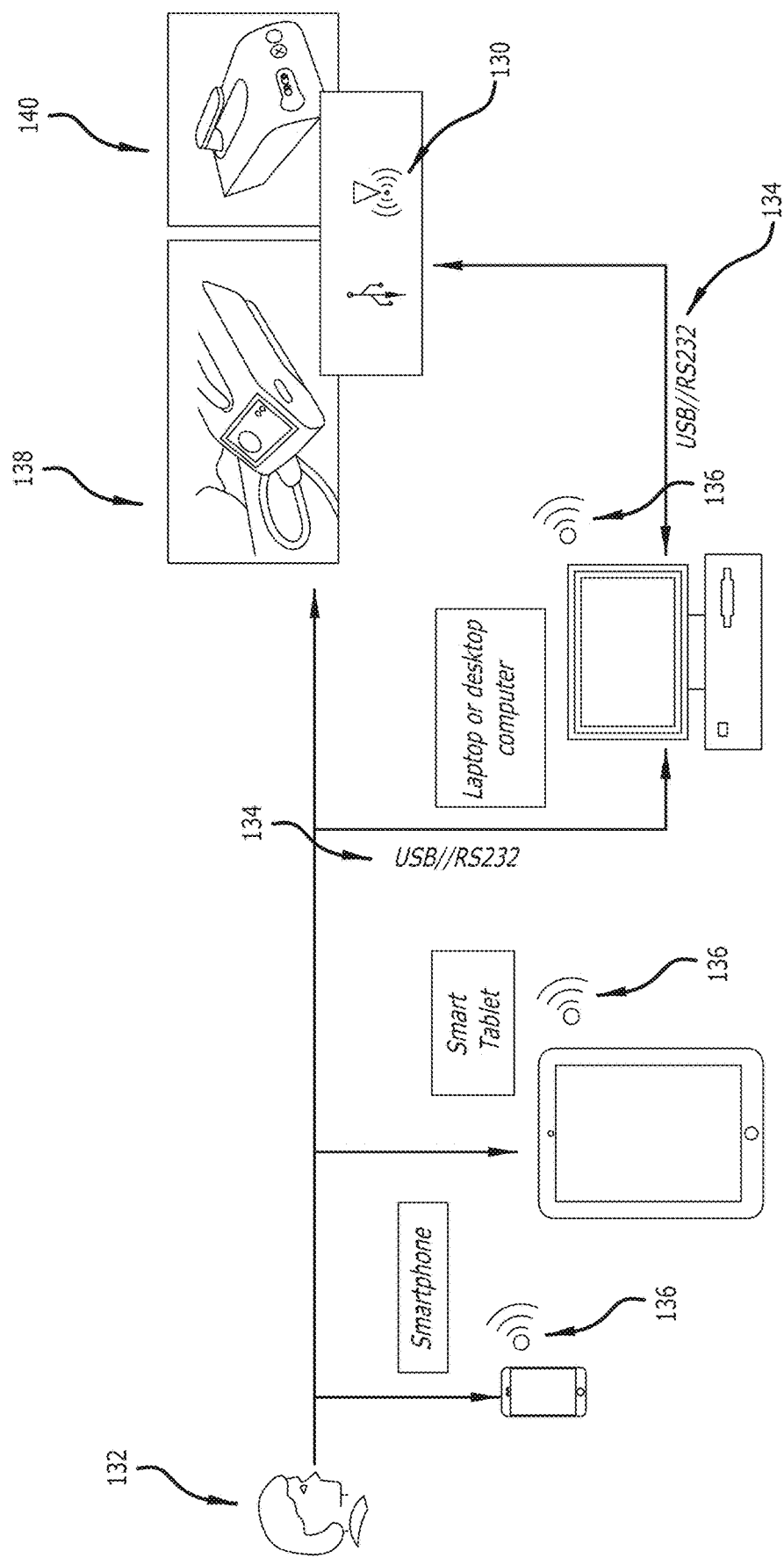

FIG. 4 is a schematic diagram showing a multiplicity of devices that can allow the user to command and/or interact with the control unit through the connectivity interface.

Figure 5:
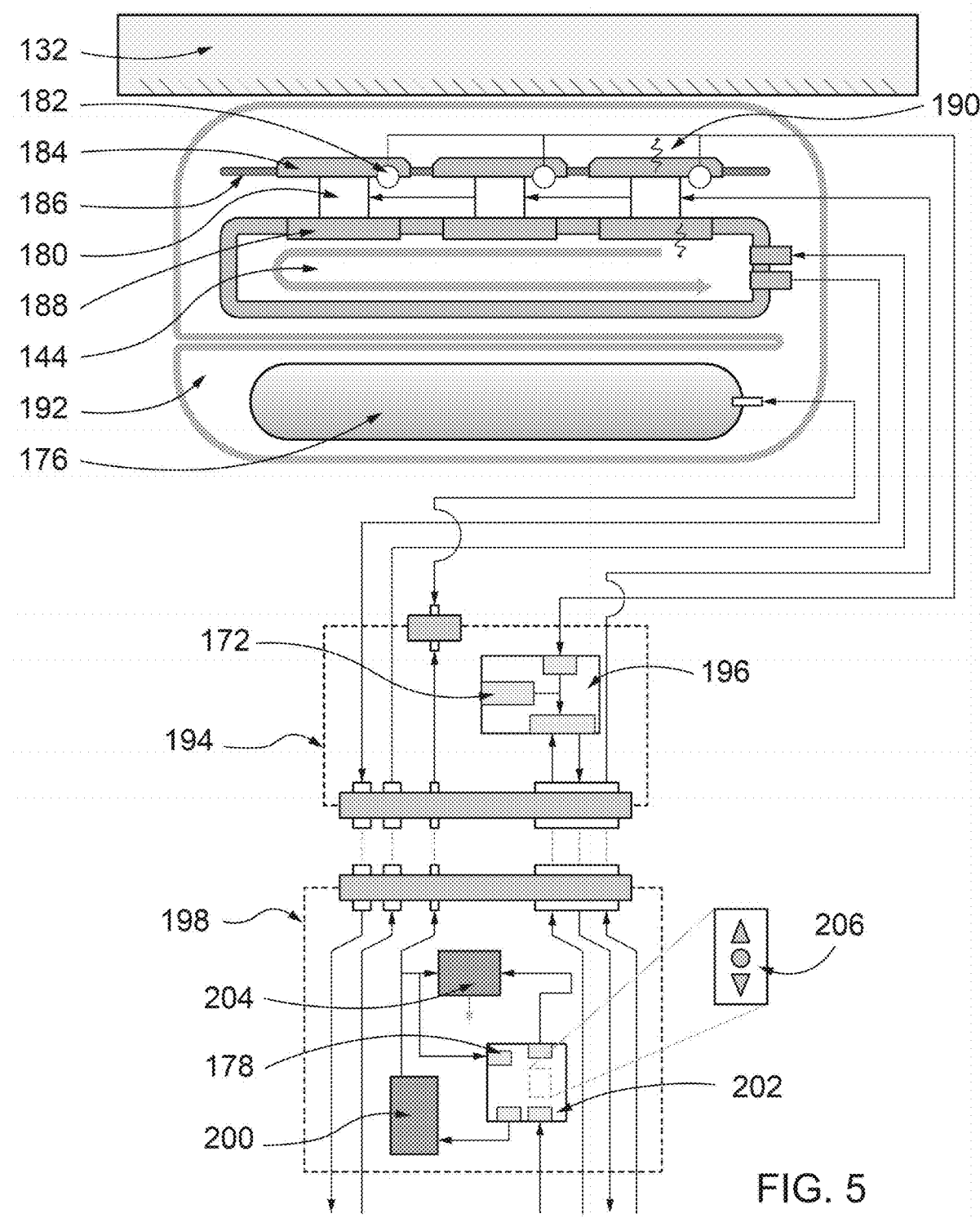

FIG. 5 is a schematic of the umbilical connectors and HEM architecture.

Figure 6:
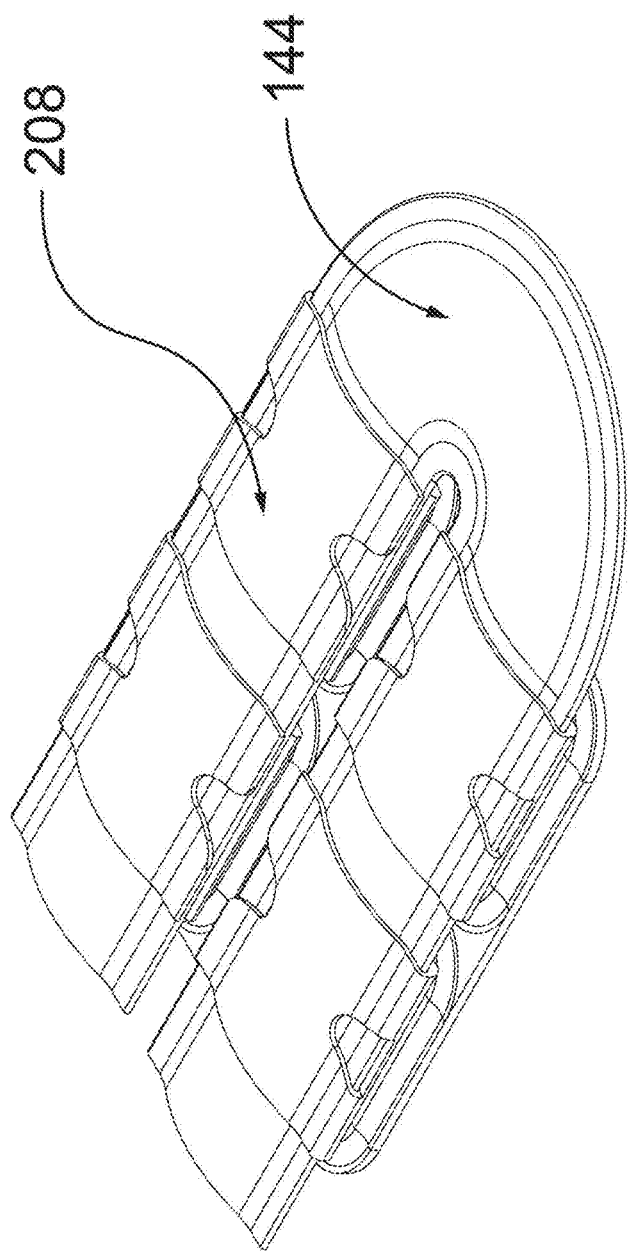

FIG. 6 is a top perspective view of a detached fluid channel assembly of the present disclosure.

Figure 7:
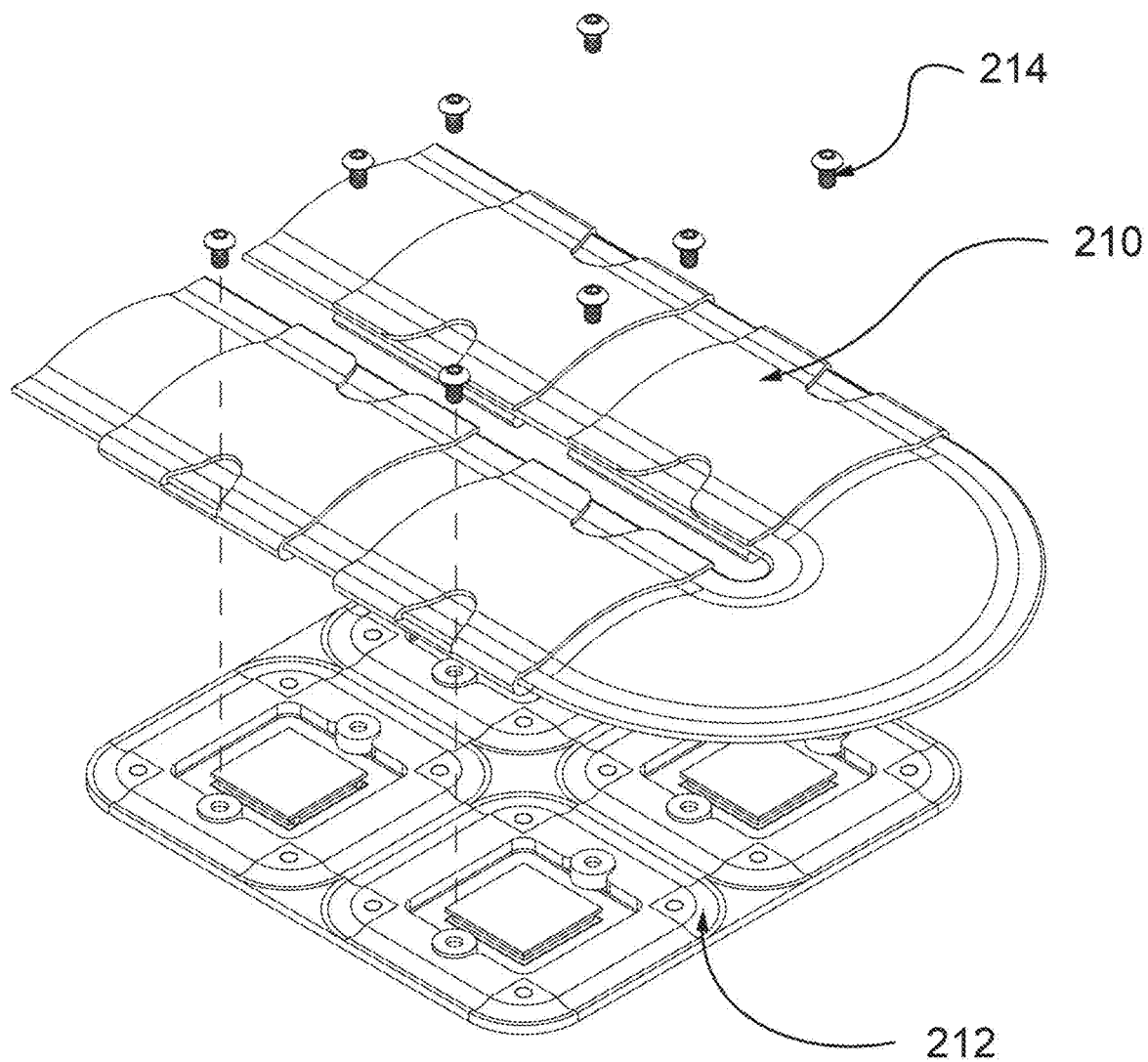

FIG. 7 is an exploded perspective view of the detached fluid channel assembly of FIG. 6 showing the upper fluid channel assembly portion separated from the lower tile assembly portion.

Figure 8:
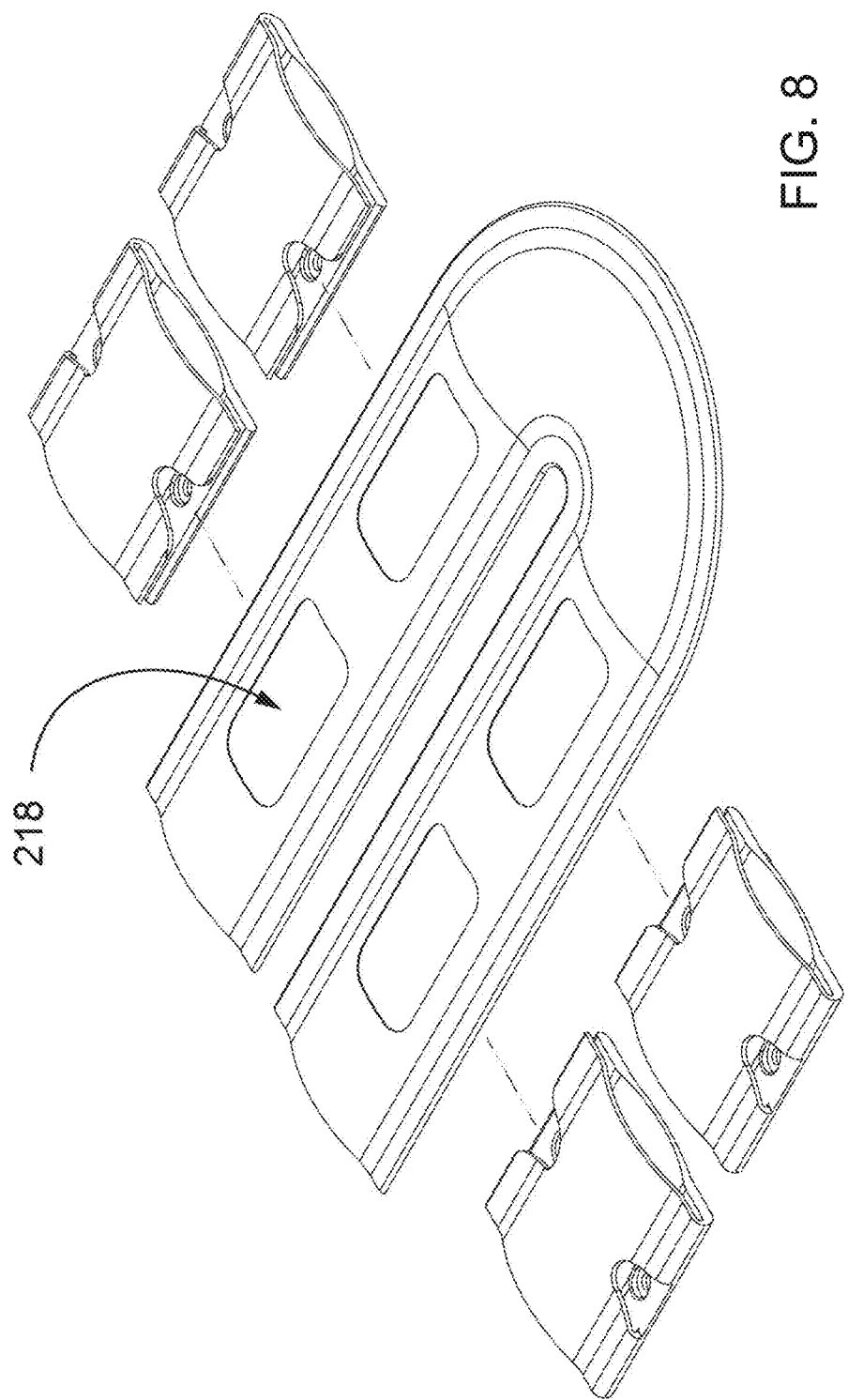

FIG. 8 is an exploded perspective view of the upper fluid channel assembly of FIG. 7 and showing the four plates separated from the U-shaped fluid channel.

Figure 9:
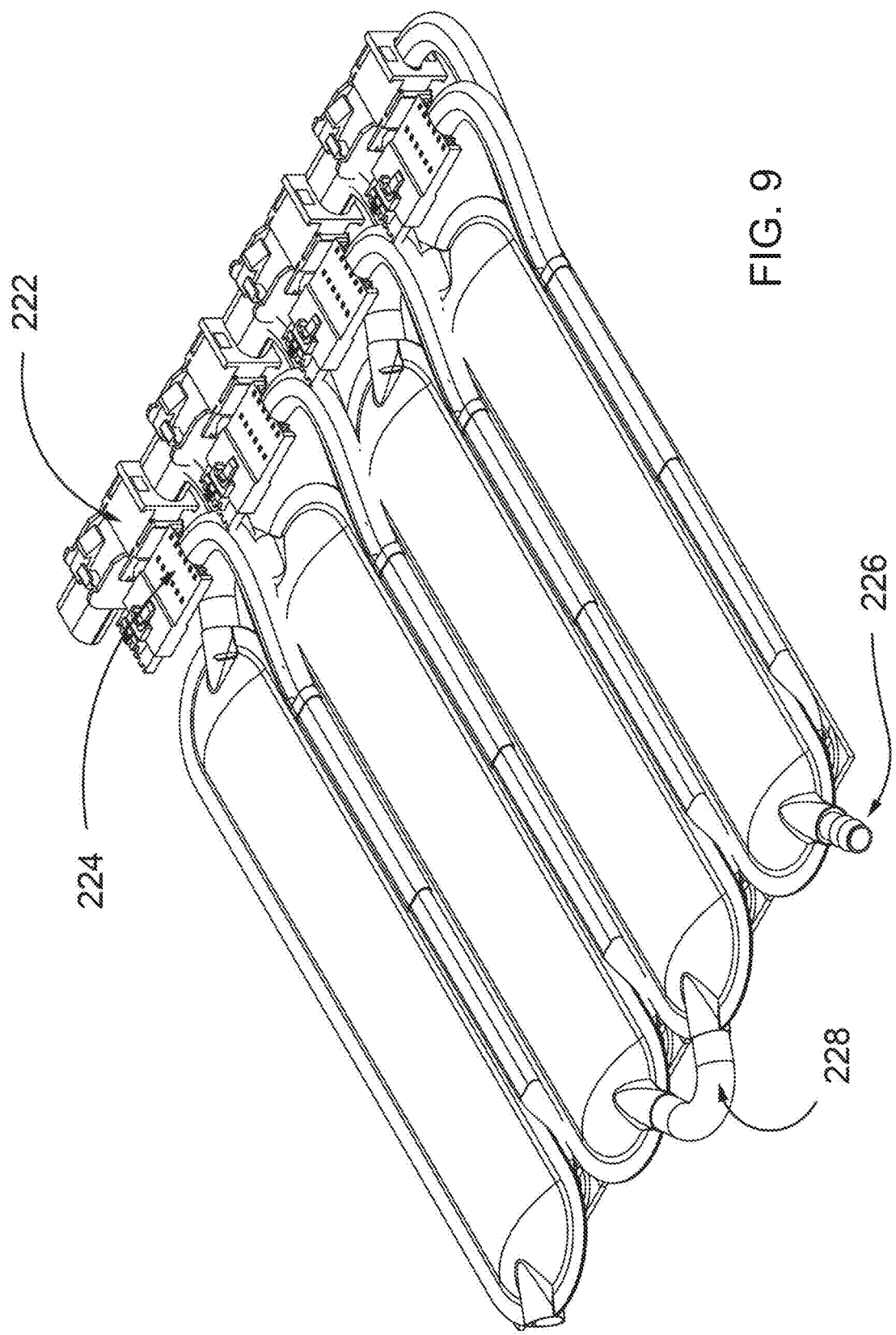

FIG. 9 is a top perspective view of a linear channels full assembly of the present disclosure.

Figure 10:
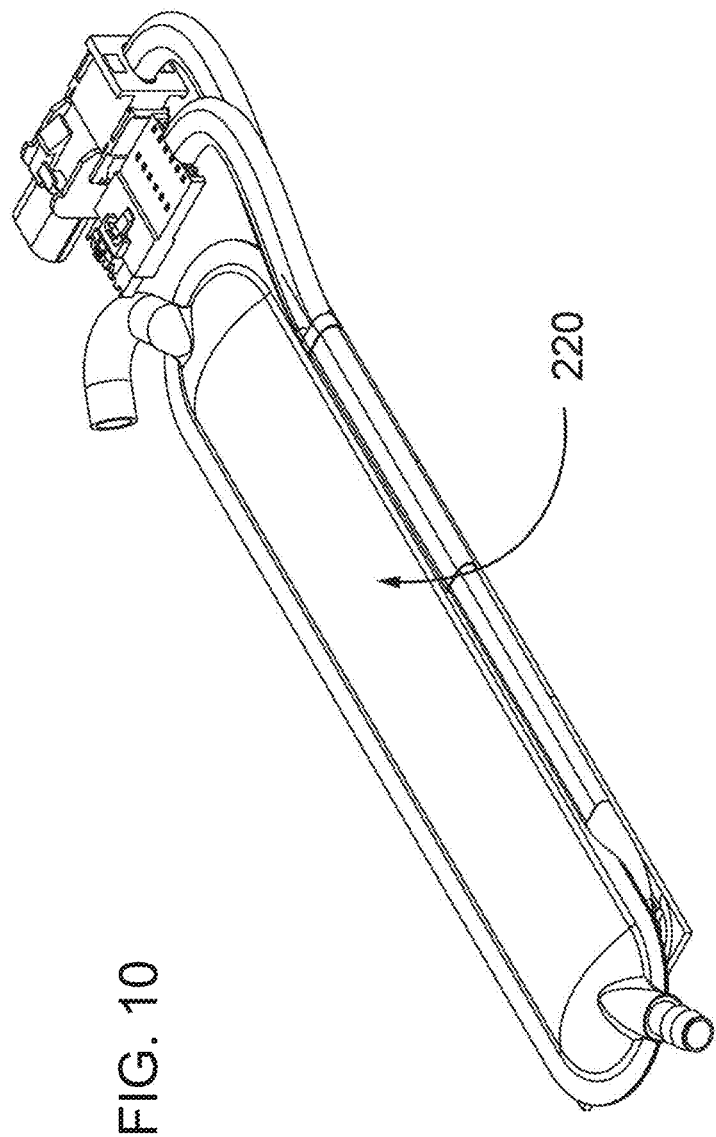

FIG. 10 is a top perspective view of a single linear channel module such as can be used in the assembly of FIG. 9.

Figure 11:
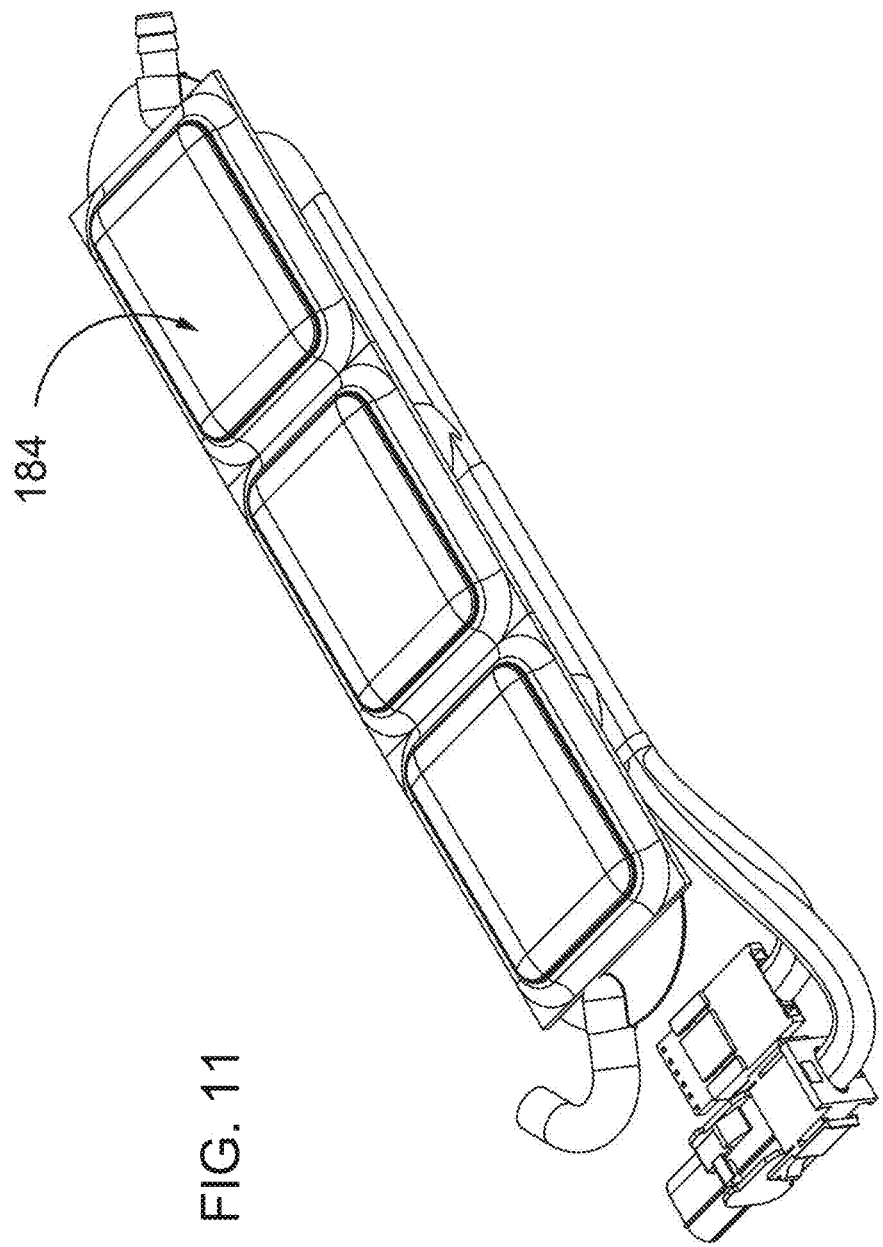

FIG. 11 is a bottom perspective view of the linear channel module of FIG. 10.

Figure 12:
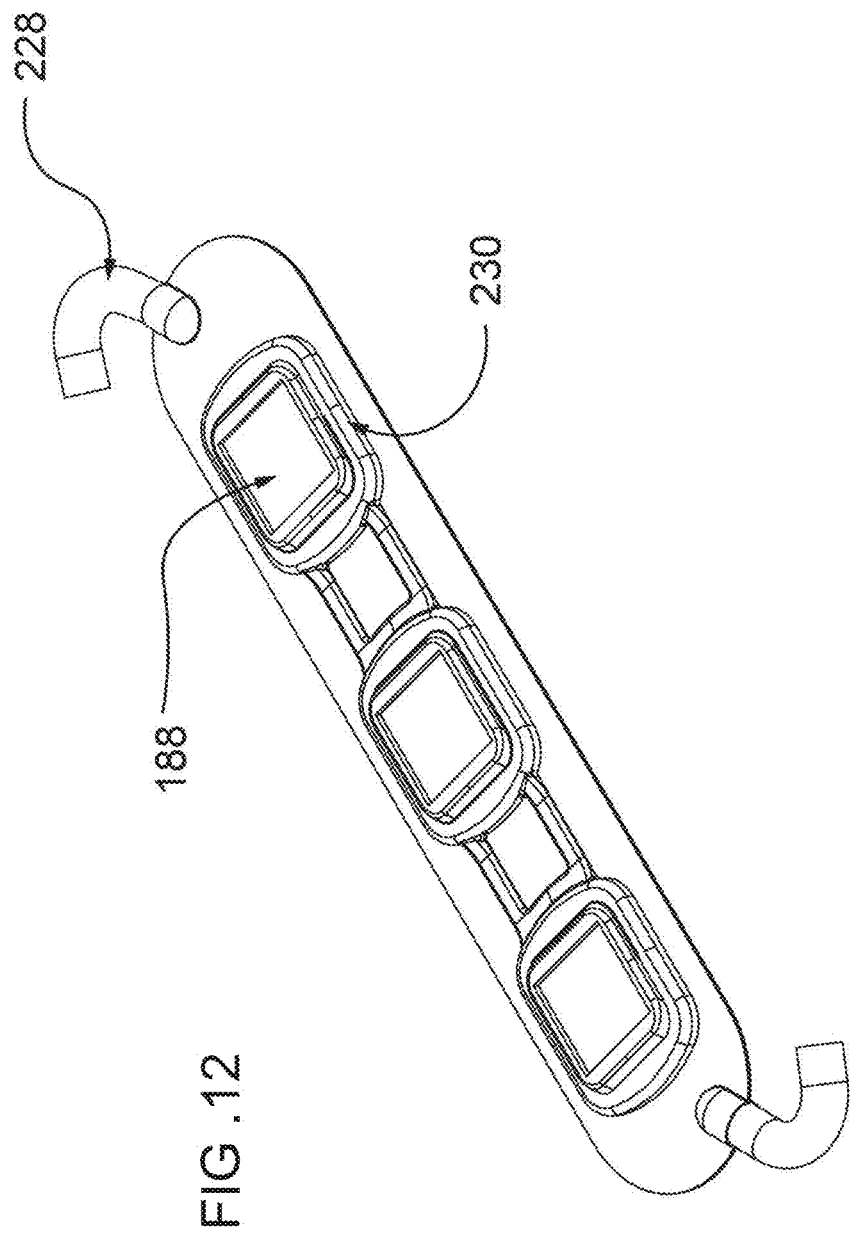

FIG. 12 is a bottom perspective view of the fluid channel subassembly of the linear channel module of FIG. 10.

Figure 13:
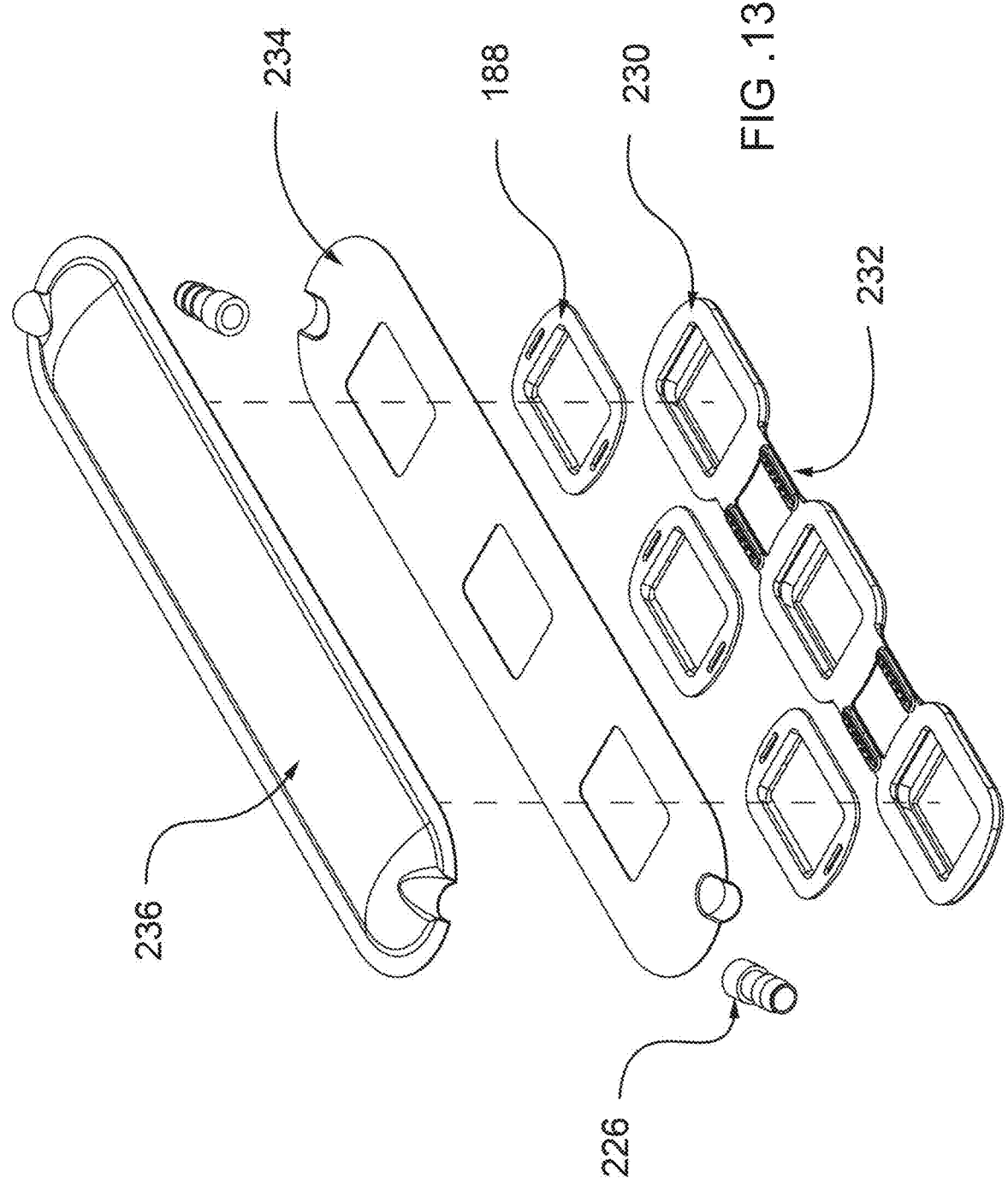

FIG. 13 is a top exploded perspective view of the fluid channel assembly of FIG. 12.

Figure 14:
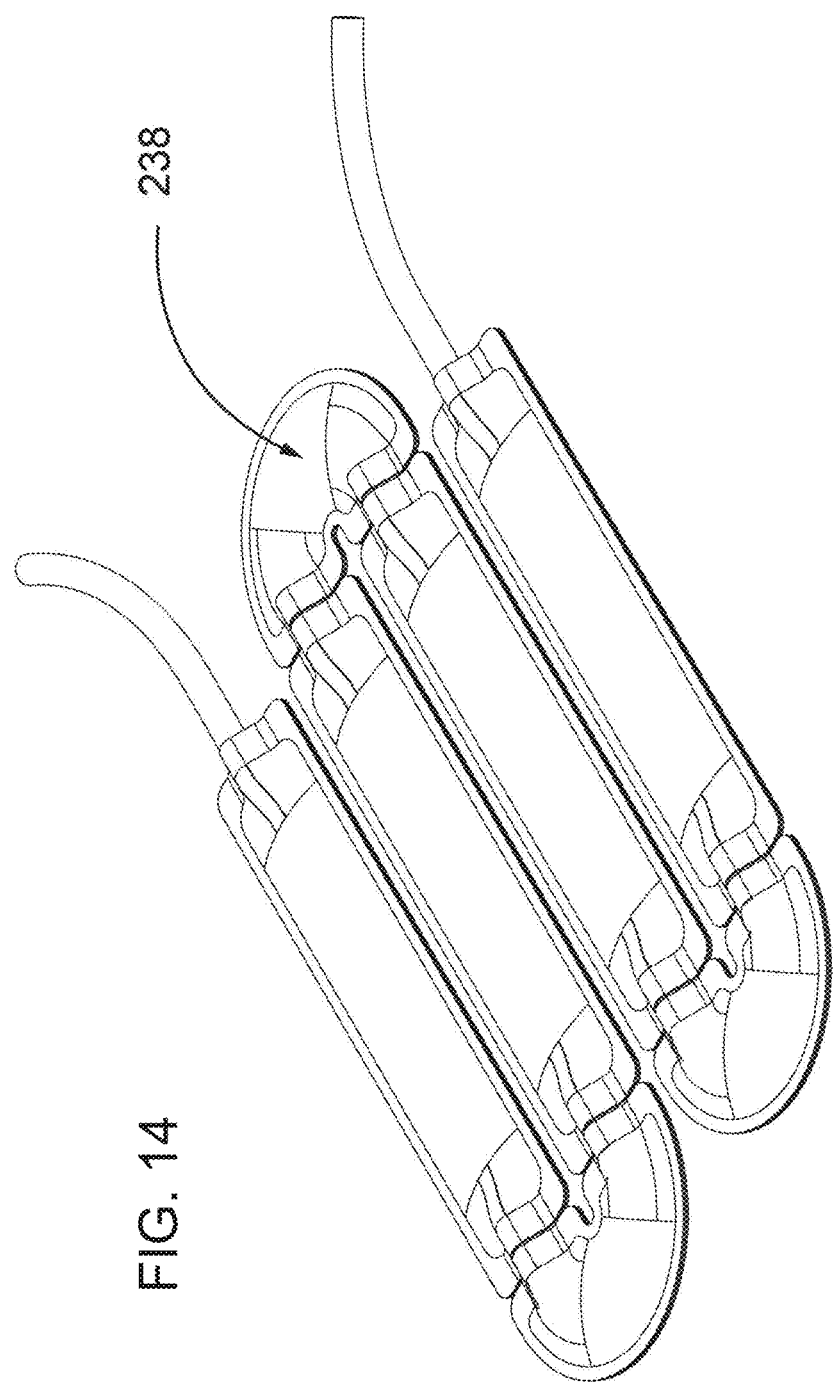

FIG. 14 is a top perspective view of a U-channel fluid channel assembly of the disclosure and which is similar to that of FIG. 12 except that the connecting tubes are replaced by U-shaped fluid channels.

Figure 15:
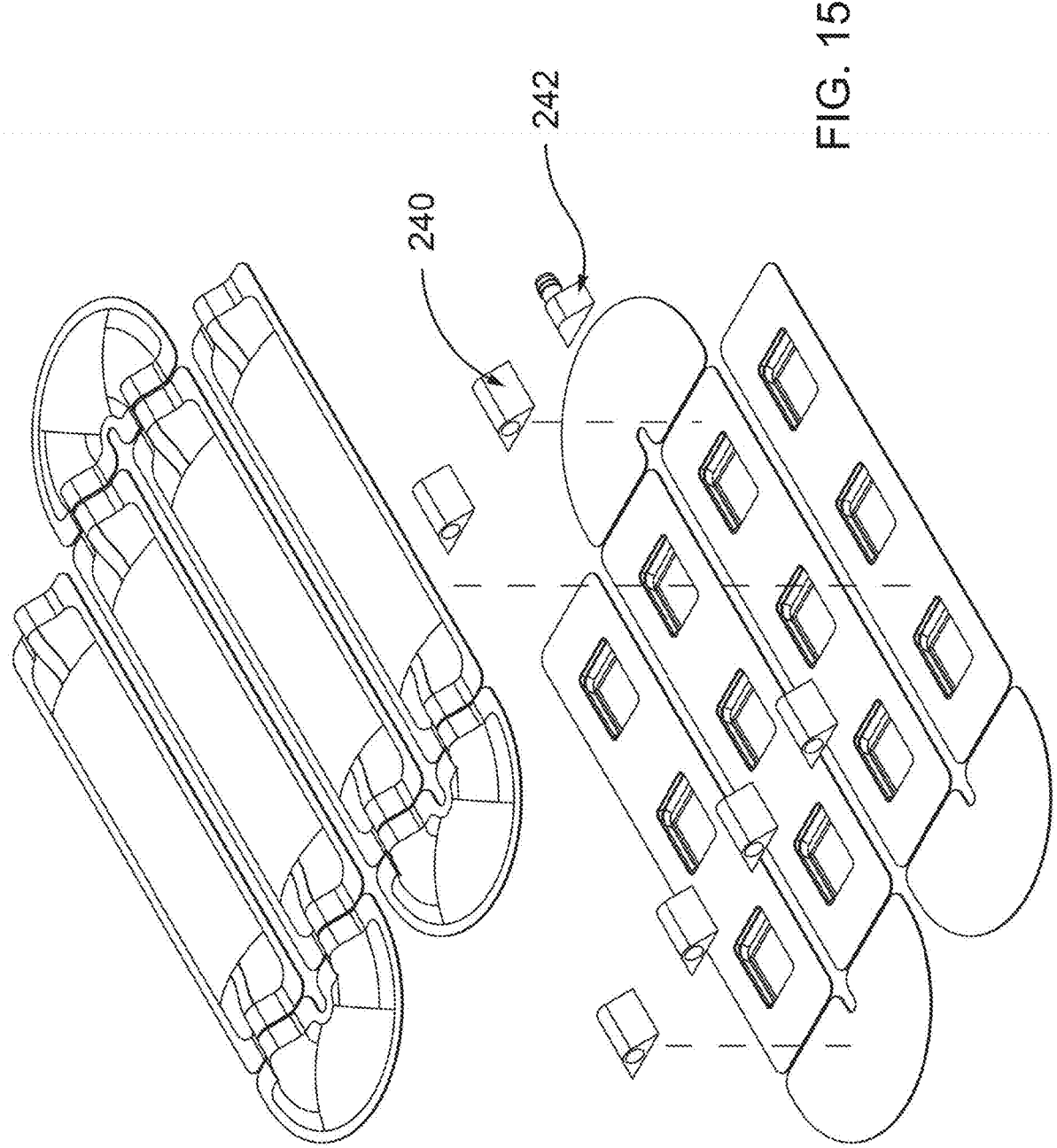

FIG. 15 is a top exploded perspective view of the assembly of FIG. 14.

Figure 16:
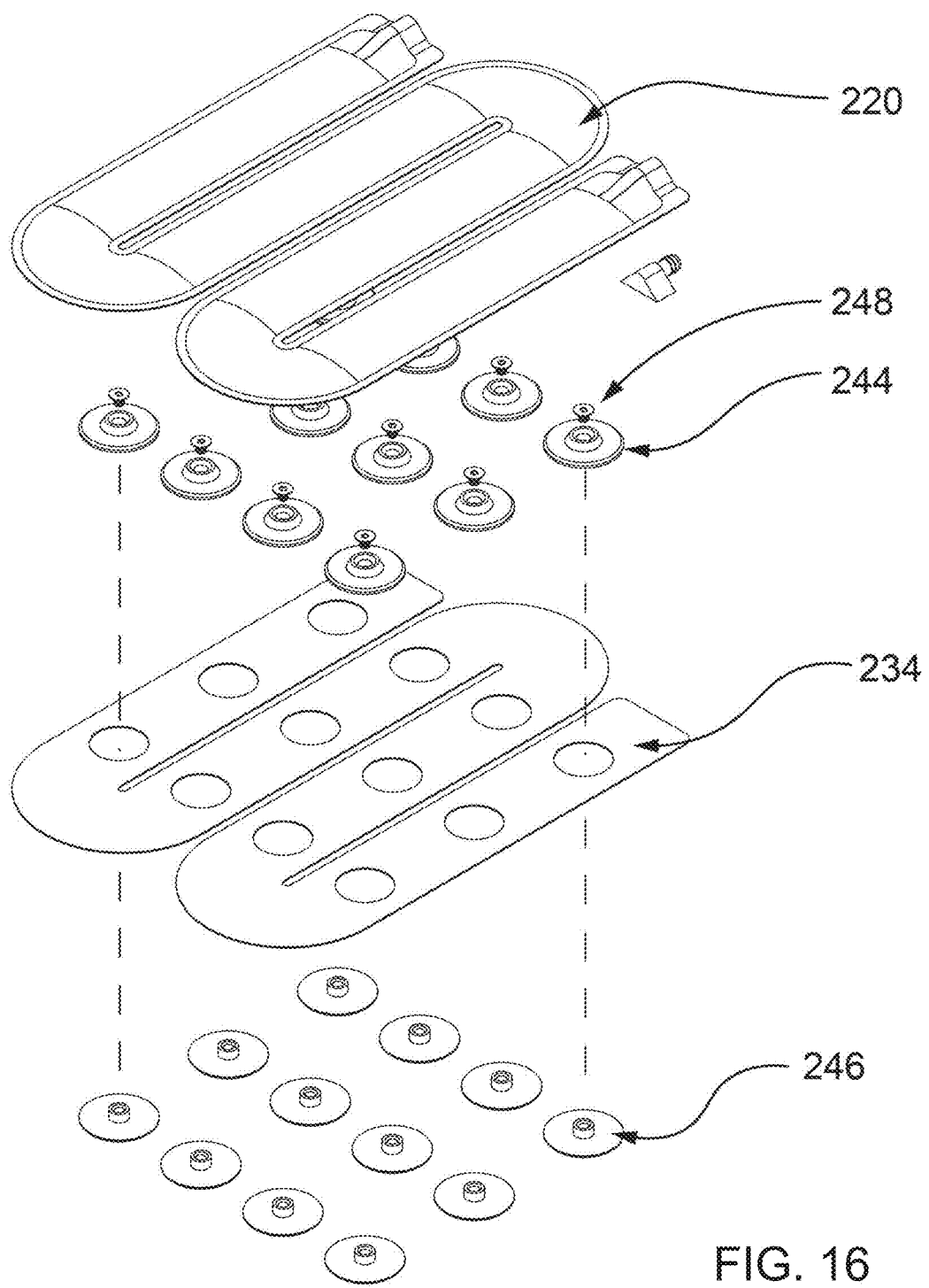

FIG. 16 is an exploded perspective view of a blind fastener channel assembly of the present disclosure.

Figure 17:
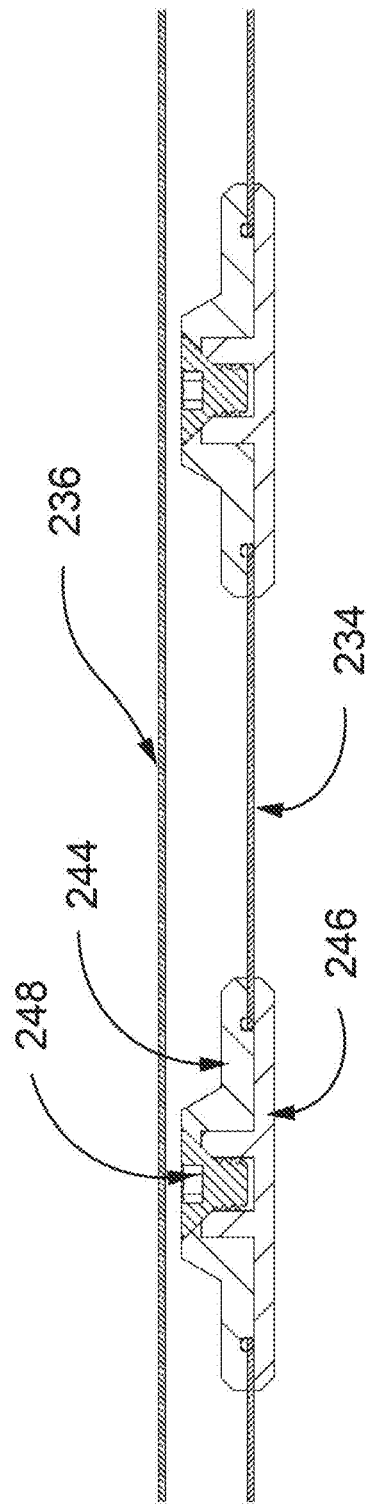

FIG. 17 is a cross-sectional view through a portion of the assembled assembly of FIG. 16.

Figure 18:
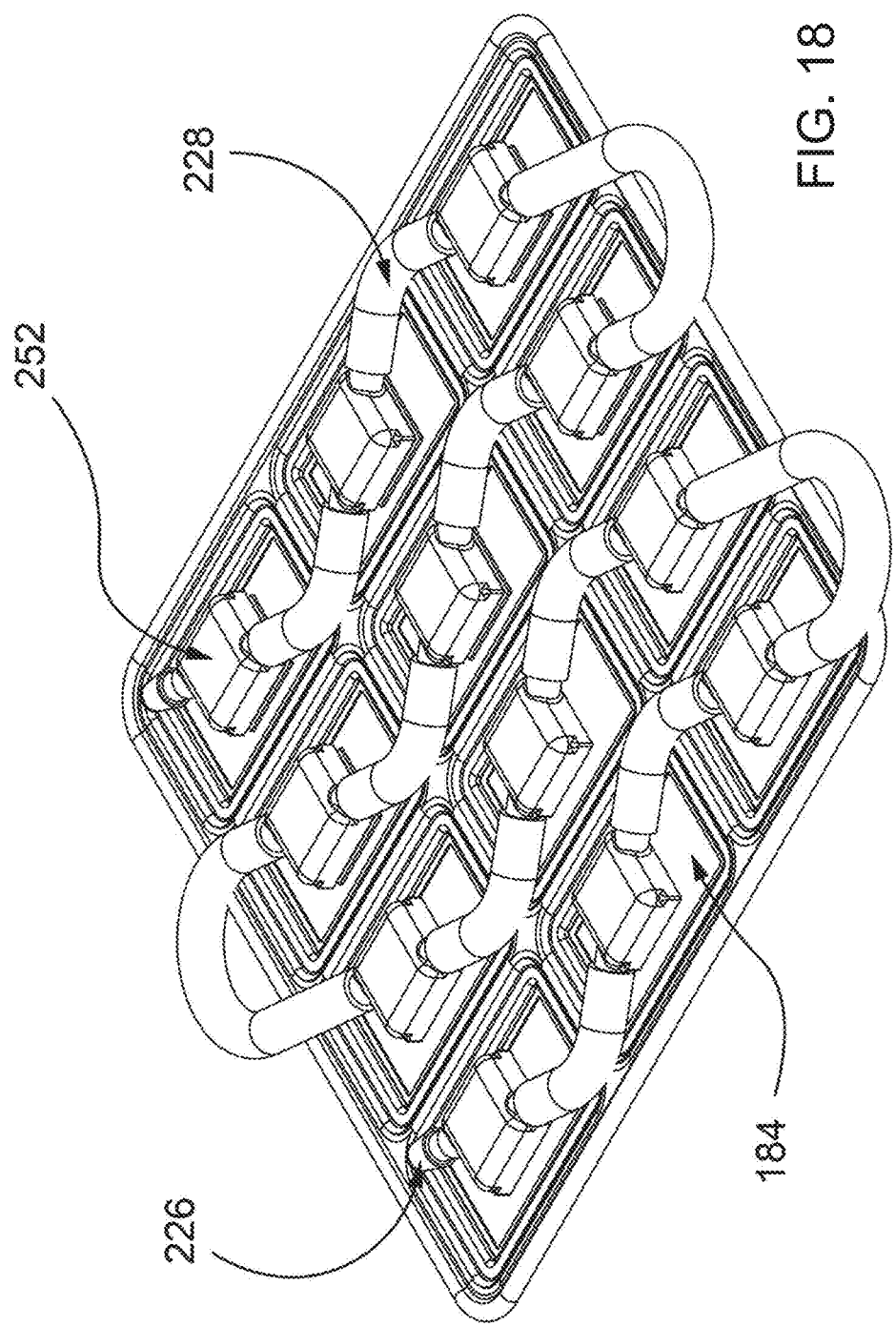

FIG. 18 is a top perspective view of a fluid block full assembly of the present disclosure.

Figure 19:
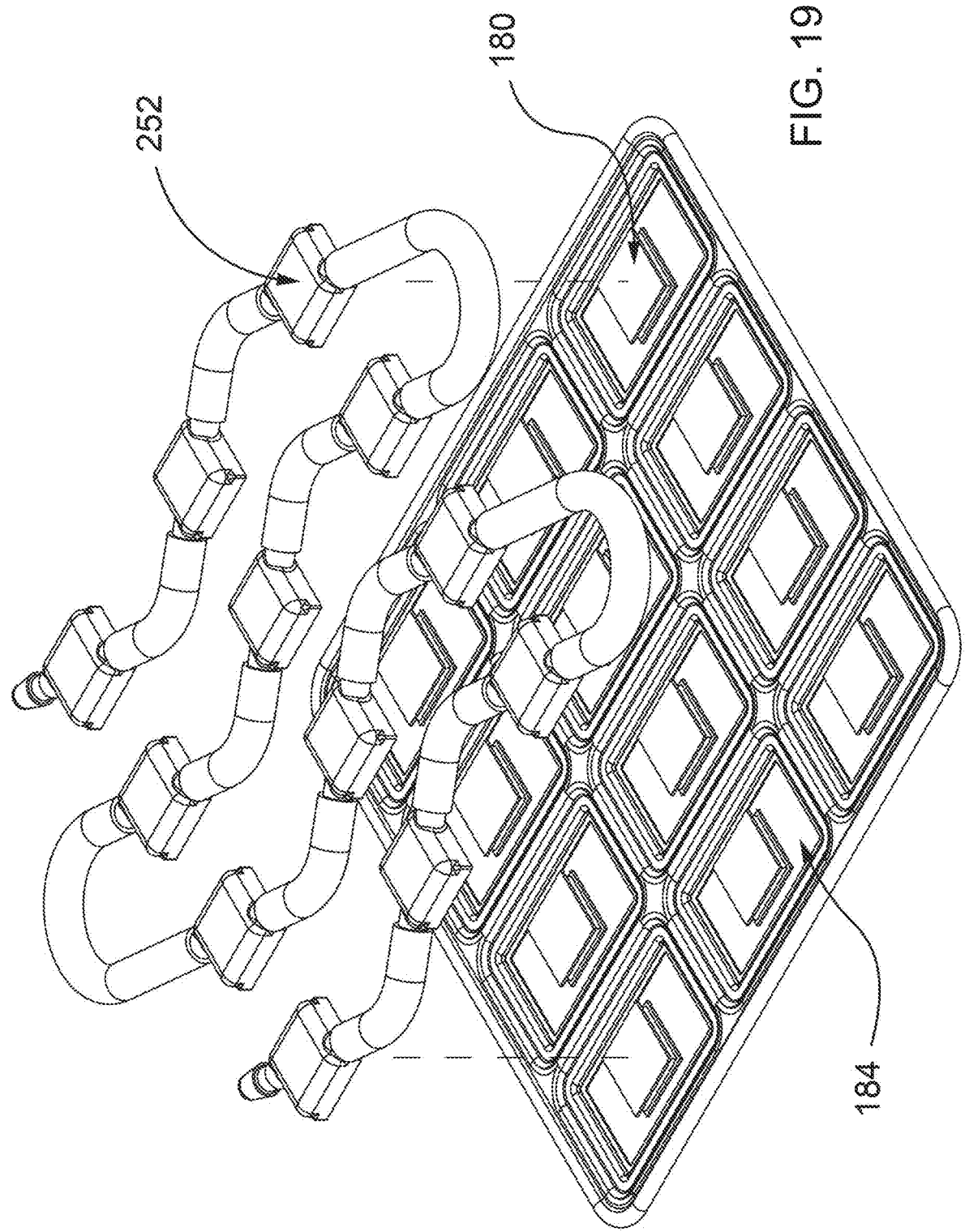

FIG. 19 is an exploded perspective view of the assembly of FIG. 18.

Figure 20:
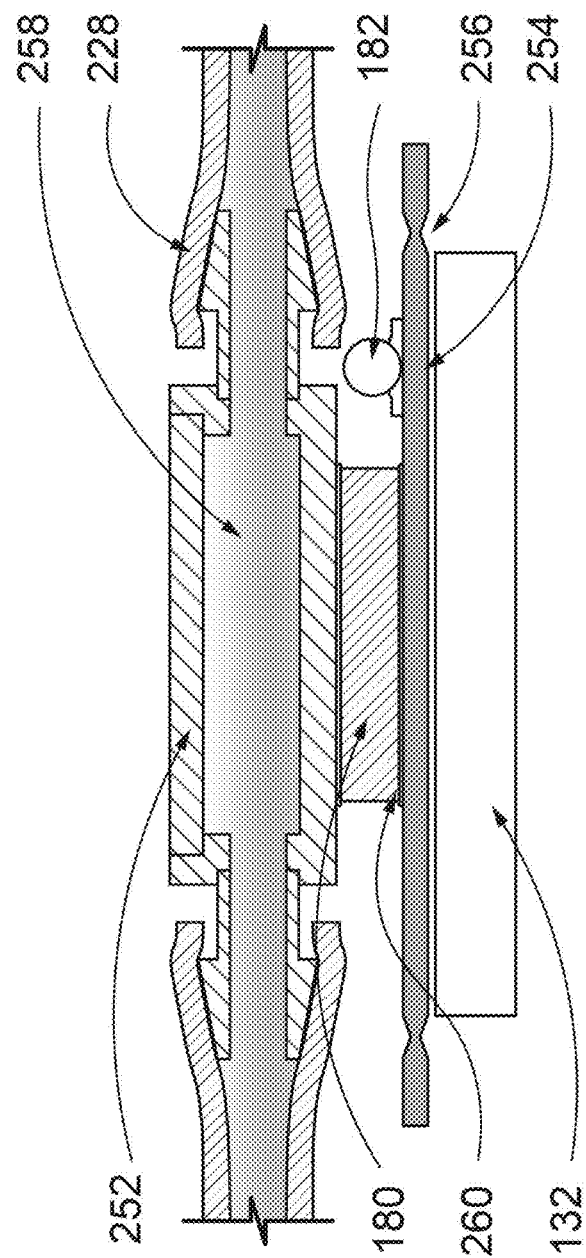

FIG. 20 is a cross-sectional view of a portion of the assembly of FIG. 18.

Figure 21:
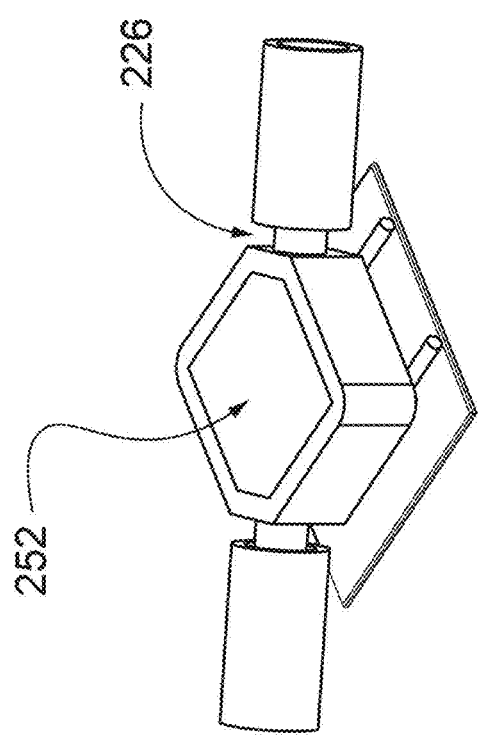

FIG. 21 is a perspective view of the fluid block of FIG. 20.

Figure 22:
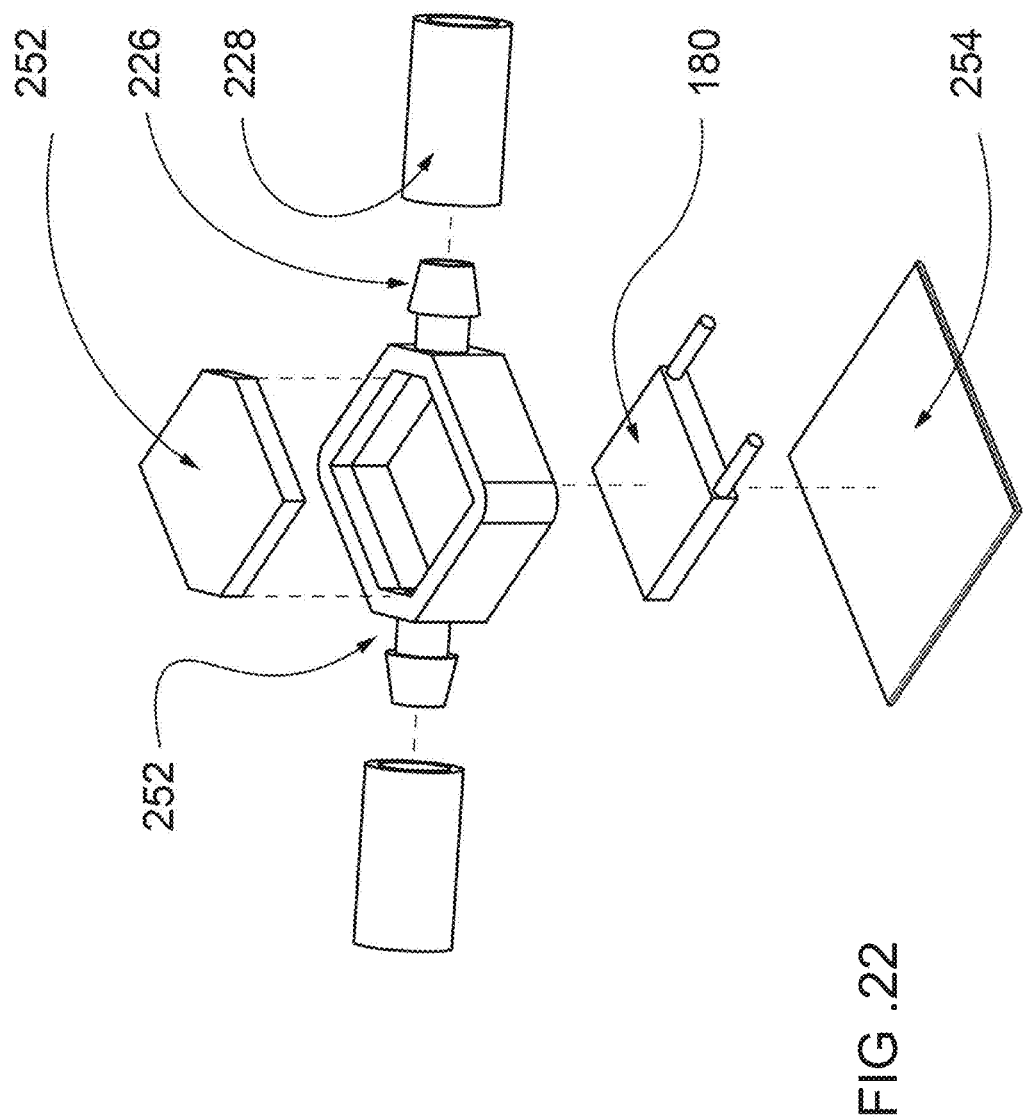

FIG. 22 is an exploded perspective view of the fluid block of FIG. 21.

Figure 23:
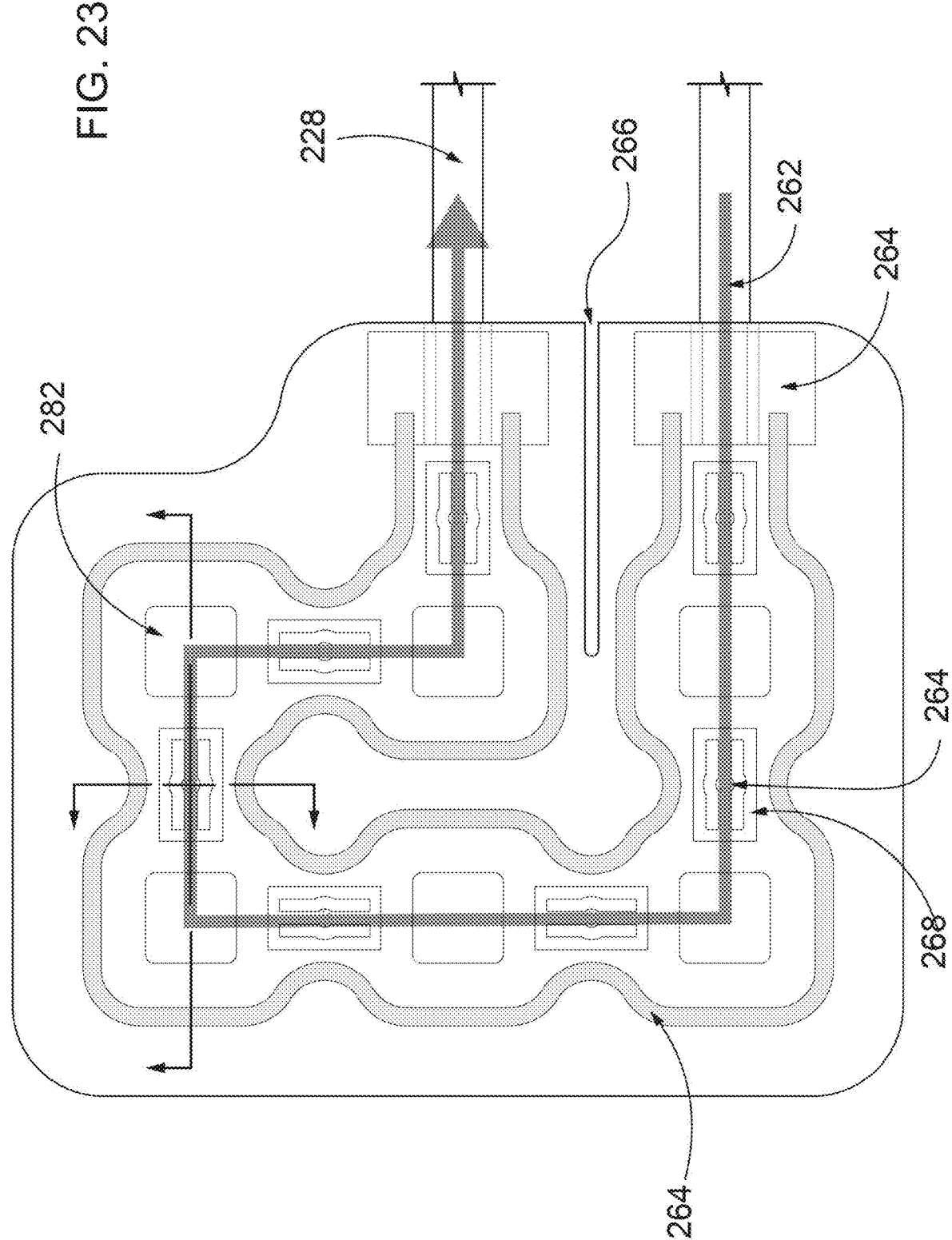

FIG. 23 is a top plan view of a fluid channel assembly of the disclosure with a transparent top sheet for purposes of illustration and an arrow indicating the flow of heat-transfer fluid therethrough.

Figure 24:
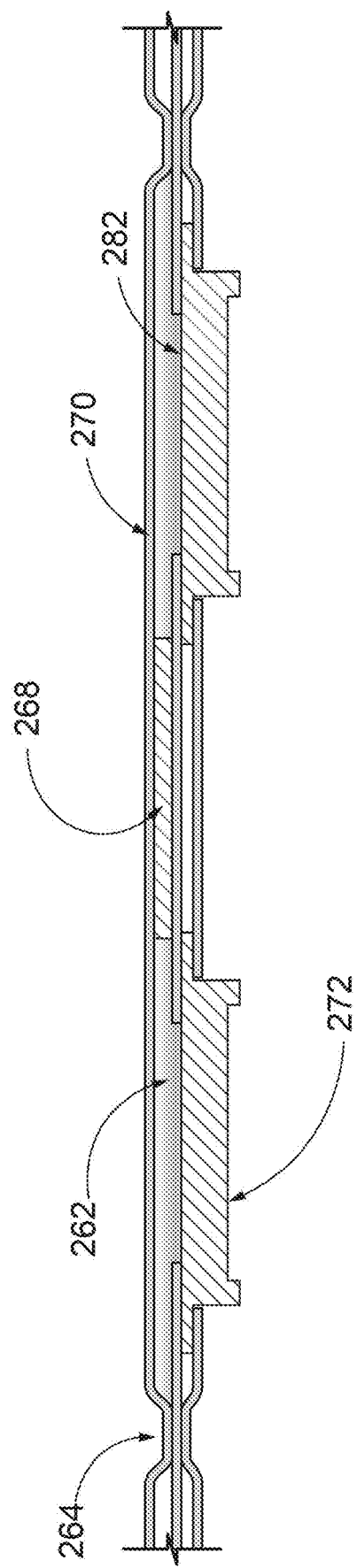

FIG. 24 is an enlarged cross-sectional view taken on line 24-24 of FIG. 23.

Figure 25:
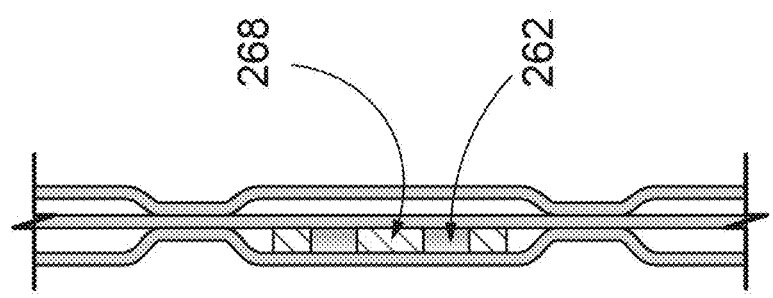

FIG. 25 is an enlarged cross-sectional view taken on line 25-25 of FIG. 23.

Figure 26:
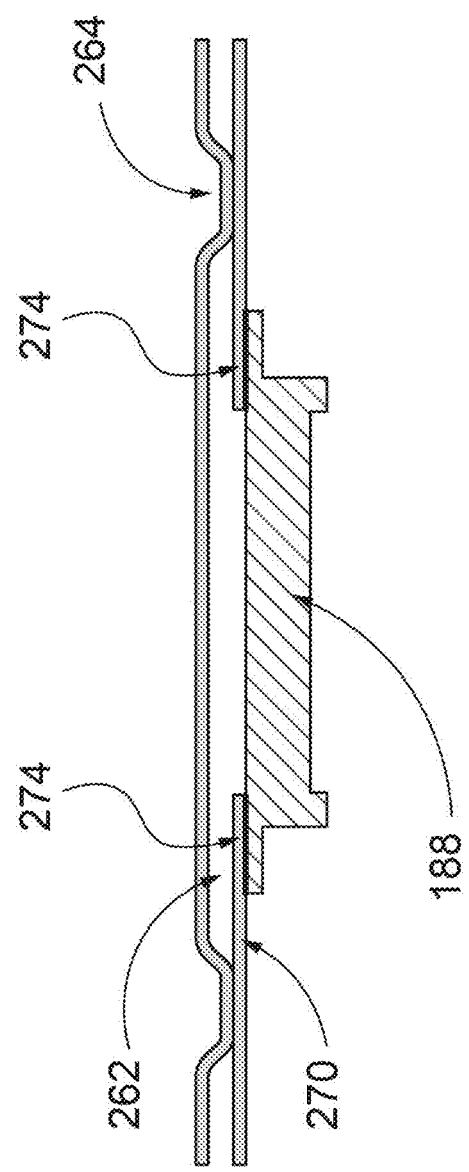

FIG. 26 is a cross-sectional view of a fluid channel assembly having one-sided embedding for the plate.

Figure 27:
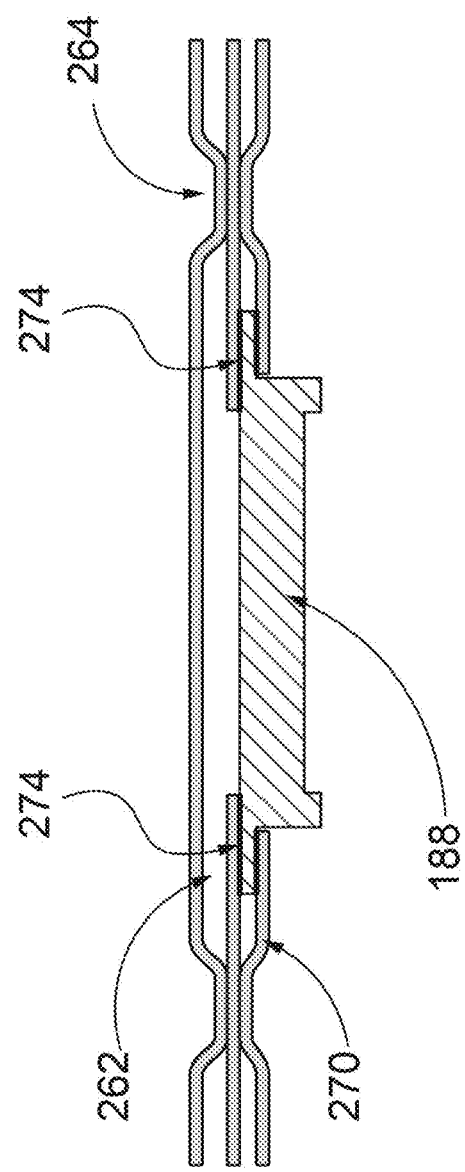

FIG. 27 is a view similar to FIG. 26 but having two-sided embedding.

Figure 28:
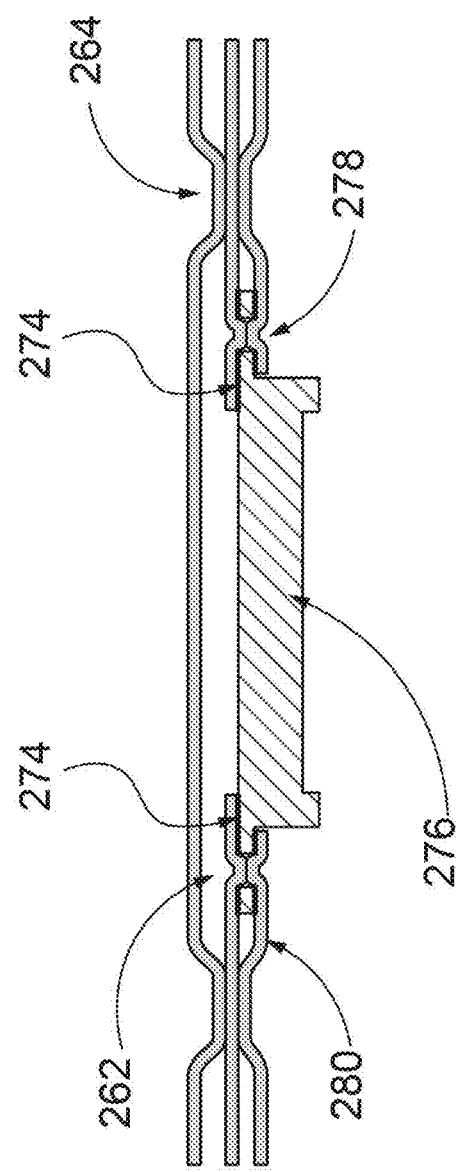

FIG. 28 is a view similar to FIG. 27 wherein the plate is slotted.

Figure 29:
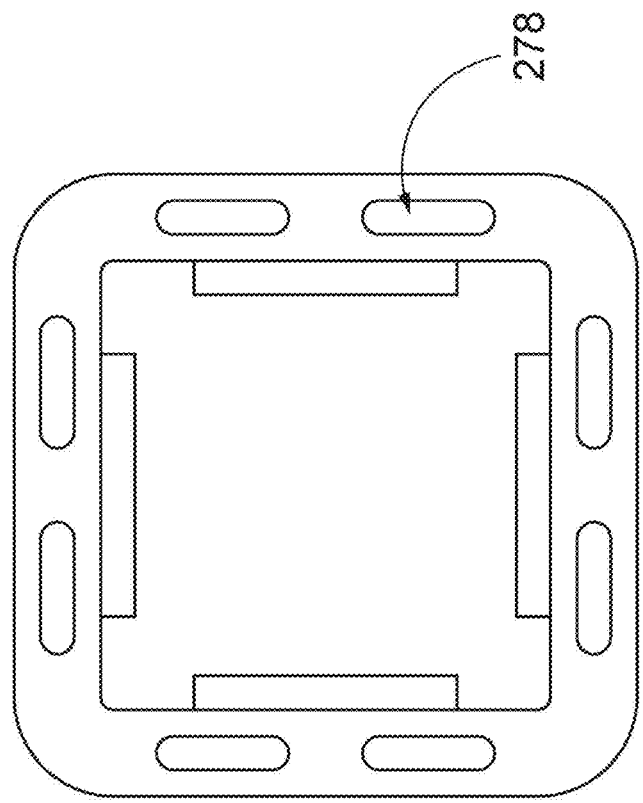

FIG. 29 is a bottom plan view of the slotted plate of FIG. 28 shown enlarged and in isolation.

Figure 30:
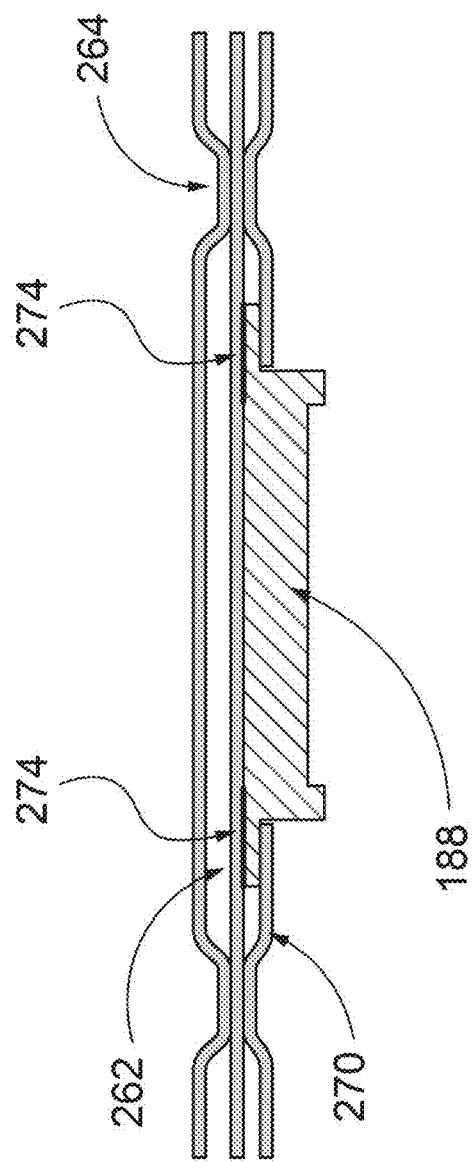

FIG. 30 is a view similar to FIG. 27 having two-sided embedding with sealing and wherein the plate does not directly contact the fluid flowing in the fluid channel.

Figure 31:
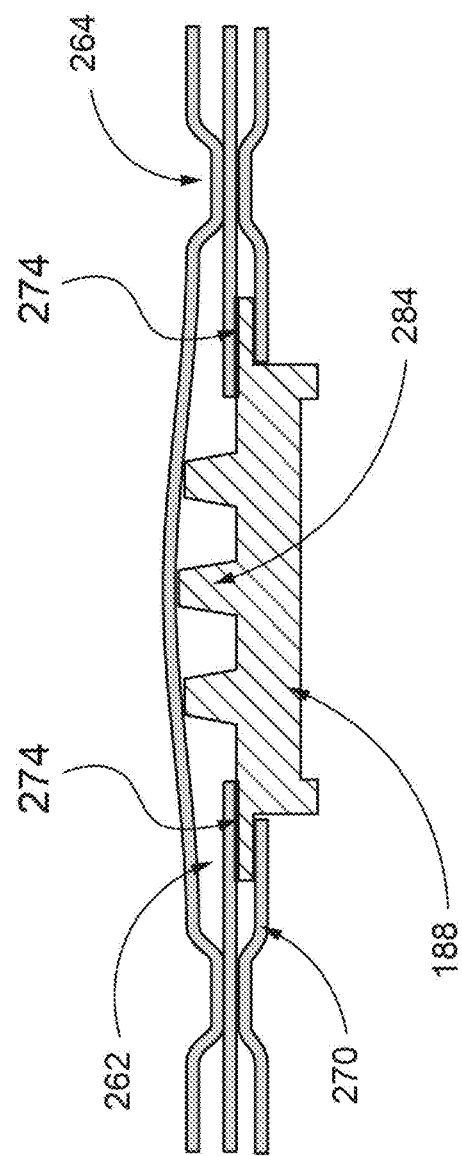

FIG. 31 is a view similar to FIG. 26 but with raised features on the plate.

FIGS. 32A-E are plan views of straight, bowtie, double strait, double cut v1, and double cut v2 standoff configurations, respectively, and alternatives to the standoffs illustrated in FIG. 23.

Figure 33:
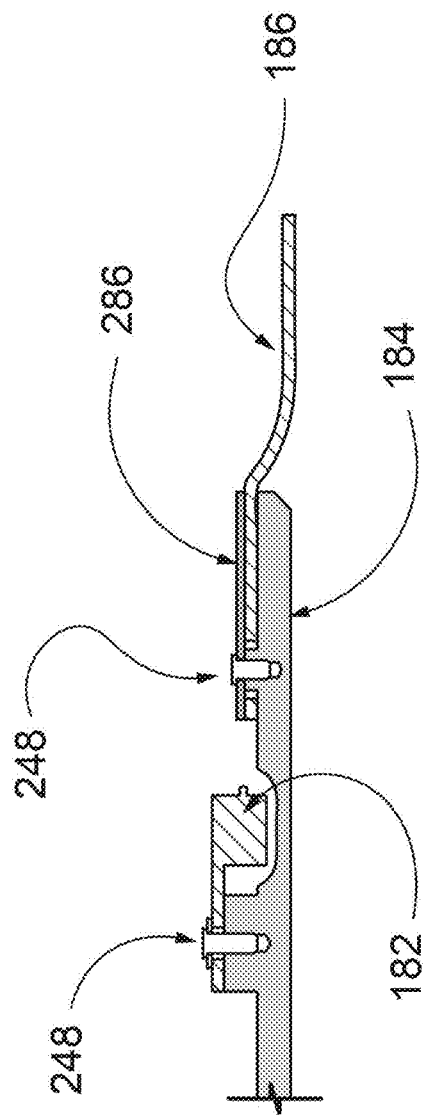
Figure 40:
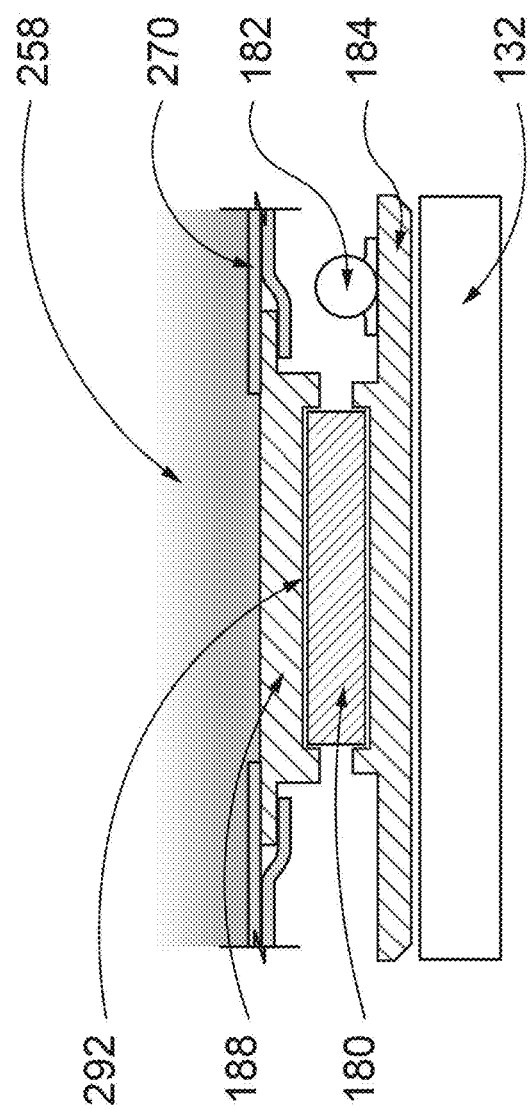

FIG. 33 is a cross-sectional view showing tile attachments using blind fastener attachments, such as might be used in the assembly of FIG. 40.

Figure 34:
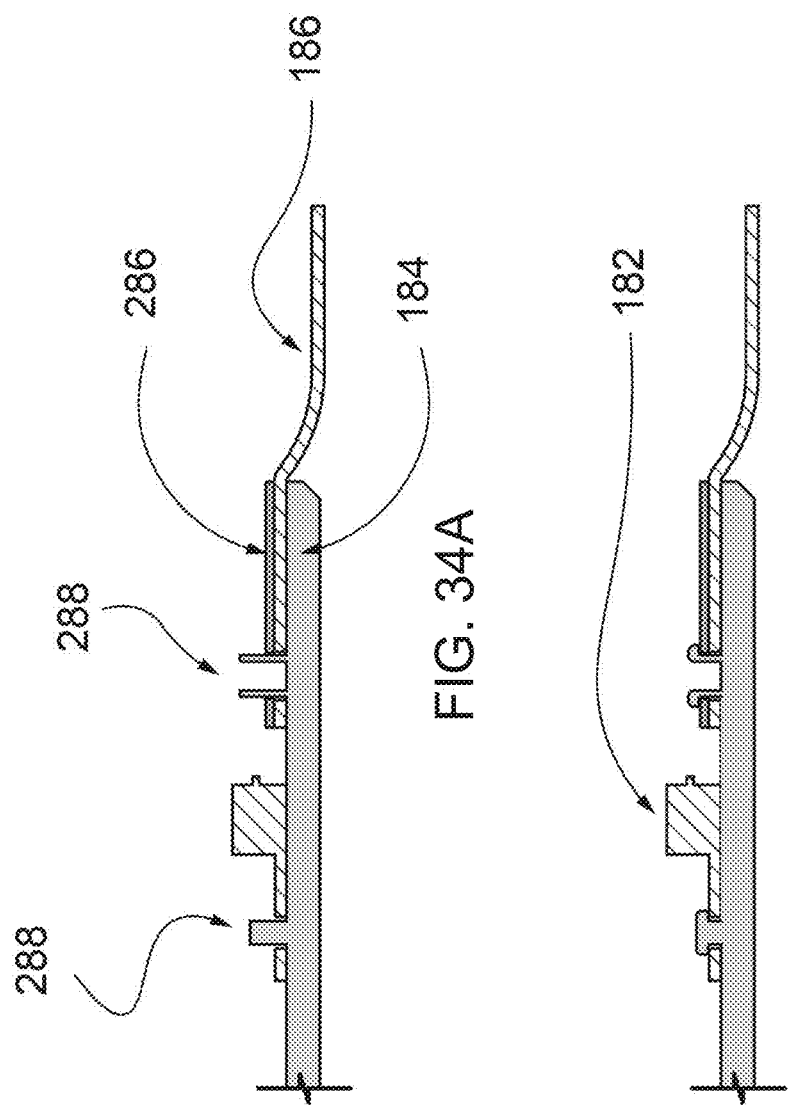

FIG. 34A is a cross-sectional view similar to FIG. 33 but showing crush post attachments instead of blind fastener attachments, and FIG. 34A shows the posts in uncrushed conditions.

FIG. 34B is a view similar to FIG. 34A but showing the posts in crushed, attachment conditions.

Figure 35:
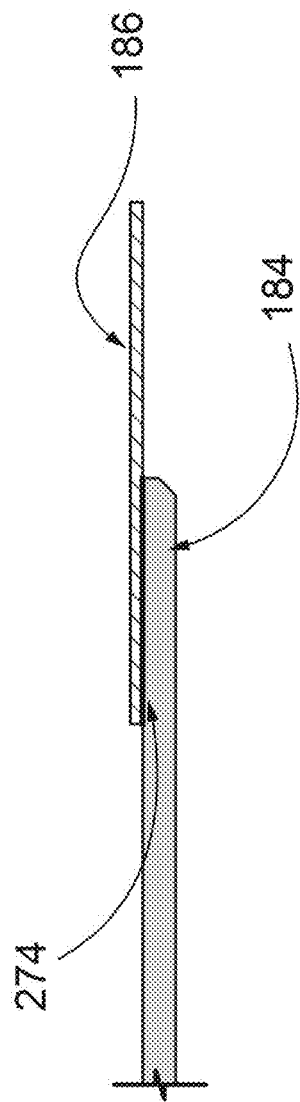

FIG. 35 is an enlarged cross-sectional view showing heat press embedding of a tile to a flexible frame, such as might be found in the assembly of FIG. 40.

Figure 36:
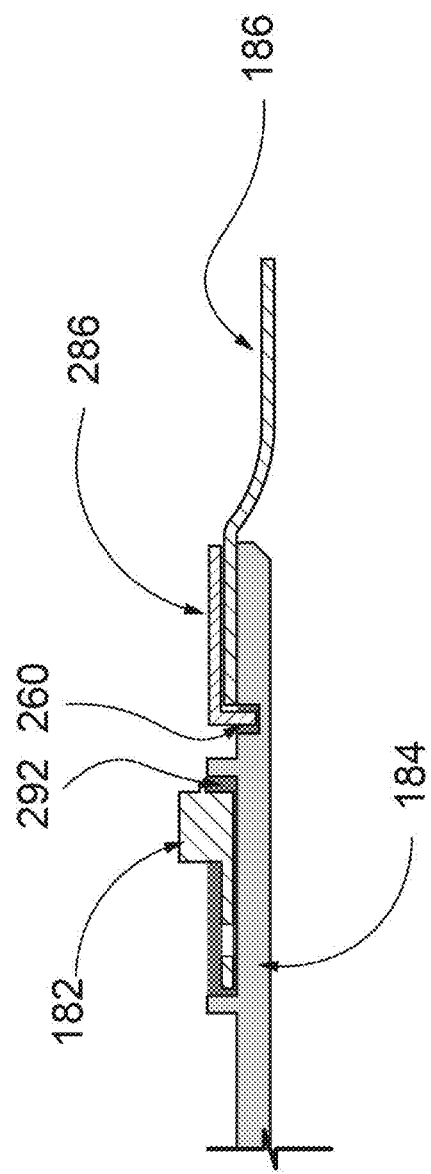

FIG. 36 is a view similar to FIG. 35 but showing an adhesive attachment for the thermistor and an adhesively bonded retainer for the flexible frame.

Figure 37:
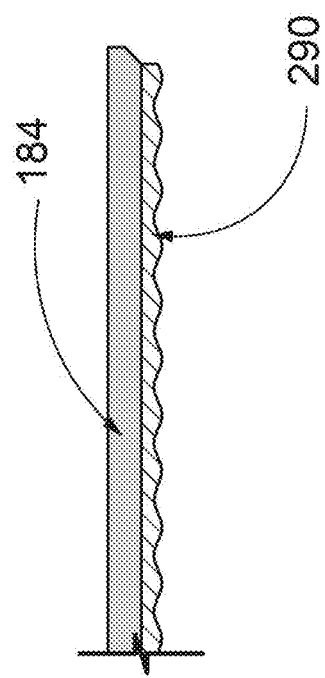

FIG. 37 is a cross-sectional view showing a thermally conductive layer on the user side of the tile for user comfort.

Figure 38:
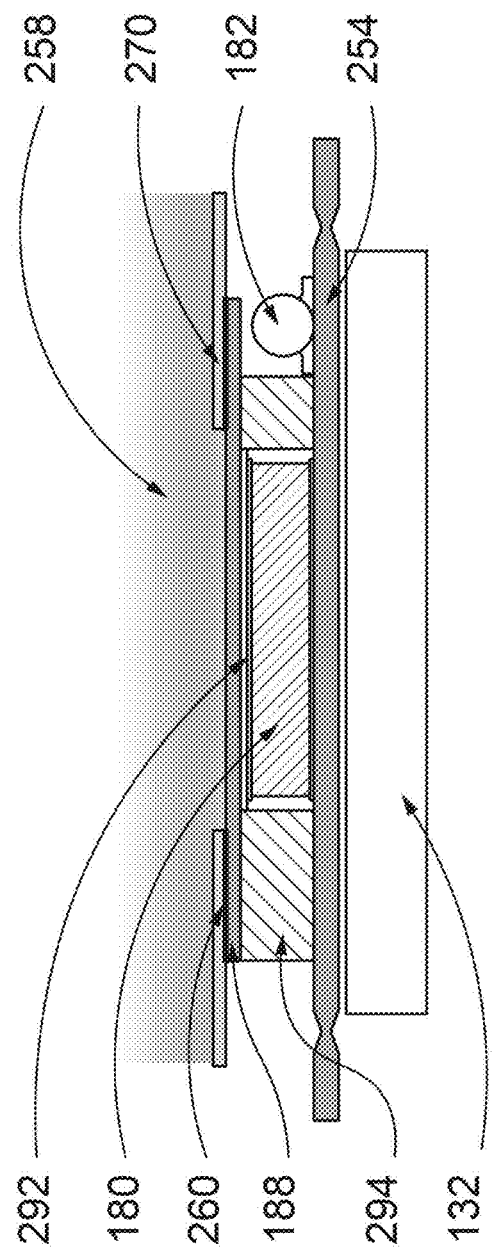

FIG. 38 is a cross-sectional view of a portion of a HEM assembly of the disclosure and having a segmented tile and a conductive platform adhesive bonded to a flexible sheet.

Figure 39:
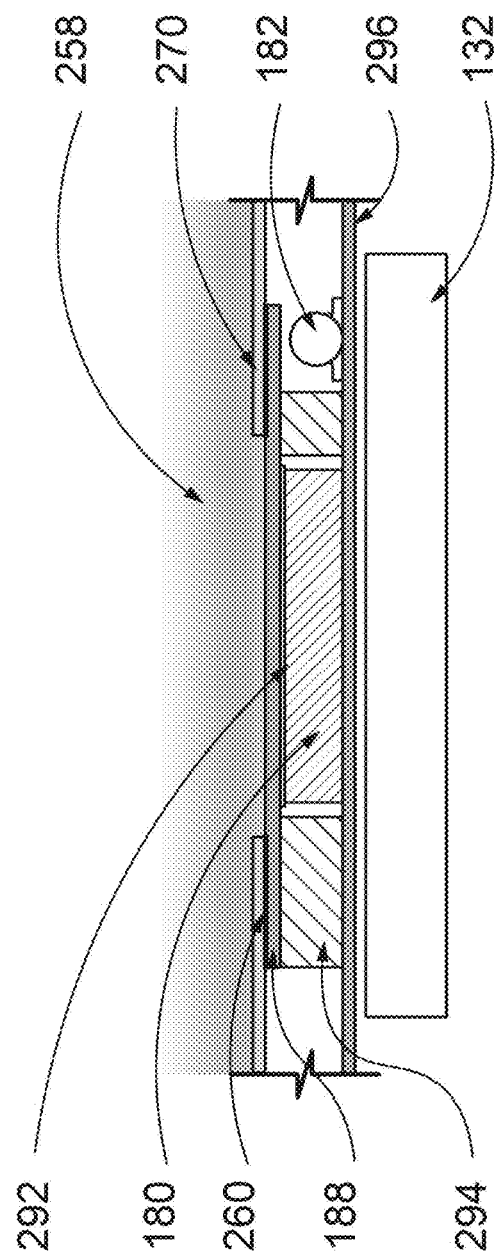

FIG. 39 is a cross-sectional view of a portion of a HEM assembly having a flexible thermally conductive material instead of a tile.

FIG. 40 is a cross-sectional view of a portion of a HEM assembly using adhesive attachment for the TEC and a plate embedded between two layers of flexible sheet.

Figure 41:
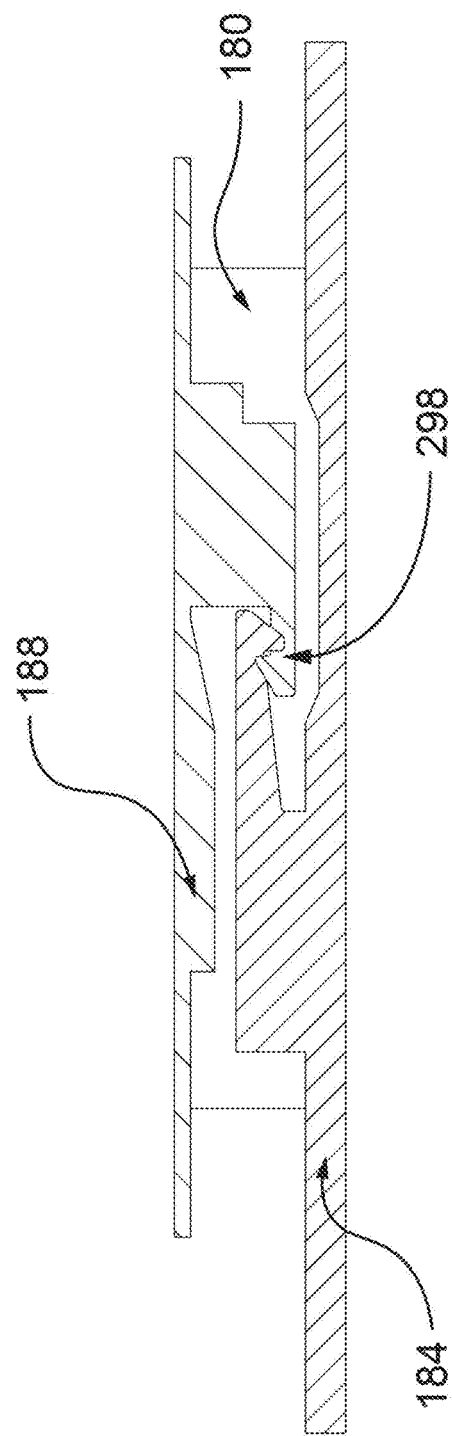

FIG. 41 is a cross-sectional view of a portion of a HEM assembly having a horizontal snap attachment.

Figure 42:
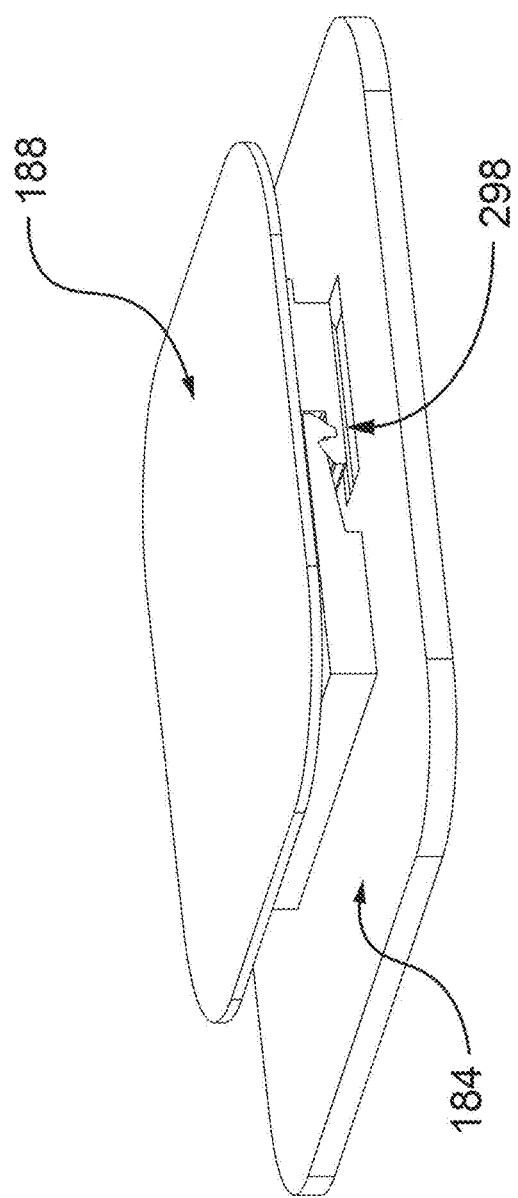

FIG. 42 is a top perspective view of the assembly of FIG. 41.

Figure 43:
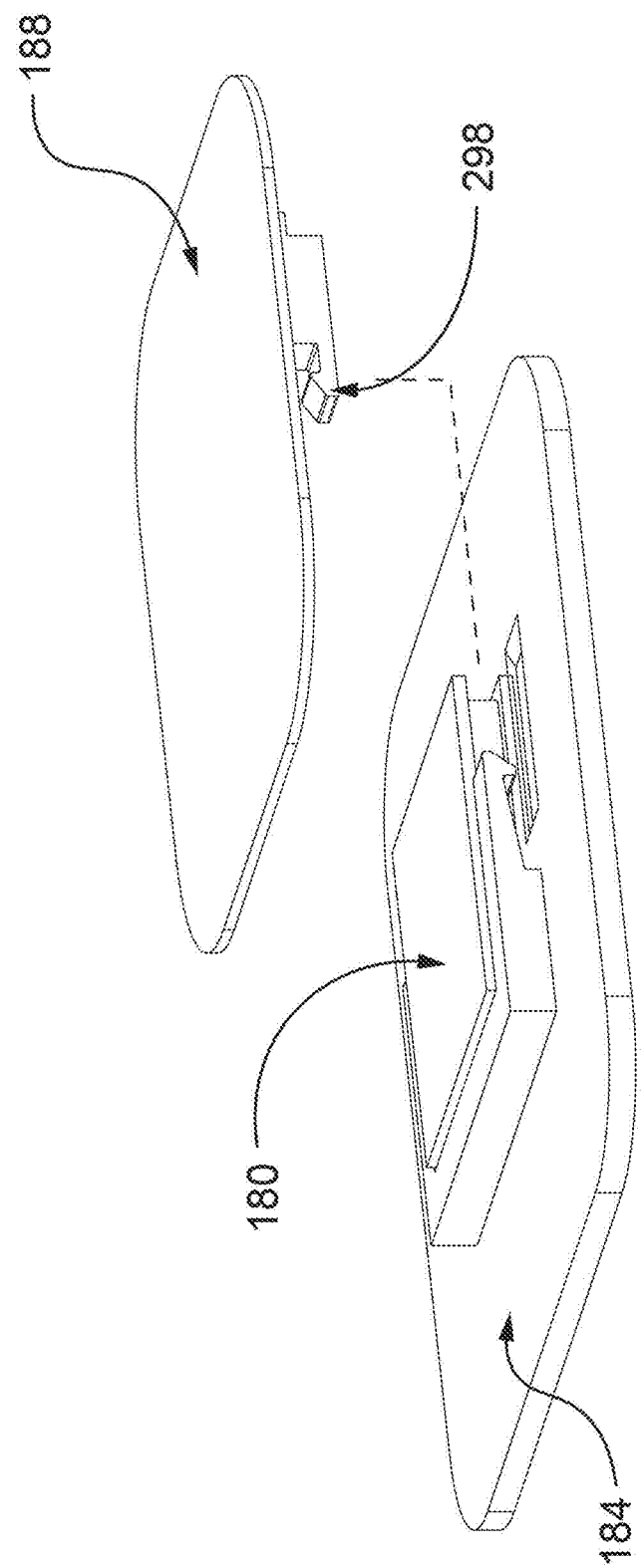

FIG. 43 is an exploded perspective view of the assembly of FIG. 42.

Figure 44:
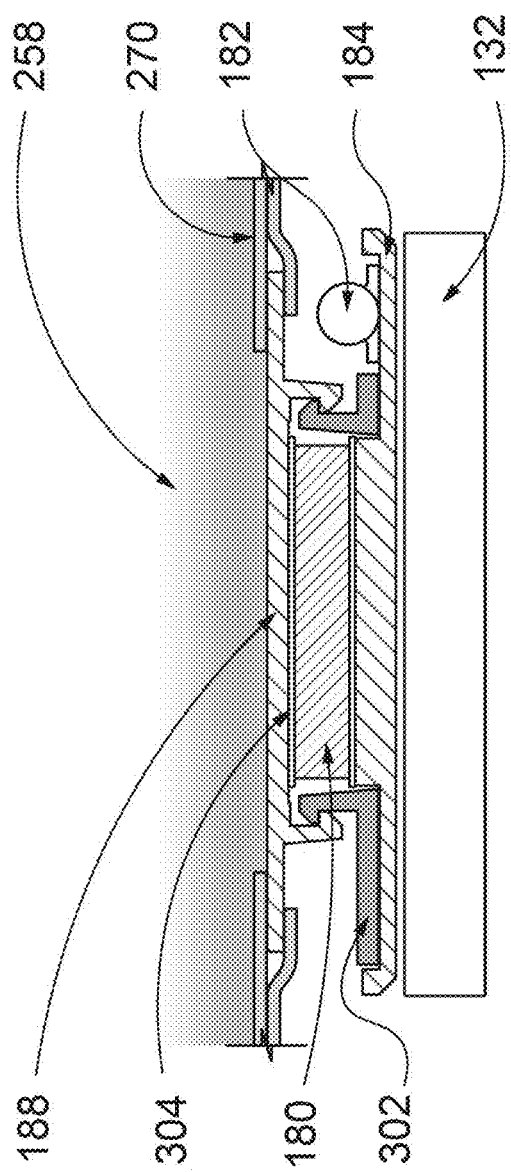

FIG. 44 is a cross-sectional view of a portion of a HEM assembly having a vertical snap attachment.

Figure 45:
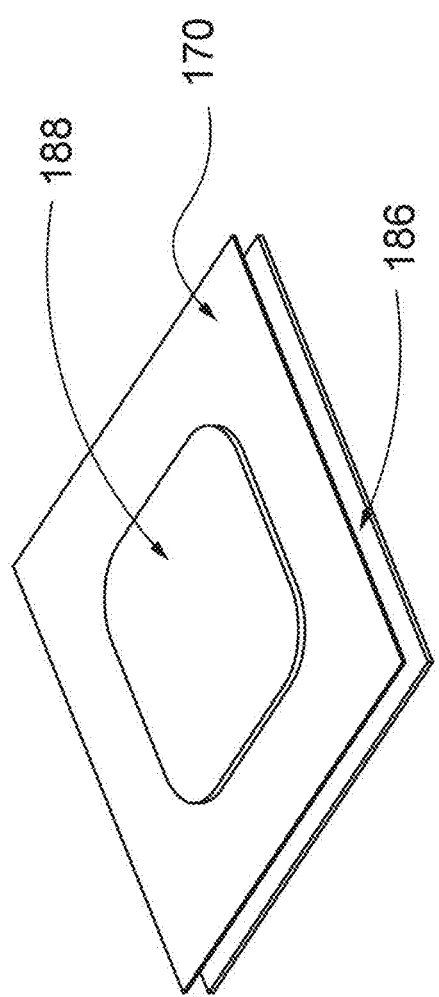

FIG. 45 is a top perspective view of the assembly of FIG. 44.

Figure 46:
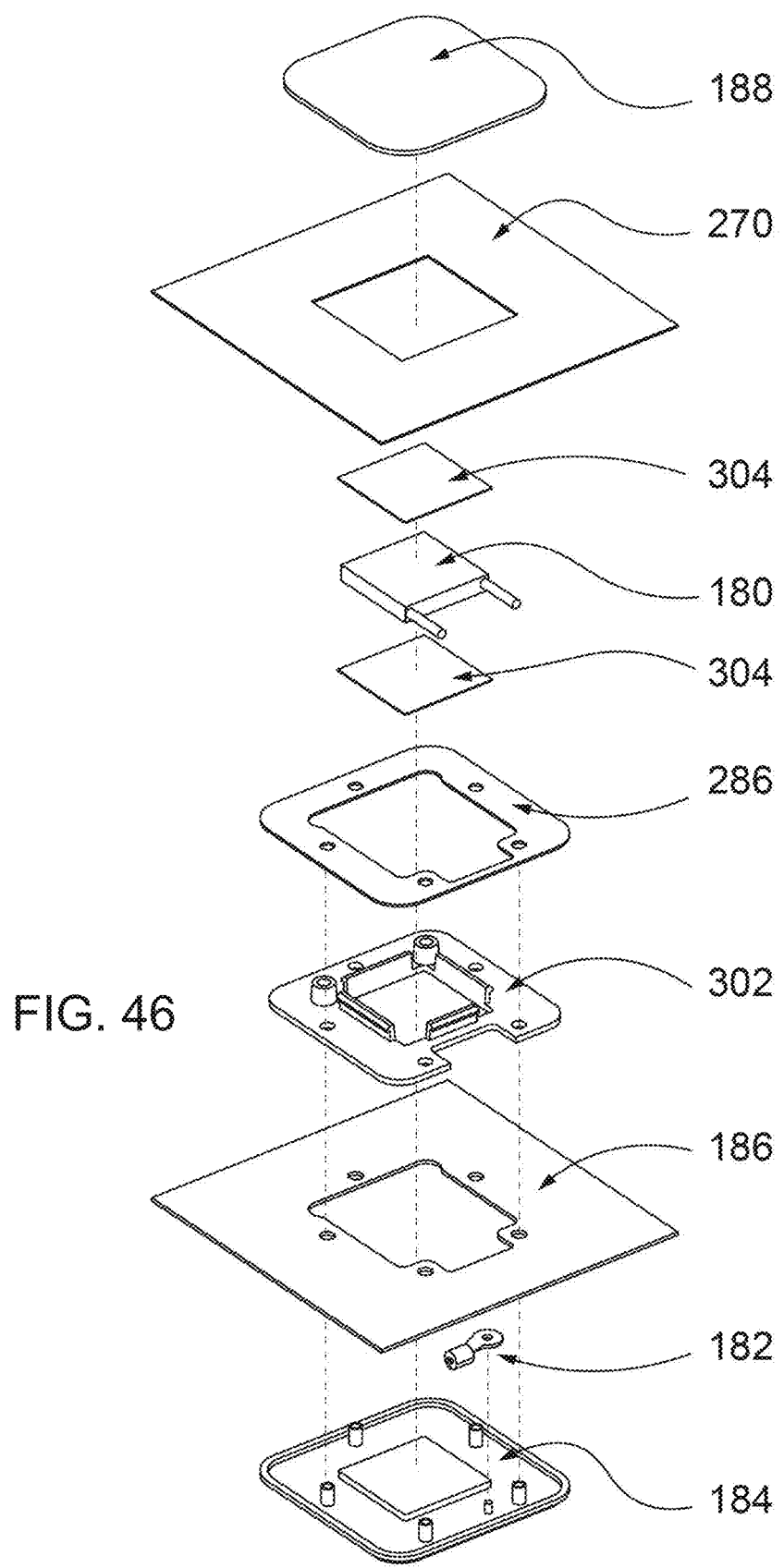

FIG. 46 is an exploded perspective view of the assembly of FIG. 45.

Figure 47:
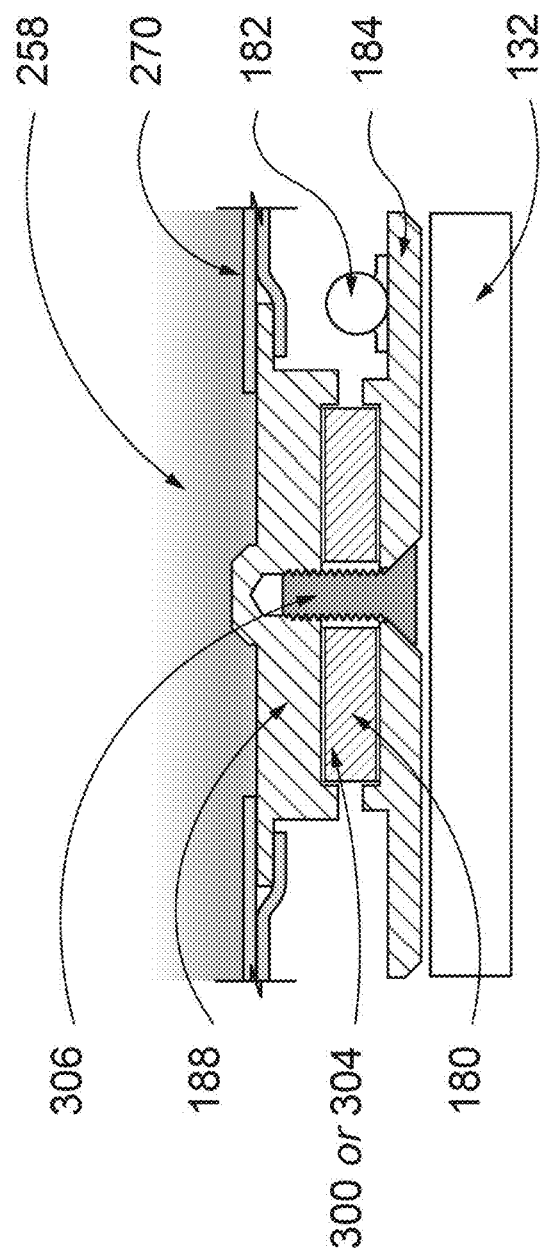

FIG. 47 is a cross-sectional view of a portion of a HEM assembly having a non-thermally conductive screw attachment.

Figure 48:
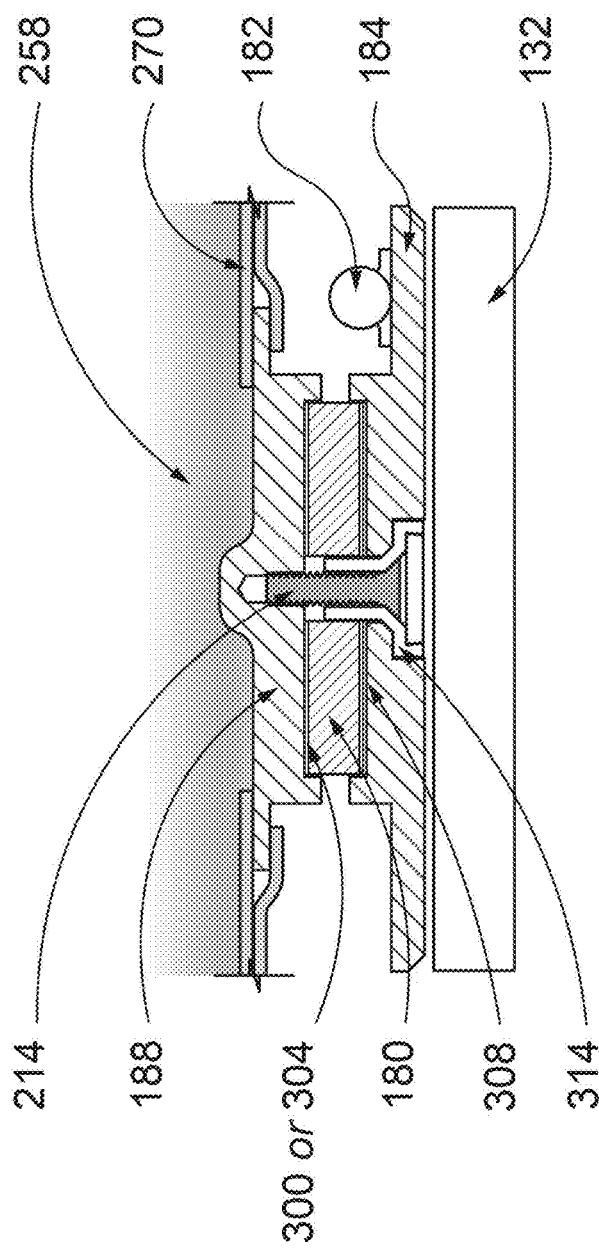

FIG. 48 is a cross-sectional view of a portion of a HEM assembly having an insulated screw attachment.

Figure 49:
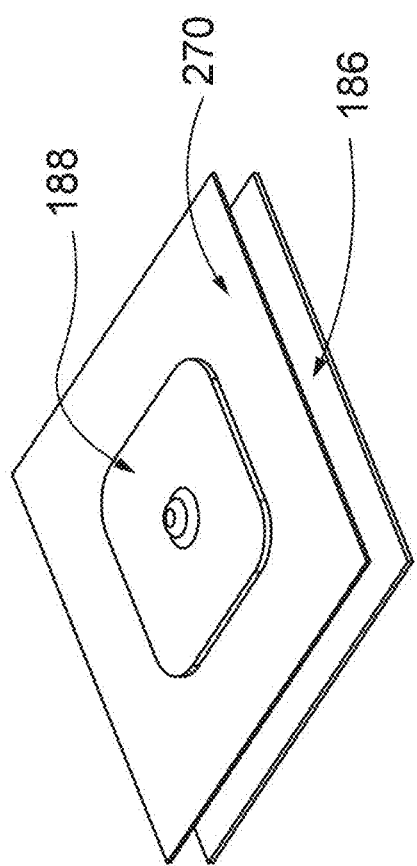

FIG. 49 is a top perspective view of the assembly of FIG. 48.

Figure 50:
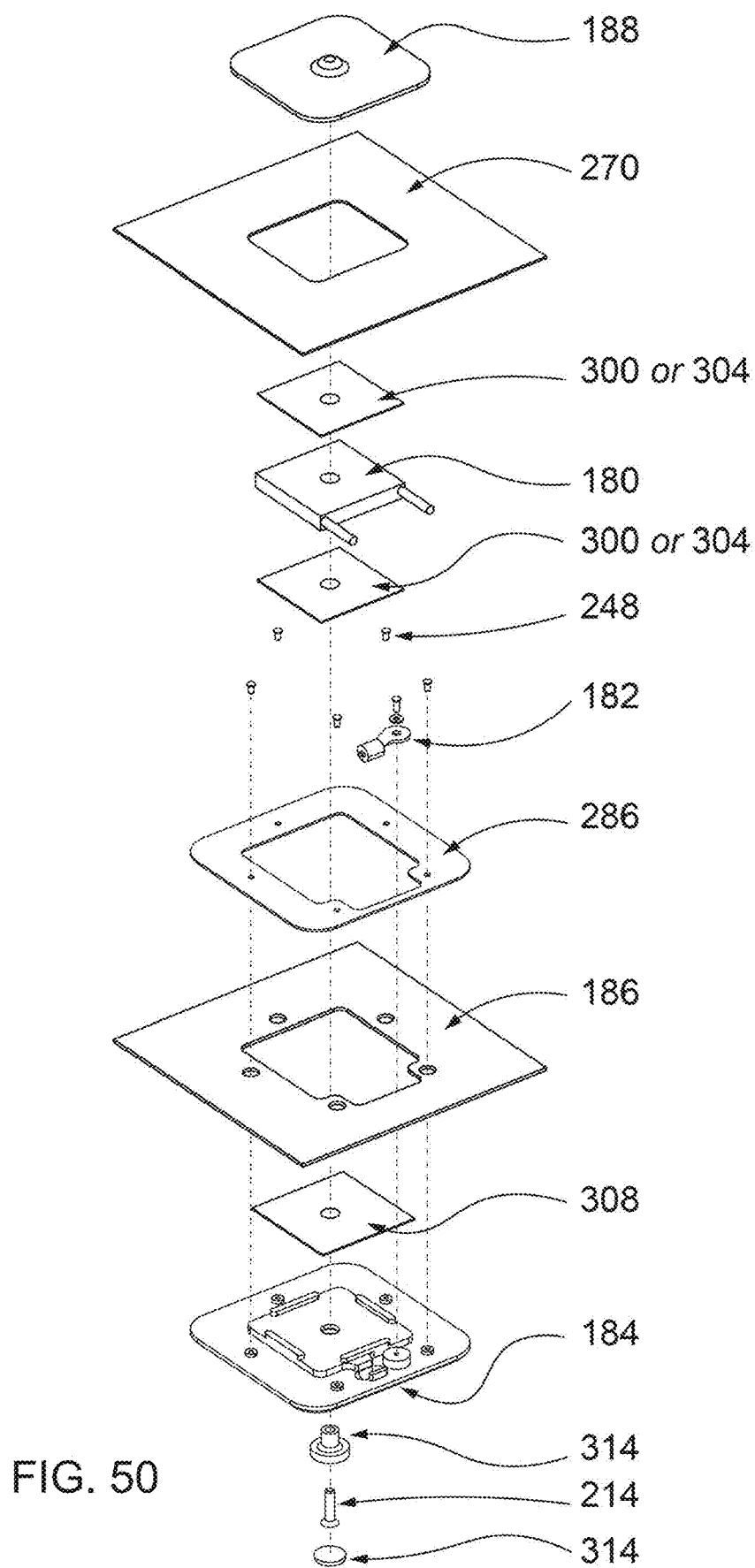

FIG. 50 is an exploded perspective view of the assembly of FIG. 48.

Figure 51:
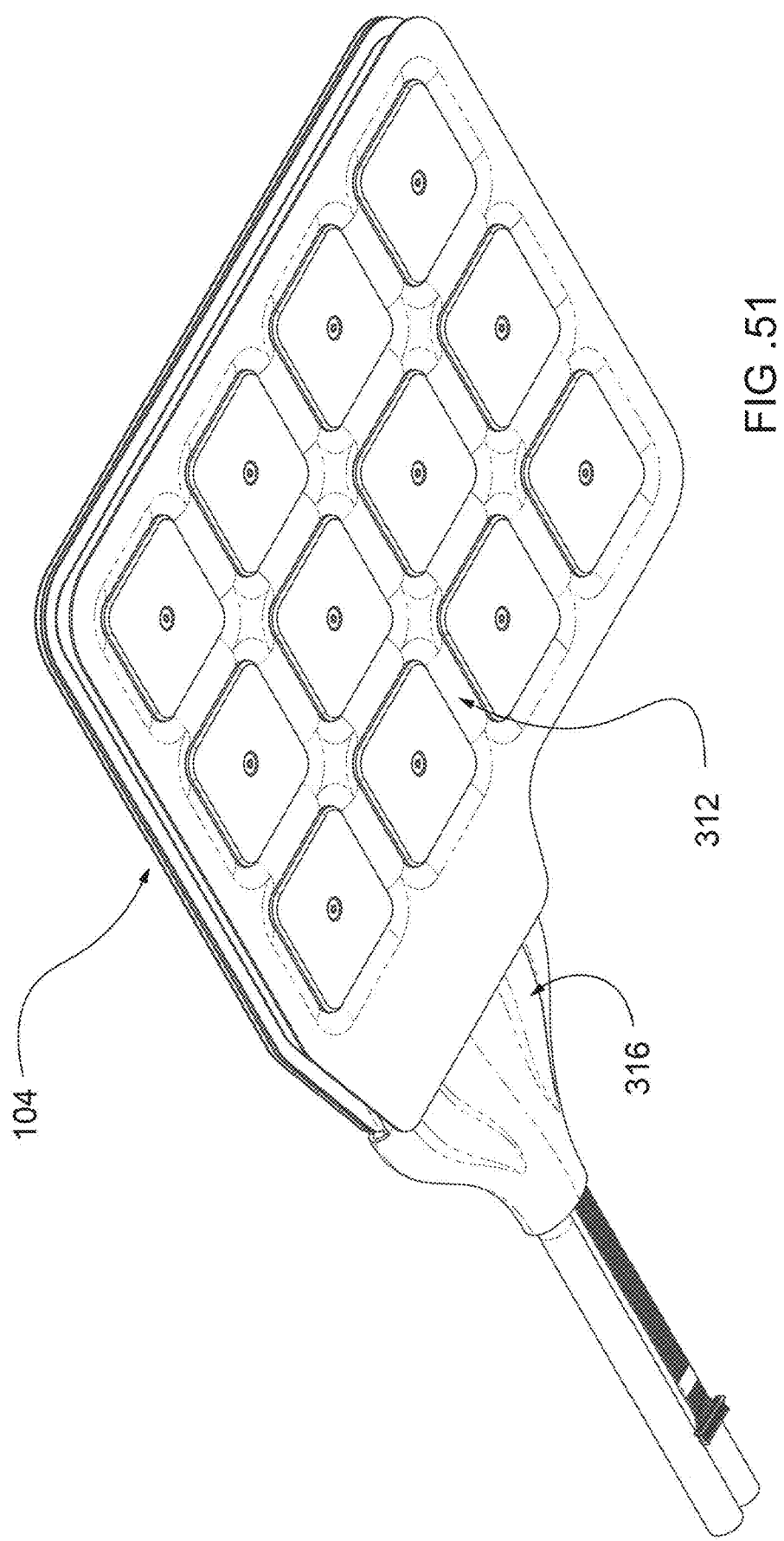

FIG. 51 is a bottom perspective view of a HEM assembly of the present disclosure having a screw attachment (such as shown in FIG. 47).

Figure 52:
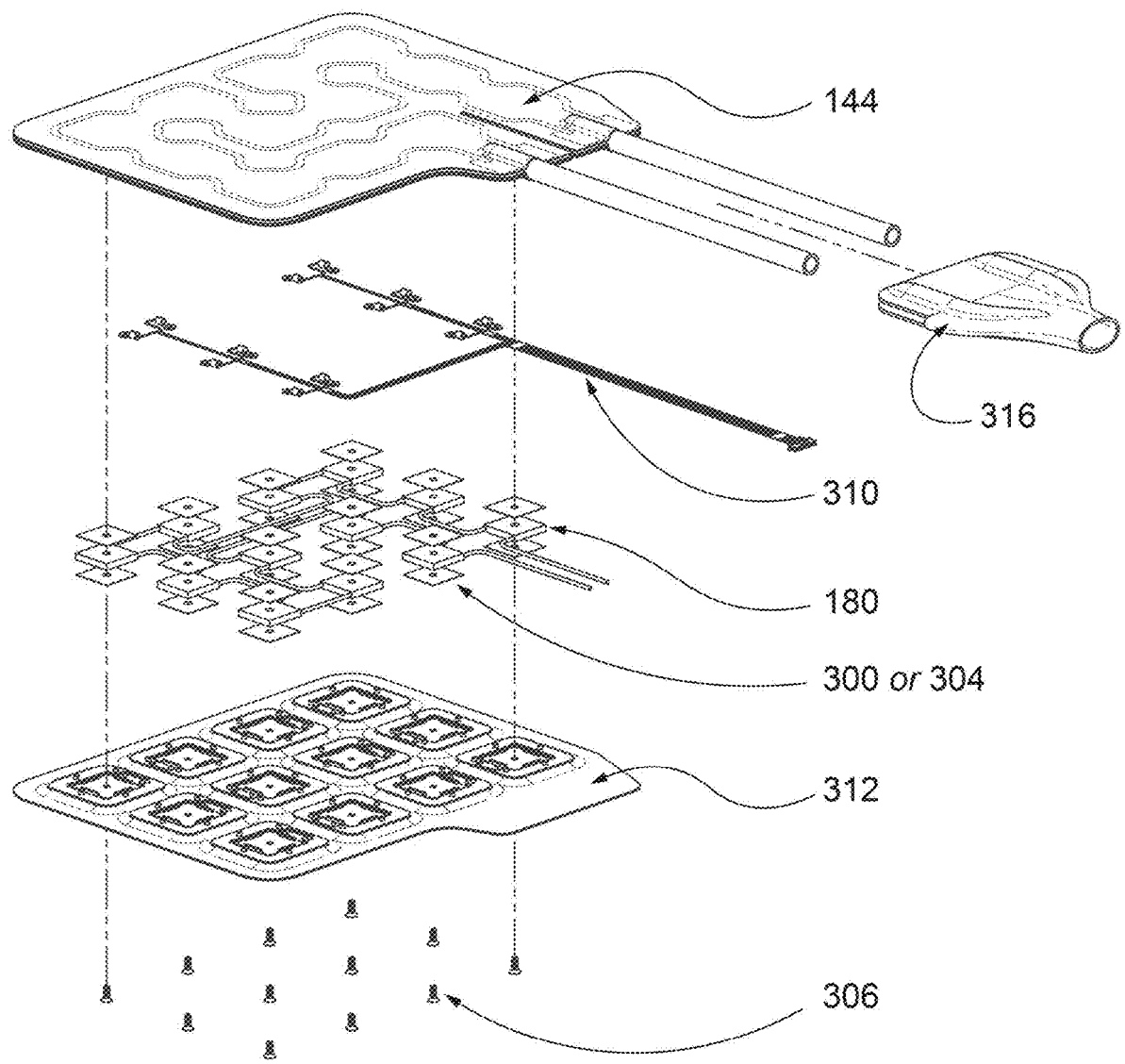

FIG. 52 is an exploded perspective view of the HEM assembly of FIG. 51.

Figure 53:
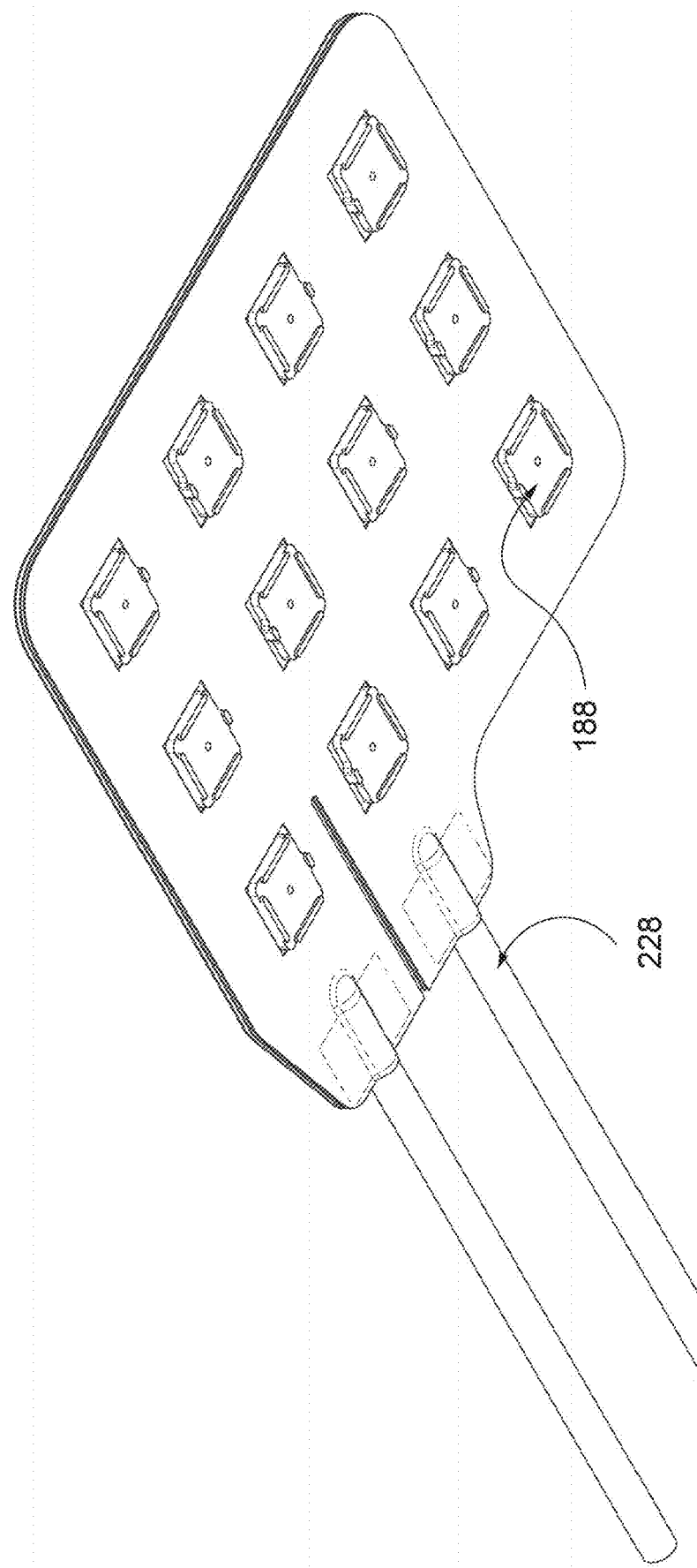

FIG. 53 is a bottom perspective view of the fluid channel assembly of the HEM assembly of FIGS. 51 and 52

Figure 54:
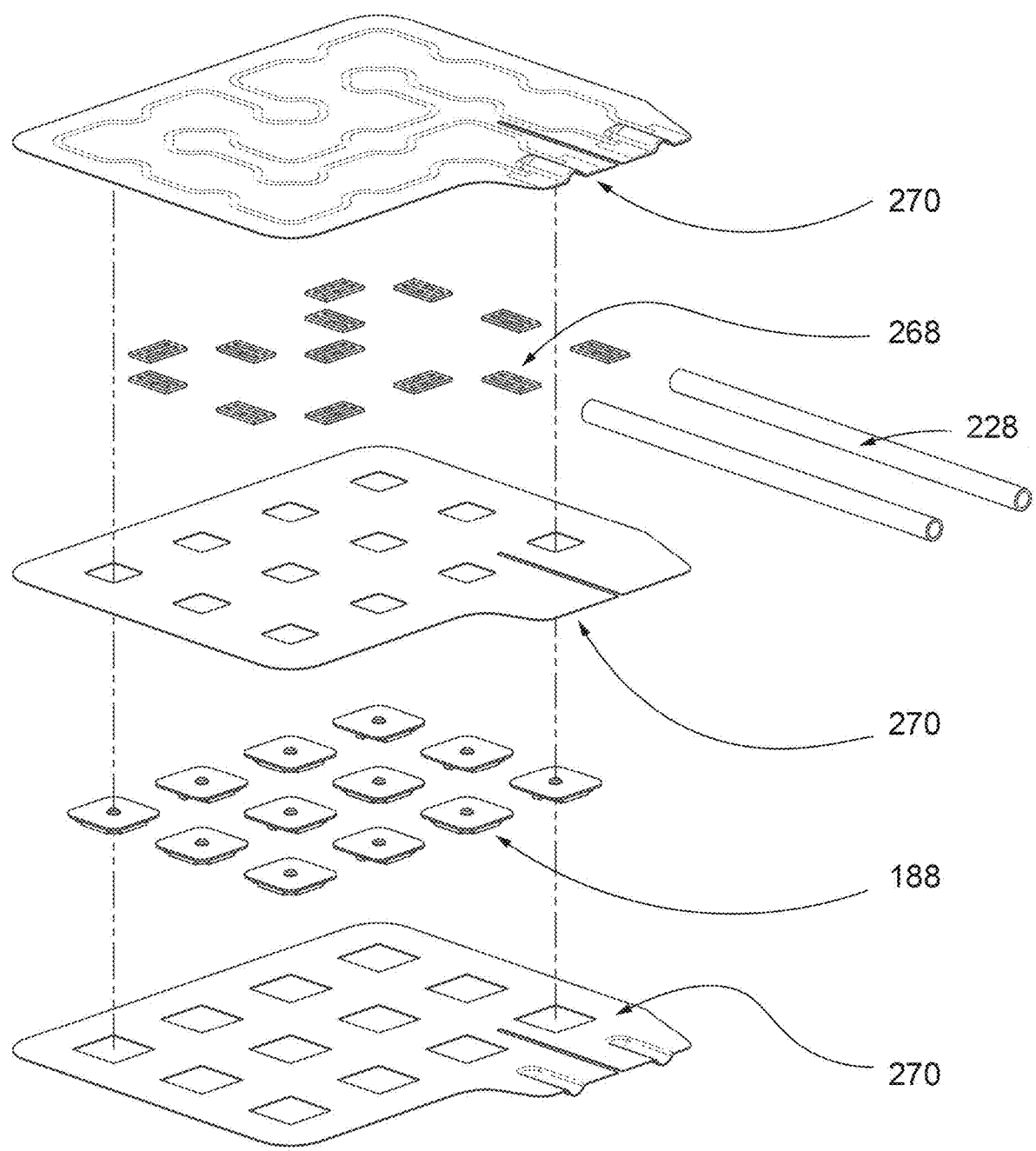

FIG. 54 is an exploded perspective view of the fluid channel assembly of FIG. 53.

Figure 55:
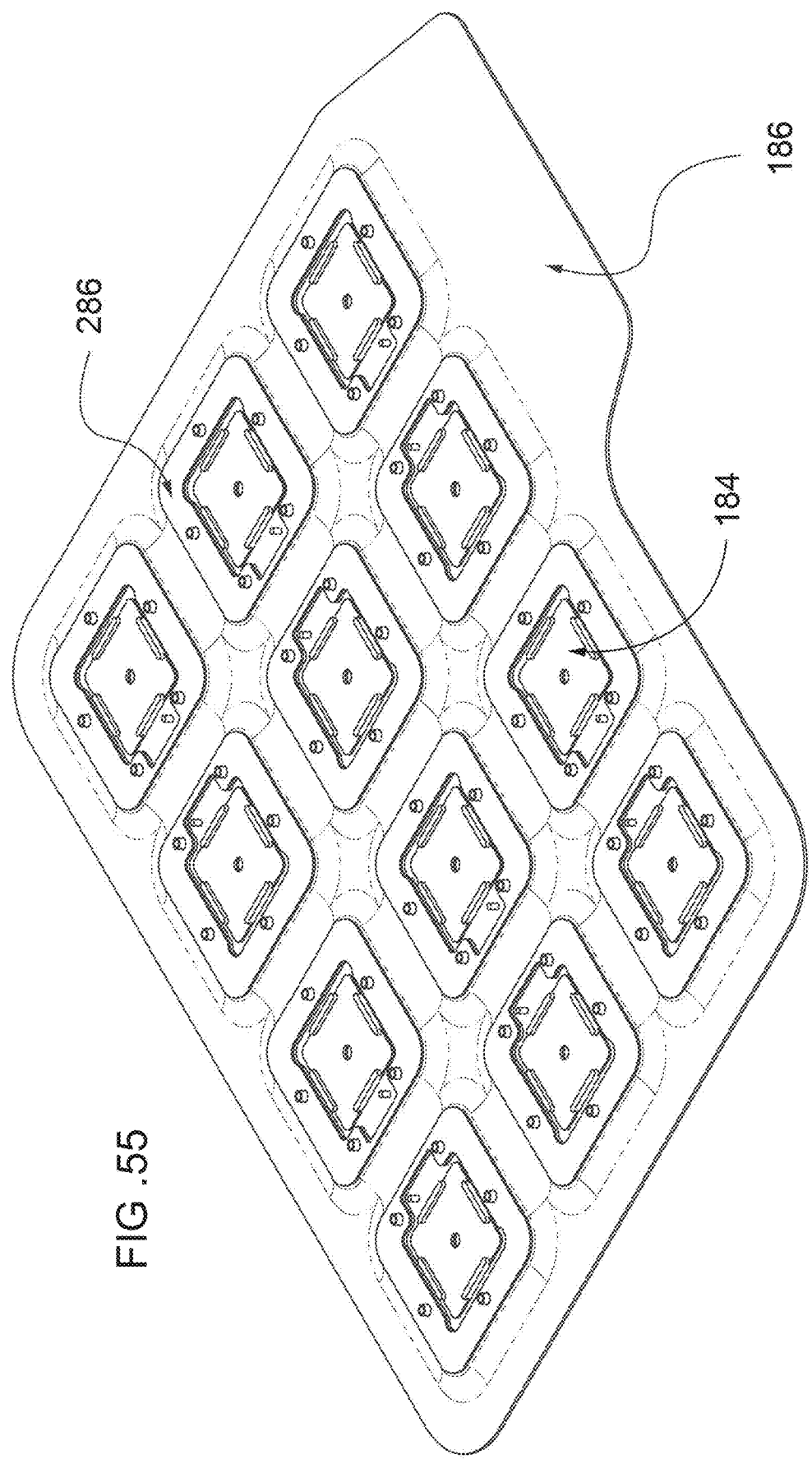

FIG. 55 is a top perspective view of the flexible frame and tile assembly of FIG. 52.

Figure 56:
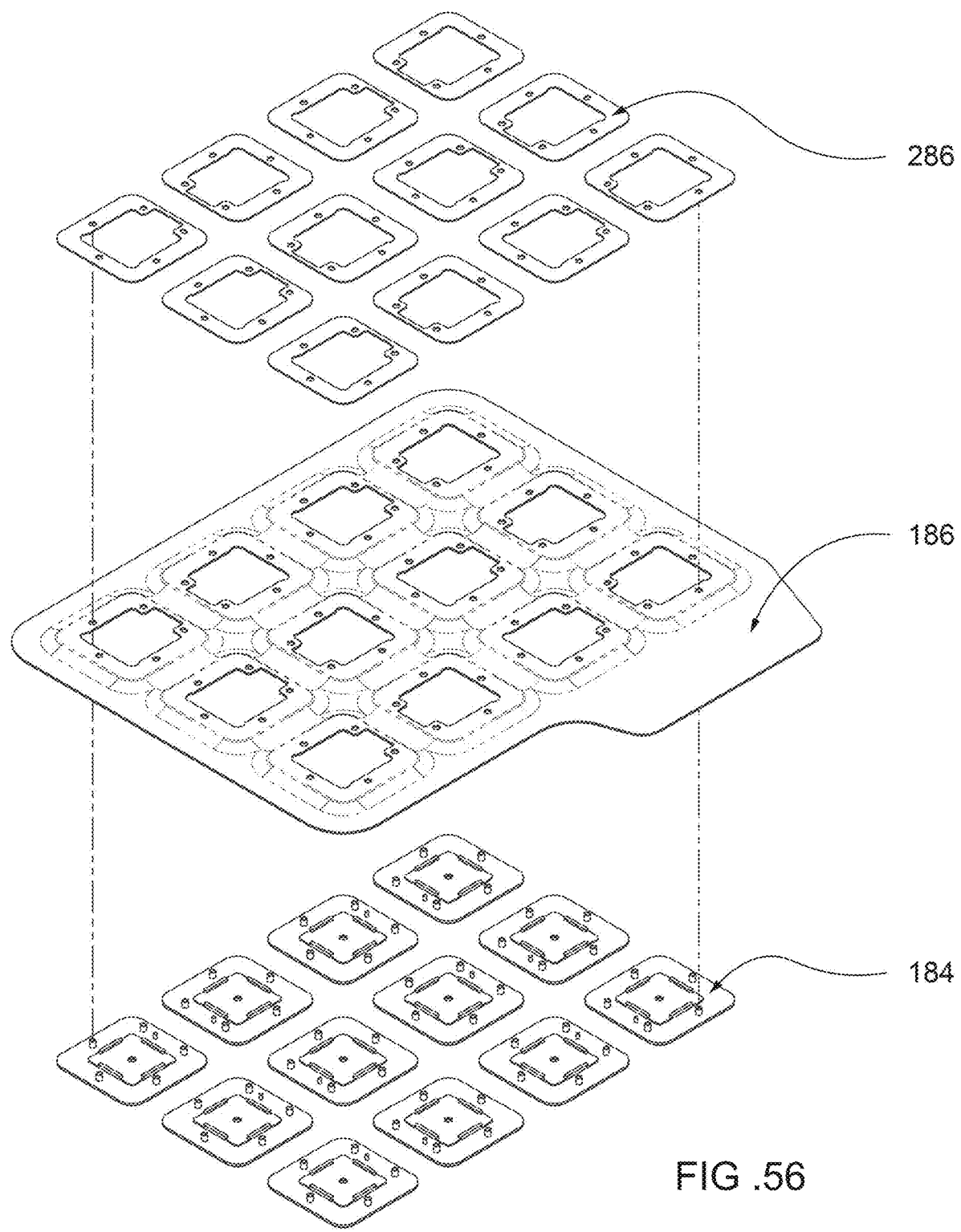

FIG. 56 is an exploded perspective view of the frame and tile assembly of FIG. 55.

Figure 57:
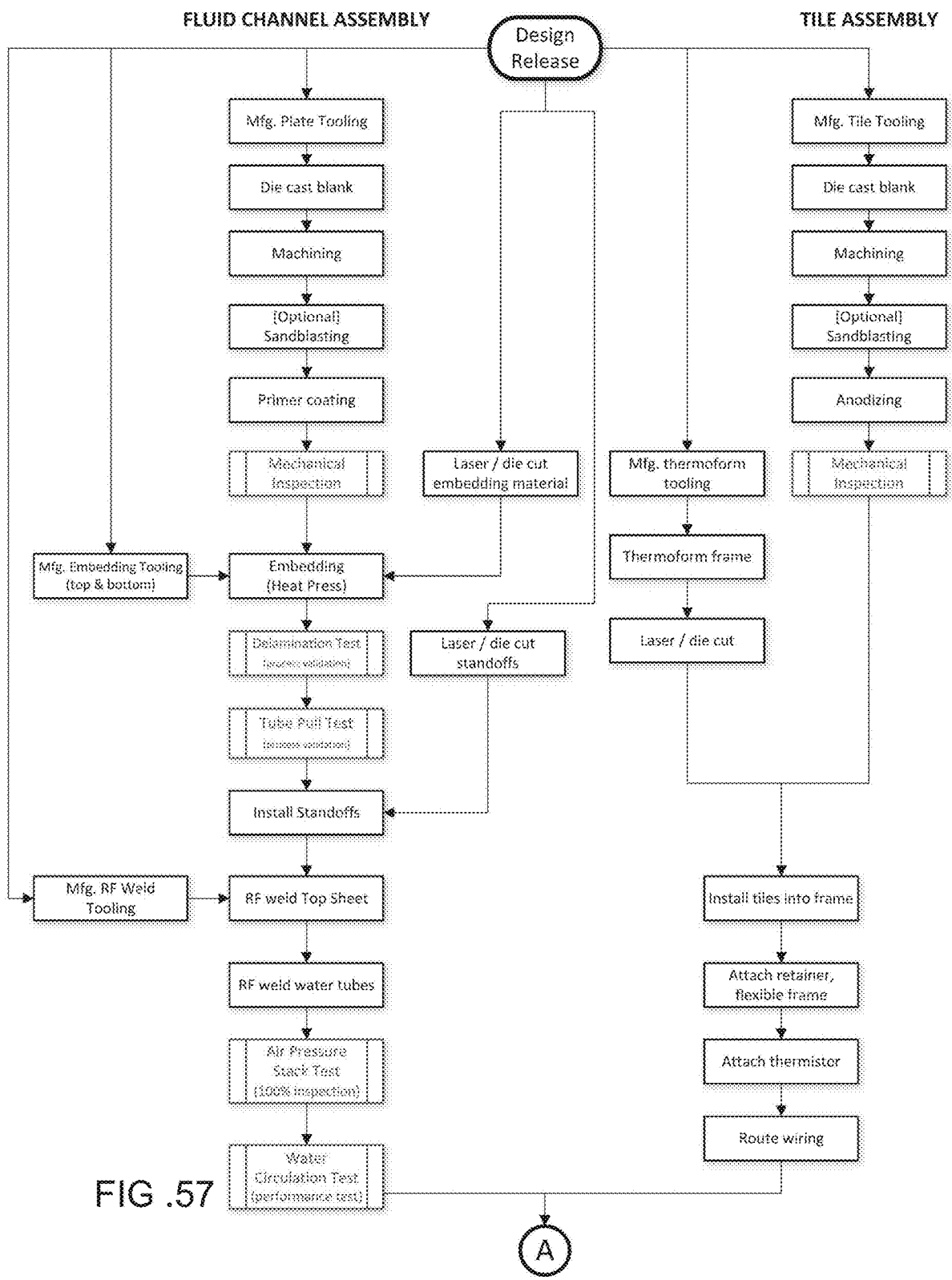

FIG. 57 is a flow chart for assembling a HEM assembly of the disclosure.

Figure 58:
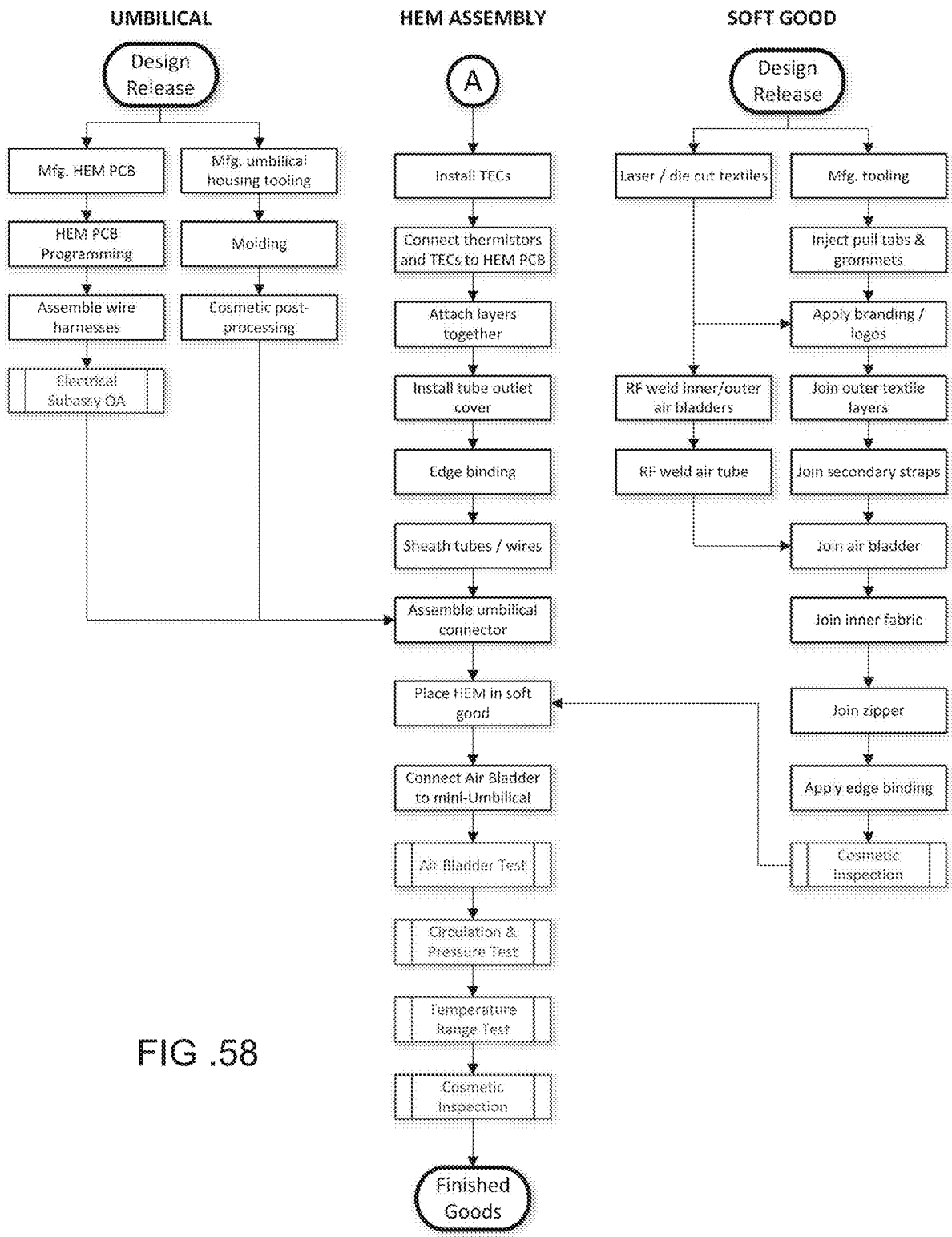

FIG. 58 is a flow chart for assembling a HEM assembly which includes the HEM from FIG. 57.

FIG. 58 is a schematic of a method of producing a soft good of the disclosure.

FIG. 59 is a diagram of several shapes of HEM tiles of the disclosure.

Figure 60:
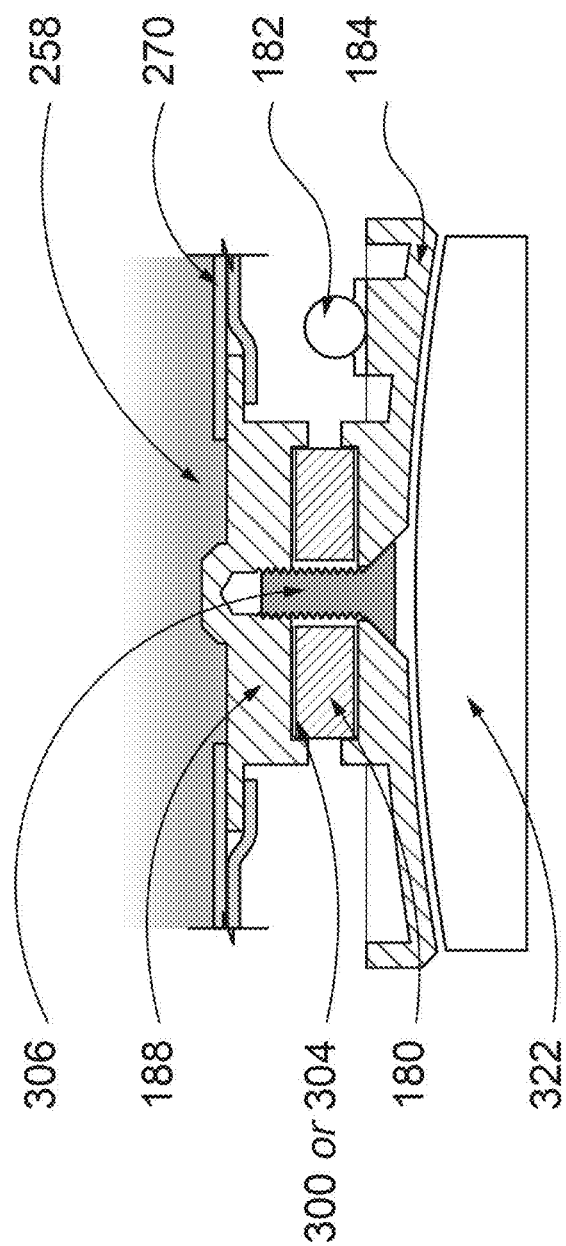

FIG. 60 is a cross section of a curved tile using a non-thermally conductive screw assembly method.

Figure 61:
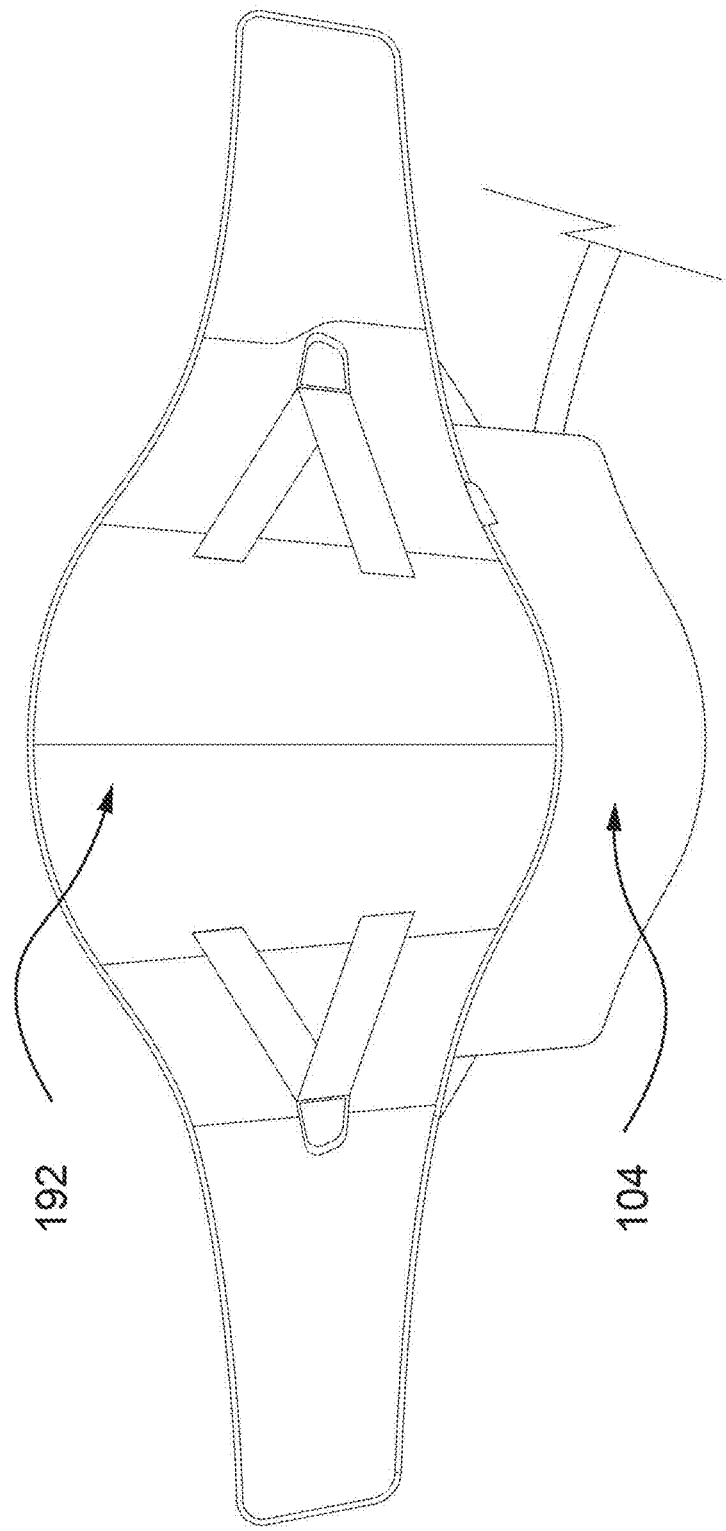

FIG. 61 is a diagram of an HEM of the disclosure inserted into a soft good for a back.

Figure 62:
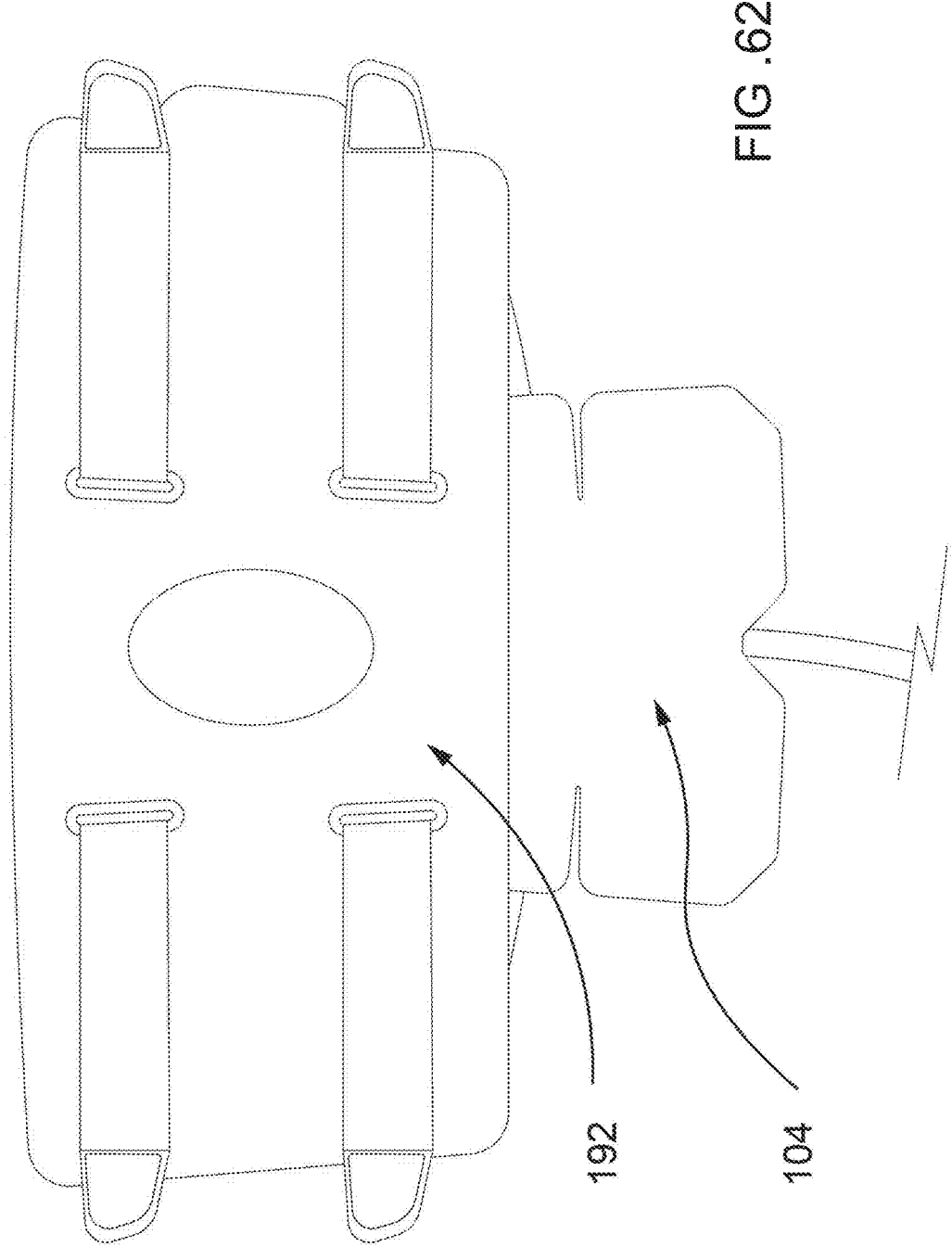

FIG. 62 is a diagram of an HEM of the disclosure inserted into a soft good for a knee.

Figure 63:
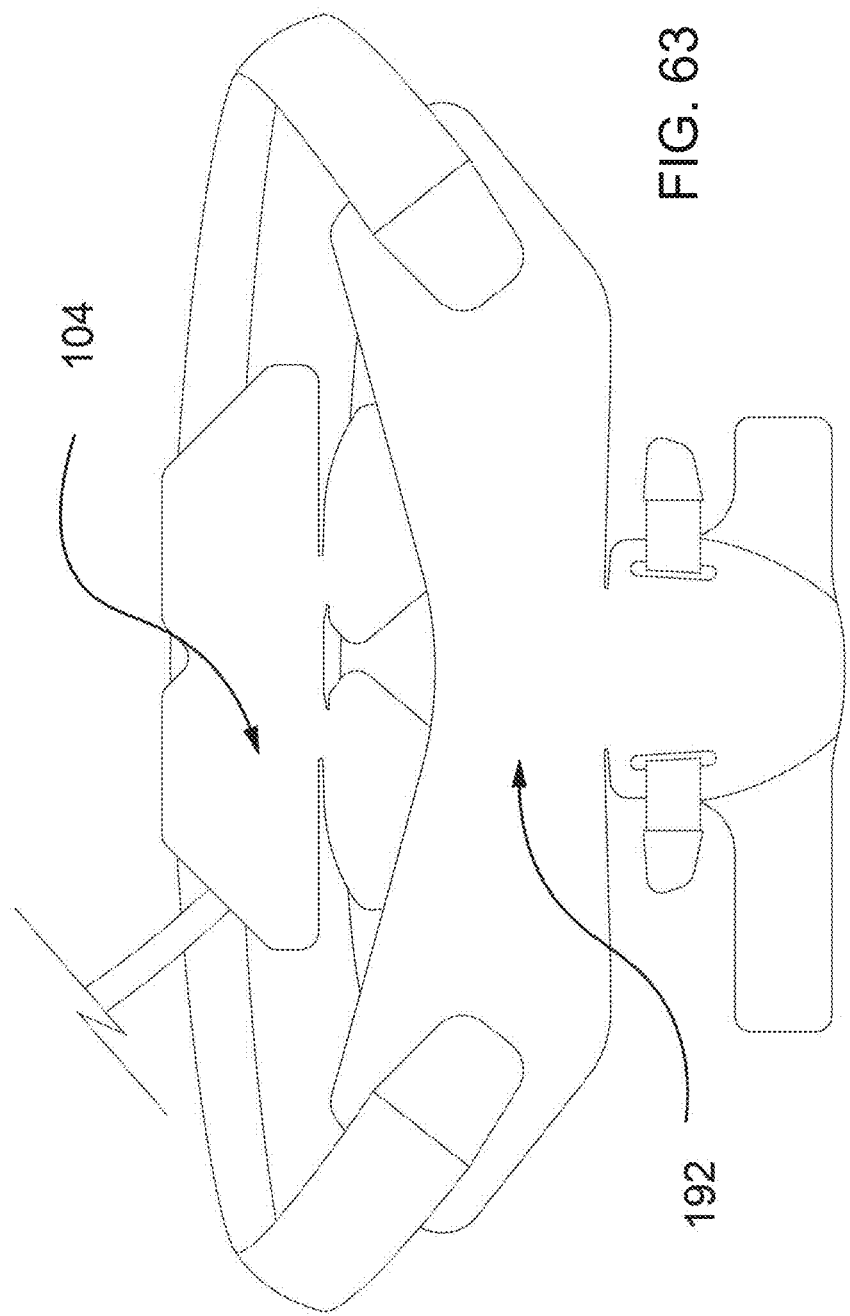

FIG. 63 is a diagram of an HEM of the disclosure inserted into a soft good for a shoulder.

FIG. 64 is a diagram of an HEM of the disclosure inserted into a soft good for an ankle.

FIG. 65 is a diagram of an HEM of the disclosure inserted into a utility pad soft good.

FIG. 66 is a diagram of an air bladder of the disclosure inserted into a soft good of the disclosure.

FIG. 67 is an exploded perspective view of an HEM assembly of the disclosure which has the air bladder contained within the HEM.

FIG. 68A-i illustrates several diagrams of an HEM of the disclosure inserted and utilized in soft good bodysuits of the disclosure.

Figure 68A:
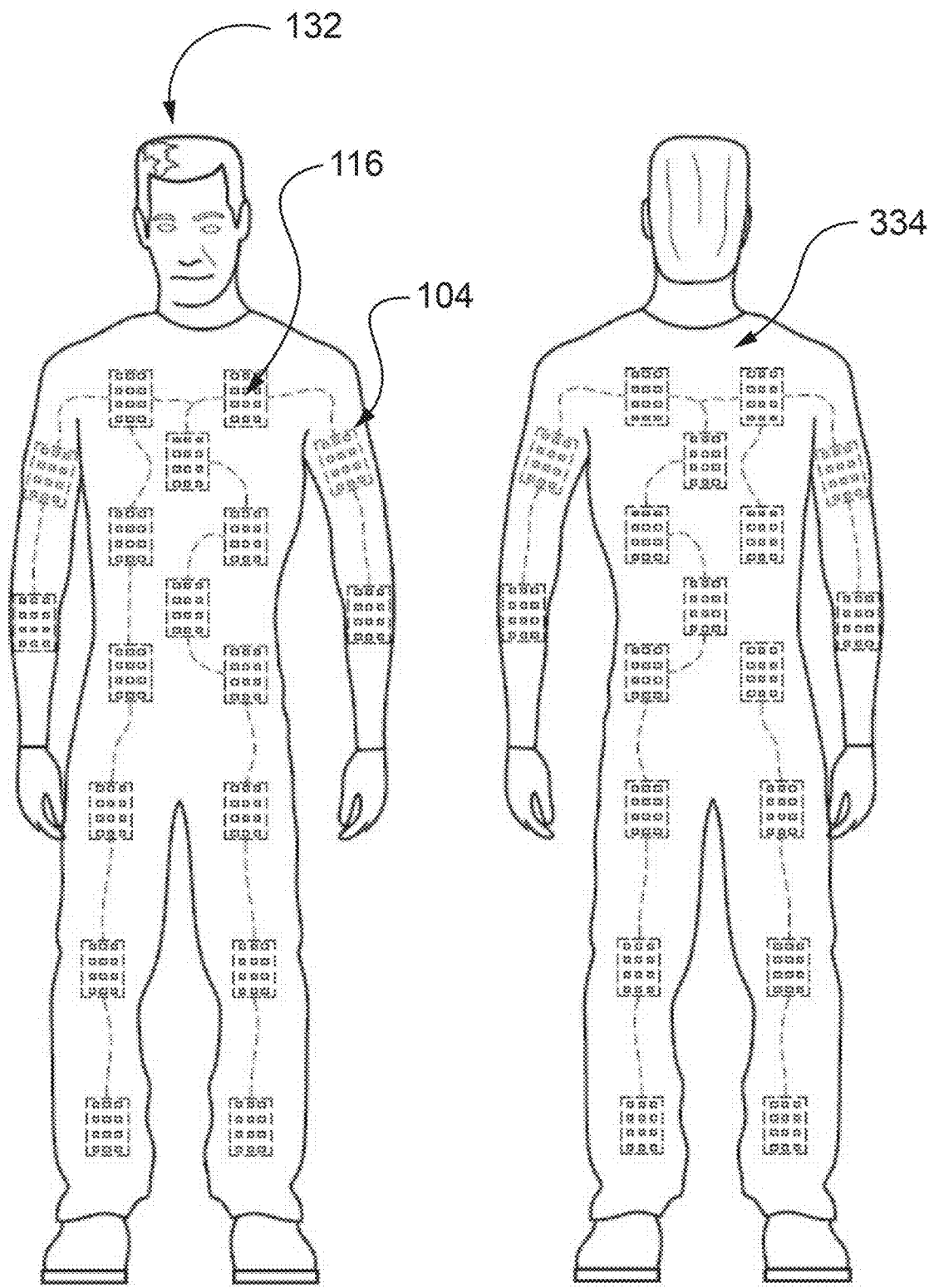

FIG. 68A illustrates a soft good comprising a thermally controlled suit.

FIG. 68B illustrates a soft good which is integrated with a CPU console.

Figure 68C:
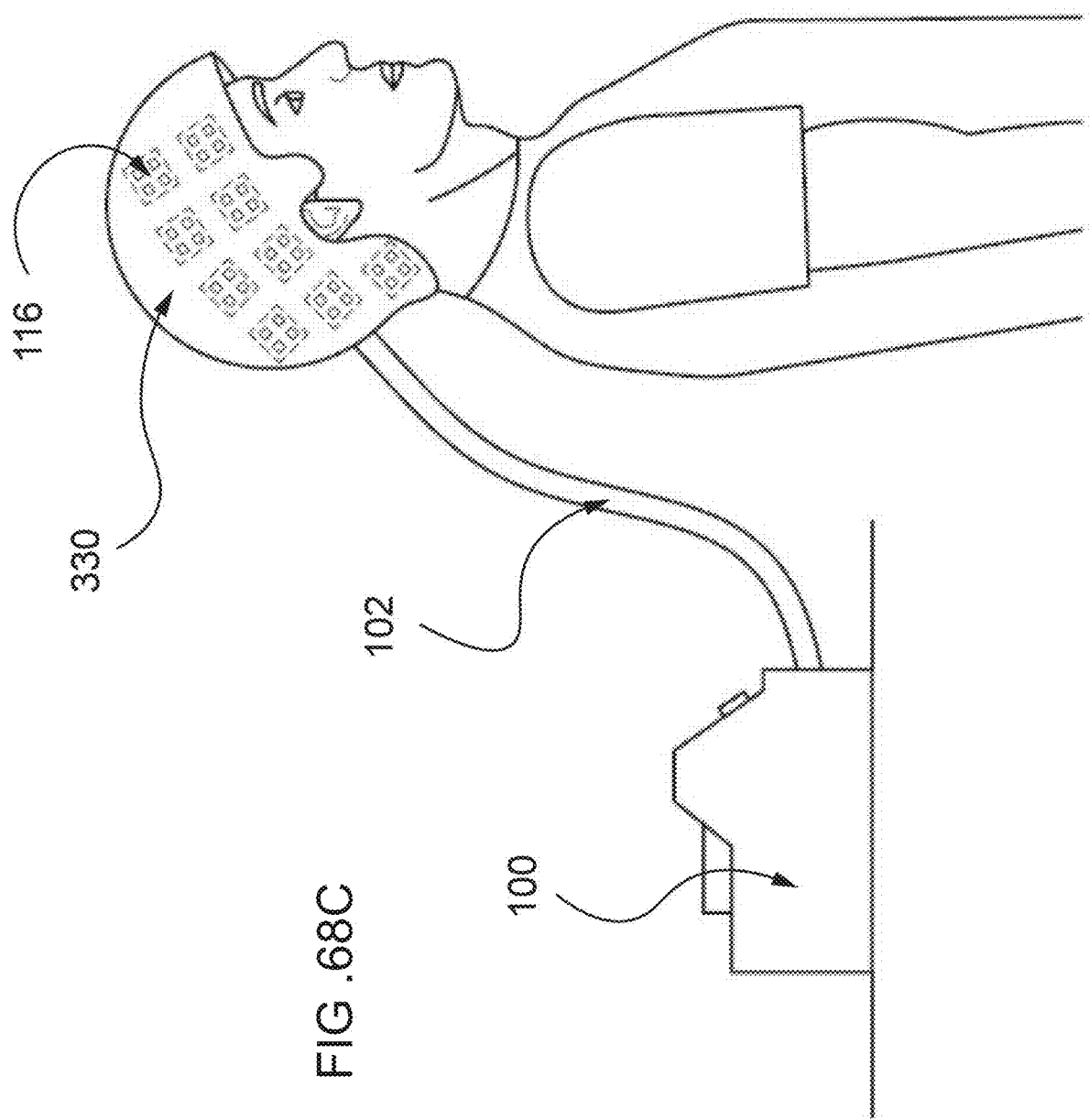

FIG. 68C illustrates a soft good utilized as a helmet or headwear.

Figure 68D:
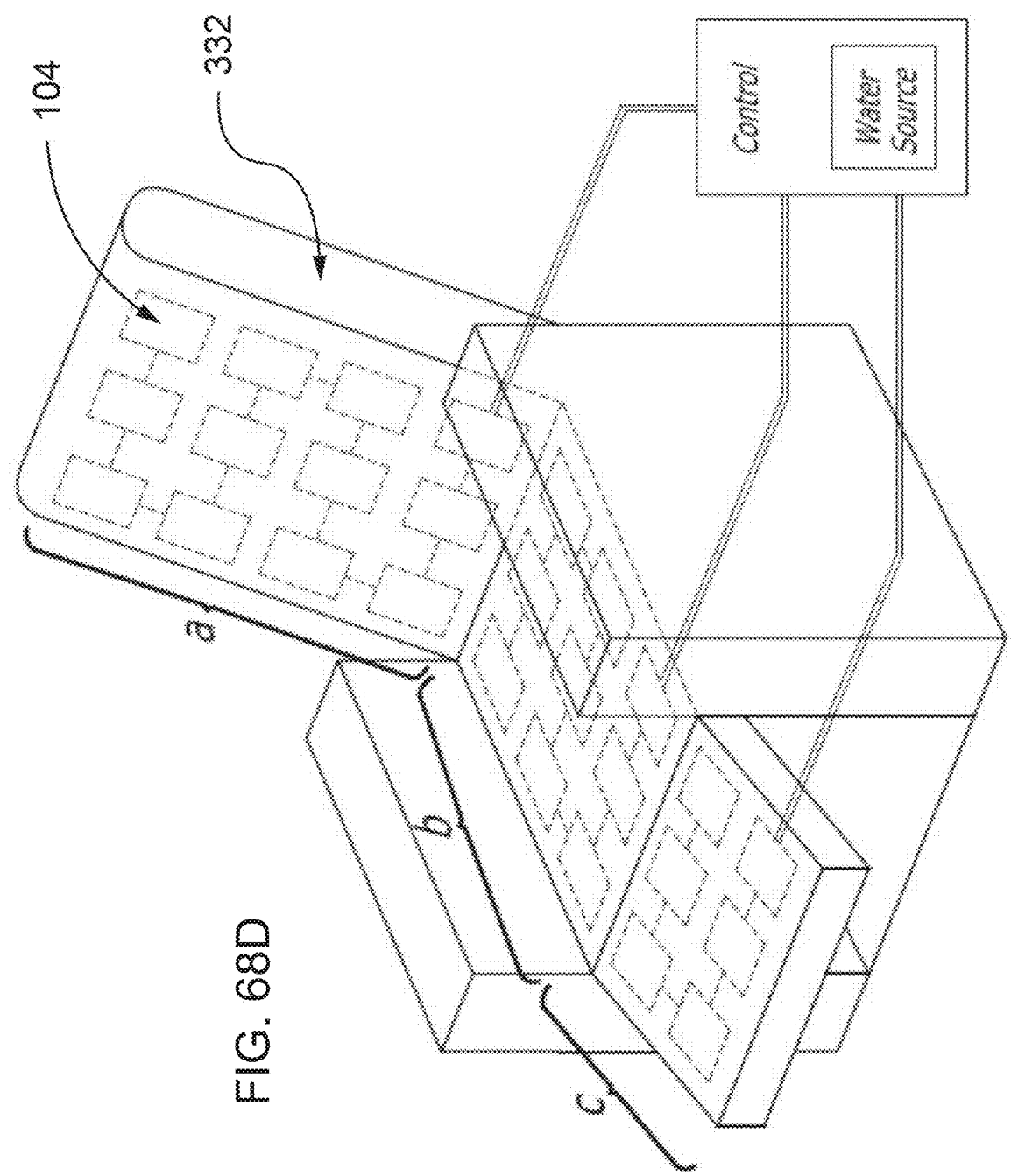

FIG. 68D illustrates a soft good utilized in furniture.

FIG. 68E illustrates a soft good utilized in an automobile seat.

FIG. 68F illustrates an embodiment utilized in an automobile providing data feedback.

FIG. 68G illustrates a soft good utilized in medical products (hospital bedding/surgical bedding, a neck brace, and a stretcher).

FIG. 68H shows an embodiment where temperature is differentially controlled on the body.

FIG. 68I shows an embodiment for gaming/virtual reality (VR) systems.

FIG. 69 is a diagram of a liquid container/vessel encased with a series of HEMs of the present disclosure.

Figure 70:
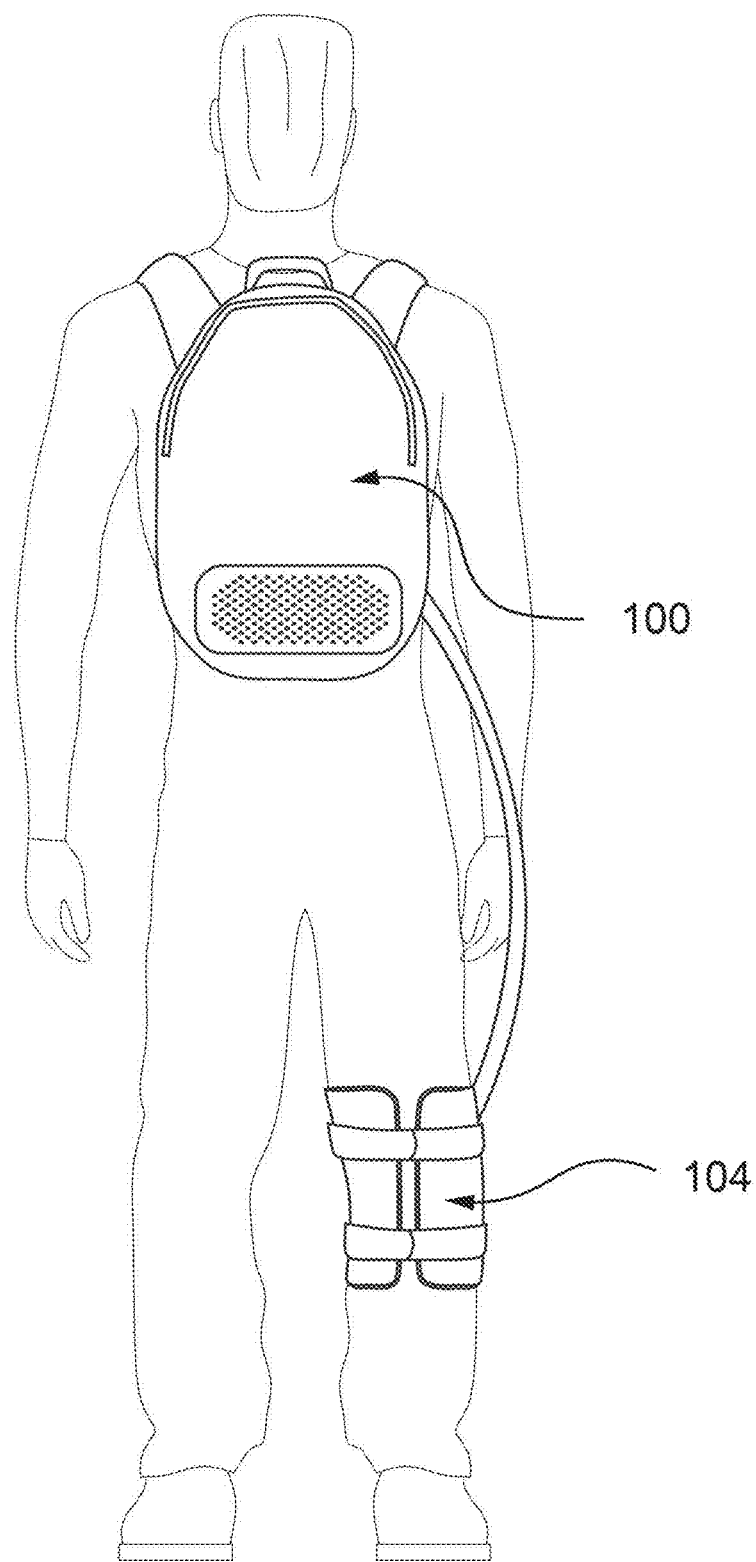

FIG. 70 shows an embodiment of the control unit contained in a soft good to optimize mobility.

DETAILED DESCRIPTION

Overview

Figure 1:
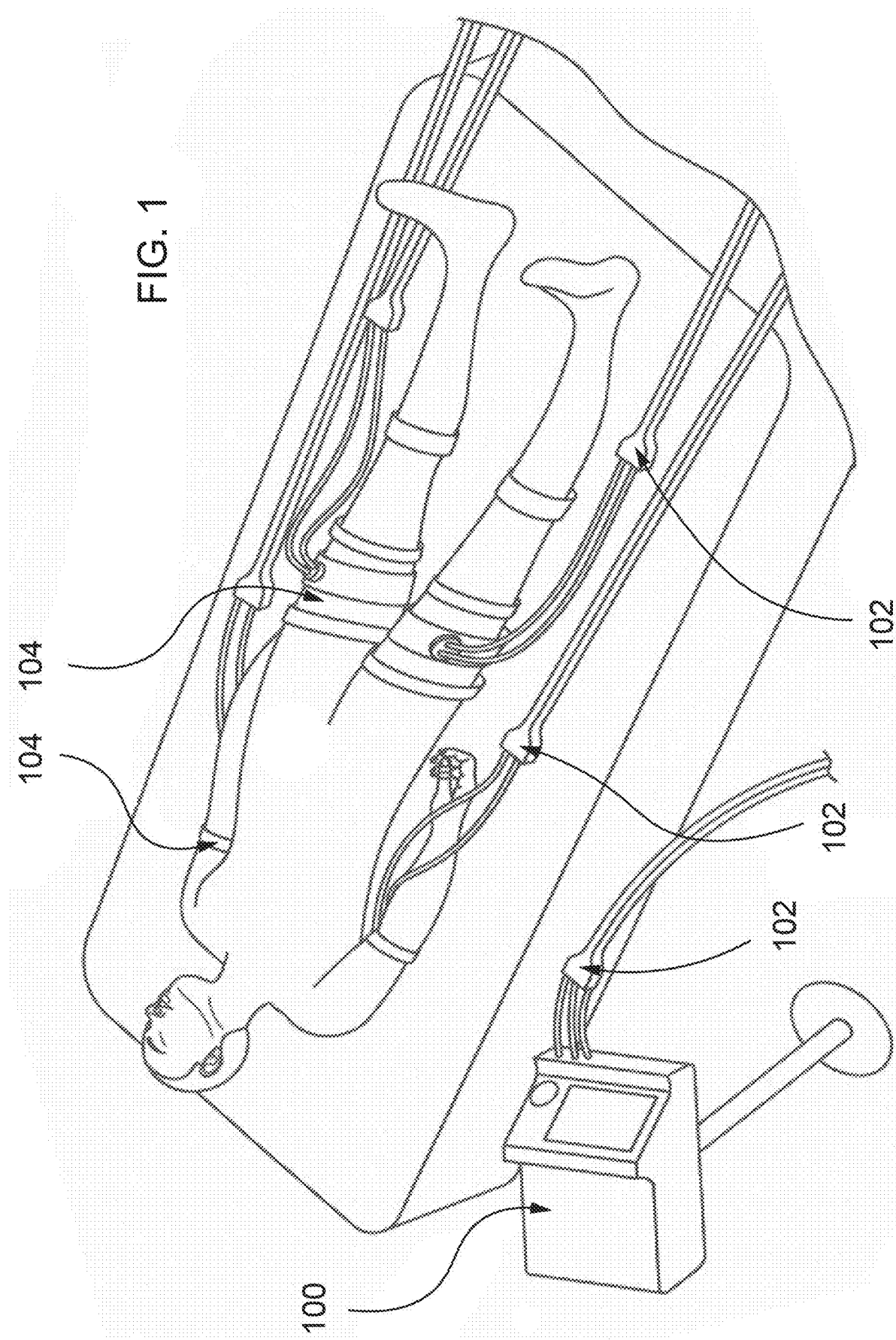
FIG. 1 is a perspective view of a system of the present disclosure shown in operation by cooling/heating contact areas at the thighs and underarms to control core temperature of a patient.
Figure 2:
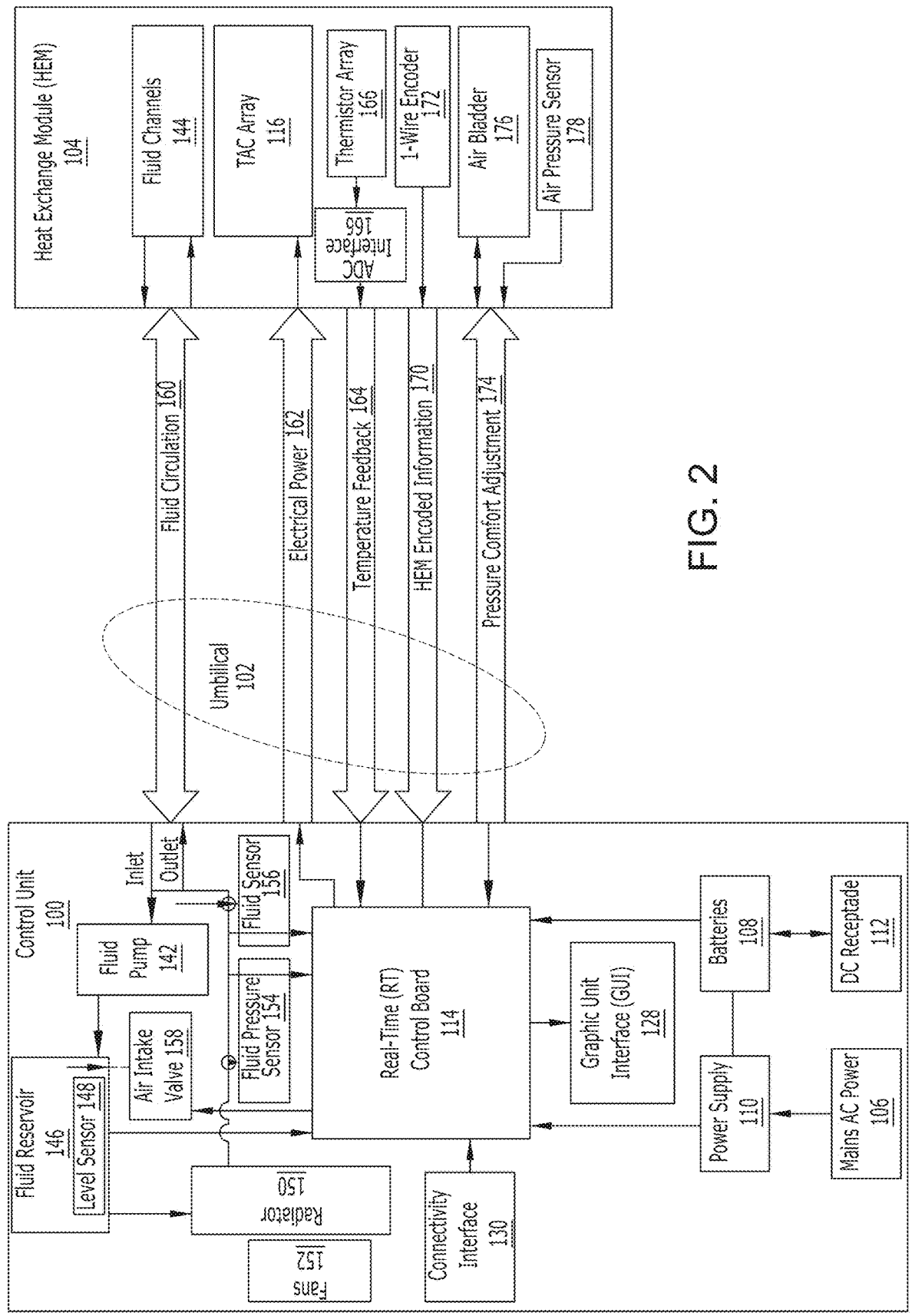
FIG. 2 is a schematic diagram of the system outlining operational connections among components of the control unit, HEM and umbilical.

The disclosure includes a compact and portable device system, which is shown generally at FIG. 1 and includes a control unit console shown generally 100, an umbilical 102 operatively connecting them, and an array of thermoelectric coolers (TECs) arranged in flexible HEMs 104, specifically designed to transfer heat through direct contact with contoured objects. One of ordinary skill in the art will understand and be enabled to design and construct TECs of the disclosure of any size, shape, and consistency depending on the desired purpose. In a principal embodiment, HEMs are ergonomic units optimized for heat transfer through the skin for the induction of therapeutic hypothermia and hyperthermia. The functional architecture of the system illustrated in FIG. 2 contemplates the control unit 100, which provides the necessary support for the operation of HEM 104 through an umbilical 102 which connects it with the HEM. The control unit 100 can be a portable console which is easily transported by hand or integrated into a soft good, as the case may be, which provides an additional advantage of system mobility.

Construction and Operation of Control Unit and Umbilical

Control Unit

The control unit 100 can include an enclosure, a power supply, batteries and electronic components (which can include a real-time (RT) control board, a graphic unit interface (GUI) and a connectivity interface) and fluid circulation and heat dissipation components (which comprise a fluid pump, a fluid reservoir, a radiator, fans, a flow sensor, a pressure sensor, a fluid pressure sensor, and an air valve).

Enclosure

The enclosure can be made of cast urethane, injection molded plastic or any comparable method. It can be made from a single piece or by joining multiple panels that are snapped together, screwed together, or connected by other mechanical or adhesive methods including a combination of the methods. The enclosure's main purpose is to house the internal components of the control unit 100 and to support the input and output ports and connectors needed to interface the unit with the HEMs through the umbilical connector. The enclosure also maintains its rigidity and has adequate vent openings in support of the operation of fans pushing or pulling air for heat dissipation from the radiator. The enclosure also can be constructed to maintain safety in the event of a fluid leak near electrical components.

Power Supply

When connected to the mains AC power 106, the power supply provides electrical DC power for the internal operation of the Control Unit and the HEM, and power for charging the batteries 108. The power supply is connected to the mains AC power (240V/110V) available in medical and commercial institutions, emergency vehicles, domestic services worldwide, etc. The DC voltages range between 6 to 36V and the maximal current capacity is typically 20 A, but can be extended up to 40 A depending of the demands. In the current embodiment, the power supply 110 specifications are: 120/(240)VAC input; 24 VDC/25 A output; 600 W. While less demanding HEMs may require a less powerful supply, more powerful systems may require multiple power supplies capable of delivering up to 1.5 kW of DC electrical power. It will be apparent to one of ordinary skill in the art, that certain embodiments disclosed herein, will require embodiments with varied power levels.

Batteries

The control unit 100 can be designed so that its functionality is sustained for long periods (more than 45 minutes) when operating on battery power alone if and when it is disconnected from the mains AC power 106. This is made possible by the inclusion of a set of internal batteries 108. In a current embodiment, these are 2×24V lithium-ion batteries. In this embodiment, the batteries 108 are constantly being charged when the control unit 100 is connected to the mains AC Power 106. In other embodiments, internal batteries of other types and ratings are envisioned to be charged while the unit is connected to the AC mains. Alternatively, external batteries (battery packs) and/or external power supplies can be used either as supplemental, or as alternatives, to the internal batteries either for the operation of the control unit 100, or for replenishing the charge of the internal batteries.

In these embodiments, the units can include a DC receptacle 112, independent from mains power receptacle, which accepts and secures a battery pack in place, and/or allows for DC power entry. External batteries can also be charged through this receptacle when connected to the unit when it is plugged to the mains.

Electronic Components

Real-Time (RT) Control Board

It is a printed circuit board designed to transmit the appropriate electrical power to the HEM 104 using temperature as a feedback signal. The RT control board 114 contains all the electronic components required for the real-time control of the cooling and heating operation of the HEMs. The RT control board 114 has an internal clock for timing purposes and can have a programmable central processing unit (CPU), typically a high-performance Advanced RISC Machine (ARM) 64-bit processor; however, more advanced processors are envisioned as necessary in future embodiments. The CPU operates under a custom-designed embedded program that can be written in C or assembly languages, or other equivalent encoding language. The embedded software supervises the logic operation of all the sensors and effectors responsible for the cooling and heating by the HEM, the appropriate fluid circulation, the appropriate control of the fans' speed. Importantly, the embedded software contains multiple sections of code to determine whether the system is running safely or it must be instantly halted due to conditions that may be harmful to the user.

A principle variable that the RT control board 114 regulates through its embedded code is the temperature of surfaces in contact with the HEM. It does this by the means of complex algorithms that analyze in real time the feedback information from one or a multiplicity of thermistors in the HEM 104 and (within fractions of a second) determine the electrical power necessary to change or maintain these temperatures.

In one embodiment, the algorithms entail averaging the feedback temperature from 24 thermistors, using the proportional-integral-derivative (PIO) mechanism for bi-directional current control, and driving the array of TECs 116 of the HEM 104 with power controlled by a pulse width modulation (PWM) approach using a full-bridge PWM gate driver with 24V/20 A maximum. The PWM output can be low-pass filtered with a cascade LC filter so that the power to the HEM 104 has a DC voltage value which depends on the dwell time of the PWM. Further, the minimal dwell time, which defines the maximal average voltage output fed to the HEM, is specifically determined for each HEM using identification information received from its 1-Wire encoder (see below). This permits the setting up of optimal operational conditions for individual TECs in each HEM 104. In another embodiment, the average voltage supplied to the HEM 104 comprised of serially connected array of 12 TECs (12-TEC HEM) was 24V; using individual TEC parameters, it was ascertained for this embodiment that their minimal coefficient of performance (COP) was close to 1.0 at a delta-T (hot side minus cold side temperatures) of 30 degrees Celsius.

As illustrated in FIG. 3, this embodiment permits rapid cooling of the skin by the HEM from a typically average temperature in the range of 25-34 degrees Celsius as noted by 118, to less than 10 degrees Celsius in less than 4 minutes as noted by 120, while maintaining a stable temperature value of 6 degrees Celsius (lower dotted line) for tens of minutes as noted by 122. The low temperature of 6 degrees Celsius was chosen in this case as a safe value for long term patient's use; nevertheless, temperatures down to below freezing are possible if desired. Furthermore, the cooling phase can be rapidly reversed to a heating phase to create contrast therapy. As noted by 124 in FIG. 3, it takes less than two minutes to heat the patient's skin to 40 degrees Celsius after the 6 degrees Celsius cold treatment, and the warm temperature can also be stably maintained for tens of minutes as noted by 126. Similarly, high temperatures above 48 degrees Celsius are possible if desired. In other embodiments, multiple heating/cooling cycles, lasting for selected periods of time each, can be readily programmed by the user.

Other control algorithms are conceived in which temperature feedback arises from a multiplicity of thermistors (from one to any number) and in which weight factors can be applied to each thermistor. In addition, the RT control board 114 can be designed with multiple power outputs with various power limitations, each controlled by PIO or alternative algorithms, and driven by PWM or alternative methods. These outputs can feed multiple HEMs, or multiple banks of TECs within one HEM. These latter embodiments permit that HEMs may attain independently controlled temperatures at various contact areas (regional temperature control). Embodiments of regional temperature control include the possibility of heating certain regions of surface contact while cooling others, thus creating temperature gradients at the patients' skin which may be sustained for hours. Surface temperature gradients ensure the creation of deep tissue gradients that may be beneficial for several health conditions and for a plurality of purposes including but not limited to surgery.

Graphic Unit Interface (GUI)

The GUI 128 typically serves as an interface for the transference of information, through a touch screen, to and from the user to the RT control board 114. The touch screen displays the most relevant system parameters (temperature, pressure, flow rate, batteries' charge, etc.) and allows the user to enter parameters such as desired temperature, temperature control paradigm, connectivity information, etc.). In one embodiment, the GUI 128 can have its own CPU (ARM i.MX6) with a Portable Operating System Interface (POSIX), programmed using high level utility programming languages (standard C, C++, Python, etc.), and physically connected to the touch screen. However, alternative options using different CPUs, embedded operating system platforms, remote touch screens (such as smart phones and other intelligent remote platforms), laptops or console computers, all connected through wired or wireless connections, using proprietary or commercial application programs (apps) and various connectivity languages, are also conceived. Consequently, the GUI 128 can be internally connected to the RT control board 114 and mounted such that the touch screen is readily accessible to the user, or it can be split into a console-resident interface that connects internally to the RT control board 114, but externally to a touch screen device or computer (laptop or console) using a wired, or wireless, protocols of connection though the connectivity interface 130.

Connectivity Interface

As illustrated in FIG. 4, the control unit 100 has a built-in interface that permits its connectivity between the user 132 by using external device through either wired protocols 134, including but not limited to USB and RS232, or a wireless protocols 136, including but not limited to Wi-fi and Bluetooth. The connectivity interface 130 allows the control unit 100 to detect wired or wireless information and, after following a recognition protocol, informs the RT control board 114 of the establishment of a link. The user can then operate the control unit 100 as a slave controlled by a remote program, and transferring data using wired or wireless protocols. In one embodiment, the control unit 100 includes a connectivity interface 130 that uses the built-in touch screen 138 to display the system parameters while operating under wired or wireless remote control. In embodiments without touch screen, updated display of the system status is transmitted by wire or wirelessly to remote applications 140.

Fluid Circulation and Heat Dissipation Components

The various components for fluid circulation and heat dissipation in the control unit 100 ascertain that fluid is distributed to the HEM 104 at a flow rate sufficient for the adequate exchange of heat generated or consumed by the TEC array 116 of the HEM 104, and for the adequate exchange of this heat with the environment by a radiator. In a typical embodiment, the circulating fluid can be water, distilled water, distilled water with an antimicrobial agent to prevent the long-term growth of microbes which may interfere with the operation of the system. In other embodiments, additional additives can be included in the fluid, such as (among others) agents to reduce the surface tension of water, agents to protect the life of internal components, agents to buffer against pH changes, and coloring agents for the visualization of long-term chemical changes. In yet other embodiments, the system can take advantage of synthetic fluids with improved heat conductivity with respect that of water.

Fluid Pump

The fluid pump 142 can operate at voltages between 6 to 24V and be capable of circulating fluid at the HEMs (through the umbilical connection 102) at a minimal rate of 0.5 L/min and up to 20 L/min. In a current embodiment, a 12V centrifugal pump, with a maximum static head pressure of 24 feet of water (10.4 psi) and maximum flow rate of 16 L/min, operates in a closed-circuit configuration comprising the fluid reservoir, radiator, connecting tubing inside the console, umbilical connecting tubing, and HEM fluid channels 144. In this embodiment, ⅜" internal diameter flexible plastic tubing is used to connect the individual fluid circuit components inside the console using barb or compression fittings. The inlet and outlet of the fluid circulating system in the control unit 100 can be panel mounted by creating a cut-out in the enclosure such that it can be inserted partially through the hole and mechanically fixed, whether through screws or a snap-in feature. Using barbed connectors and flexible tubing, the inlet to the fluid pump 142 is connected to the umbilical fluid circulation return line (inlet), and its out port is connected to the fluid reservoir 146. More (or less) powerful pumps (8 to 30 L/min; 5 to 50 ft of fluid), and various types of flexible plastic tubing (PVC, polyurethane, Tygon, etc.) ranging from ¼" to ¾" internal diameters, can be chosen to serve the demands of fluid circulation in the console. The closed-circuit configuration of the fluid circulation system is a desirable feature since it provides immunity to hydrostatic pressure changes created by level differences between the control unit 100 (pump level) and the HEMs; furthermore, it allows the maximal overall system pressure to be adjusted to values lower than the maximal head pressure of the pump (see below). Though not optimal, an open loop system can be implemented if the HEMs and connecting tubing are designed to tolerate pressures as high as the maximum static pressure of the chosen pump.

Fluid Reservoir

The fluid reservoir 146 can be a hollow plastic tank with an internal volume between 200 ml and 10 L, depending on the fluid volumes of the largest HEMs connected to each console type. The fluid reservoir can have inlet and outlet threaded connectors, barbed connectors, or compression fittings for fluid tubing, and extra connectors for one or more level sensor 148, temperature probes, etc. In a typical embodiment, the fluid reservoir 146 is a 1.1 L tank with built-in barbed connectors for fluid entry from the fluid pump 142 (inlet) and exit (outlet) to the radiator 150. The fluid level sensor 148 is electrically connected to the RT control board 114 to inform the CPU that an adequate amount of fluid in the reservoir can support the pump operation.

Radiator

The radiator 150 is an important component of the system that is responsible for the effective exchange of heat as to permit the steady operation of the TECs, either by releasing heat when the TECs in the HEMs are in a cooling mode, or by capturing heat when the TECs operate in a heating mode. The power efficiency of the radiator 150 to exchange heat with the environment depends primarily on design features by manufacturers, but within manufacturing boundaries, on the rate of fluid circulation through the radiator, the number of fans 152 attached to the radiator, and on the rate of air flow driven by each fan.

In one embodiment, fluid circulation through the radiator is facilitated by plastic tubing connections to the fluid reservoir (inlet) and to the fluid pressure sensor 154 (outlet). The heat performance of the system is such that a radiator 150 with 2×120 mm fan brackets, and two fans attached in a push configuration, can exchange approximately 380 W of heat with less than 10 degrees Celsius temperature differential between the fluid and ambient temperatures, when the fluid rate is 2 L/min and the fan air flow is 58 cfm. This heat exchange number can be increased in other embodiments to exceed 1.5 kW by increasing the fluid flow rate, the number of fans per radiator, and the fans' cfm. In embodiments where it may become necessary to extend the heat exchange requirements beyond these limits, radiators accepting larger fans can be used in combination with multiple fans.

Alternatively, an external heat exchanger can be connected to the console by a secondary umbilical. This external heat exchanger can be comprised of an ancillary radiator and supporting fans, with or without an ancillary fluid pump, or it could be a fluid chilling unit based on standard compressor/condenser technology.

Fans

The fans can be mounted to the radiator, and the radiator/fan assembly can be situated such that the fans have direct access to external air.

In a current embodiment, two 120 mm fans 152 are used in a push configuration, each of them capable of delivering 58 cfm when operating at 2150 rpm. Other embodiments may comprise a slightly less efficient configuration of a single fan, two fans pulling air from outside through the radiator, four fans in a push-pull configuration with a 240 radiator, and multiple combinations contemplating the use various size families of radiators.

Flow Sensor

The flow sensor 156 is a tachometer whose frequency (after calibration) accurately reports the flow rate (in L/min) in the system. This measurement is electronically reported in real time to the embedded software in the CPU. In the current embodiment, flow rate values are used to indicate potential abnormal uses of the HEMs, or severe conditions indicative of malfunction that should prompt instant interruption of the electrical power delivery to the HEM. The fluid output of the flow sensor 156 is connected with plastic tubing to the umbilical connector outlet from the console.

Fluid Pressure Sensor

The fluid pressure is measured in the control unit 100 by an electronic fluid pressure sensor 154 which in turn conveys the information to the RT control board 114. Fluid pressure sensor data is used for two purposes: a) to inform the CPU that the system operation is within normal ranges (larger than zero and less than the pump maximum head pressure in closed loop systems, or other defined boundaries in open loop systems) and, b) to generate an optimal fluid pressure value that assures the proper flow circulation throughout the system. This latter condition is important given the flexible nature of the HEMs' fluid channels which can unreasonably expand when the high fluid pressure becomes too high, or collapse if the pressure is too low. In a current closed-loop embodiment, this optimal condition is attained by a feedback algorithm that uses pressure sensor information to temporarily open an air intake valve 158.

Air Intake Valve

In one embodiment, prior to the establishment of the steady fluid circulation, the embedded software encoded at the CPU reads (in real time) the value of the fluid pressure sensor 154, and periodically opens the air intake valve 158 until the fluid pressure reaches an optimal level (6-9 psi measured after the fluid exit from the radiator); later on, the valve remains closed (closed-loop configuration) throughout the operation of the system. Alternatively, in open loop configuration embodiments, the air intake valve 158 remains always open.

Umbilical

The umbilical 102 provides the link between the control unit 100 and the HEM 104, and ensures the necessary support for the safe and reliable HEM function. The umbilical's length typically ranges from 2-12 feet, but it can be longer or shorter if necessary. The umbilical 102 comprises the following supporting sub-components.

Fluid circulation 160: An extended section of a paired tube, ranging from ⅛" to ¾" in internal diameter, and made from a flexible material, that go from quick disconnect fittings on the control unit 100 to the HEM 104. Appropriate connector, with barbs if necessary, are attached to the ends of these tubes such that they can plug into the quick disconnect fittings into the HEM.

Electrical power 162: A wire assembly comprised of two cables (insulated positive and negative high current output of the RT Control Board) capable of carrying 20-40 A of current to the HEMs (12 to 16-gauge flexible insulation copper wire) and distributed to the TEC array 116. These wires, cramped or soldered into a heavy duty electrical connector, are part of a single quick connect unit that connects into the control unit 100 on one side, and the HEM 104, on the other.

Temperature feedback 164: Comprises five wires per HEM (+5V, ground, and asynchronous data transmission signals) that allow for the temperature readings from multiple thermistors (thermistor array 166) to be first converted into parallel electrical signals (ADC interface 168), and then into a serial transmission line from the HEM 104.

HEM encoded information 170: One or two lines are used to transmit serially the information encoded in each HEM in a 1-Wire encoder 172 electronic circuit.

Pressure Comfort Adjustment 174: In one embodiment, two wires are used to provide power (12V and ground) to an air pressure pump included in the distal connector (HEM side) of the umbilical 102, and designed to pressurize and deflate the air bladder 176 by the user with pushbutton switches built-in the connector case. Also, wires are necessary to bring (in real time) air pressure sensor 178 readings from the air bladder 176 to the control unit 100 for display by the GUI 128. In another embodiment, the air pump can be included, as a component, in the control unit 100. In this case, an air pressure flexible tube, and sensor reading wires, are necessary to be included as part of the umbilical 102. Air pressure assists with both user comfort, as well as provides improved thermal contact between the HEM 104 and the user 132.

The cables and wires included in the umbilical 102 are connected appropriately in order to be connected to the terminal of the plugs that goes into the control unit 100 on one end and into the HEM 104 on the other end. A braided sleeve or other sheathe can then be wrapped around the entire cable and tube assembly.

General Construction and Operation of Heat Exchange Module (HEM)

Individual TECs 180 (organized in arrays 116) act as direct-contact heat pumping elements of the invention; the outer surfaces of the TECs are in contact with fluid channels. Detailed below are the components and fabrication process for HEMs of this disclosure.

HEM System Architecture

Referring to FIG. 5, an HEM 104 is based around an array of TECs (180, 116) which transmit heat or cooling to the user 132 at the skin level. The TECs are wired in series and provide uniform control of temperature over a large area. Alternatively, TECs can be wired individually or in banks to provide zoned temperature control to specific areas. Each TEC is paired with a thermistor 182, a temperature sensor which provides feedback by measuring the temperature of the thermally conductive surface transmitting temperature to the user known as a tile 184.

Tiles are constrained in a geometric pattern appropriate to the anatomy for which the HEM is intended by attachment to a flexible frame 186. The flexible frame can be made of any flexible material, including but not limited to thermoplastic polyurethane sheets (TPU). The frame retains the tiles and provides a continuous surface barrier between the user and the TECs.

A watertight bladder known as a fluid channel 144 is connected to the TEC array and provides a method of heat extraction from the system. Thermally conductive plates 188 are embedded into a TPU bladder in a pattern mirroring the geometry of the tiles. Each TEC 180 is mounted to a plate that transfers heat 190 from the TEC into a circulating body of fluid. Fluid carries the heat away from the TECs and releases it through a radiator 150 in the externally connected console.

The subassembly of TECs, tiles, and fluid channel can be packaged for use inside a soft good 192 that provides a biocompatible material comfort layer between the user and the tiles, hook-and-loop straps, and/or elements necessary for affixing the device to the user's body, and an air bladder 176 to adjust the pressure and fit.

The user connects the HEM 104 to a control unit 100 via an HEM connector 194 protruding from the soft good. The connector housing contains an HEM board 196, a PCB that provides power management, an interface between the thermistor array 166 and the external console, and a 1-Wire encoder 172 that provides systems identification information to the control unit 100. Fluid and air lines pass through the HEM connector into an umbilical that carries them to the control unit 100.

The umbilical connector 198 can contain an air pump 200, an air pump control PCB board 202 with control circuitry and a pressure sensor 178 and air release valve 204 that control pressure within the air bladder. The user controls the pressure through the air pressure controls 206 in the surface of the connector. The user can increase, decrease, or oscillate pressure over time. The air pump and the air pressure controls can also be located in the control unit 100. Air pressure is used both for the comfort of the user, but also to maximize the heat transfer between the HEM 104 and the user.

It will be readily apparent to one of ordinary skill in the art that an HEM of the present disclosure may be modified to conform to a plurality of purposes. For example, in one embodiment, the air bladder 176 may be present directly within a soft good. However, it will be understood that the functional equivalence of the HEMs of the instant disclosure will be maintained. There is no limitation to the size of the TEC 180 or overall HEM 104, and an HEM 104 can be made to readily accommodate multiple shapes and sizes for various uses.

Detailed Discussion of Hem Embodiments

FIGS. 6-8 show a detached channel assembly embodiment of the present disclosure. It can be seen therein that the (four) collar plates 208 each surround a different portion of the U-shaped fluid channel 144. This allows for more surface area of contact between the fluid channel 144 and plates 188 for better heat transfer. The fluid channels are not attached to the plates, but rather the fluid pressure in the fluid channel forces the fluid channels out against the collar plates 208 for contact.

FIG. 7 shows the upper channel assembly portion 210 separated from the lower tile assembly portion 212. The upper channel portion includes the fluid channel 144 and the collar plates 208. The lower tile assembly portion includes tiles 184 held together by a flexible frame 186. Each TEC 180 is mounted to a tile 184. The plates are attached to the tiles by screws 214, passing through openings in the plates and into threaded inserts 216 on the tiles.

The upper fluid channel portion includes the channel and plates as illustrated in FIG. 8. The fluid channel 144 includes patches 218 of thinner material on which a plate 188 is positioned when assembled. These thin patches allow for better heat transfer between the plates and the fluid circulating in the channel.

FIG. 9 is a view of a linear channel full assembly embodiment of the present disclosure. It is an assembly of a plurality of linear channels configured to form a larger unit. Each linear channel 220 is independent and has its own power connector 222 and thermistor connector 224. A tube fitting 226 is connected to each linear fluid channel, and a curved tube 228 connects each linear channel to the next to form a single continuous fluid path.

FIG. 10 is a top perspective view of a single linear module such as can be used in the above-described multiple linear channel assembly. The underside of this module including its three linearly spaced tiles 184 is shown in FIG. 11. These modules can range in length from one tile length up to an unlimited number of tile lengths.

A bottom perspective view of the fluid channel assembly of the linear channel module is shown in FIG. 12, and FIG. 13 is an exploded view thereof. FIG. 12 shows the plate 188 overmolded with a flexible skeleton 230. The skeleton allows for flexibility in one direction while limiting it in another. The fluid channel can be connected to the adjacent one with the connecting tube 228.

Greater detail of the flexible skeleton features 232 are shown in FIG. 13. It is configured to restrict bending in certain directions, while allowing it in others. This helps to prevent unnecessary wear and improper use of the unit. The flexible skeleton can be overmolded onto the plate 188 and first fluid channel layer 234. A second fluid channel layer 236 and tube fittings 226 are connected to the first fluid channel layer 234 to complete the linear fluid channel assembly.

FIG. 14 is a top perspective view of a U-channel fluid channel assembly of the disclosure and which is similar to that of FIG. 12 except that the connecting tubes are replaced by U-shaped fluid channel turns 238. And FIG. 15 is a top exploded perspective view thereof. These fluid channel turns can be connected to the linear fluid channels 220.

Referring now particularly to FIG. 15, the U-shaped turn is connected via a fitting 240, which is connected to both the linear fluid channel and the U-shaped turn, creating a watertight fluid channel. Each U-shaped turn has two fittings, one on each end to connect to each linear channel. The end fitting 242 on the outermost linear channels has a barbed feature to connect to an inlet/outlet tube.

FIGS. 16 and 17 show a blind fastener channel assembly embodiment, which employs a novel way to attach the plates 188 to a first fluid channel layer 234. For this embodiment, the plates have two parts: an upper blind fastener plate 244, and a lower blind fastener plate 246. The upper and lower plates are held together by a blind fastener 248, creating a watertight seal. This arrangement advantageously allows for the plate to be in direct contact with the fluid using minimal space.

FIG. 17 shows in cross section the first fluid channel layer 234 captured between the upper blind plate 244 and the lower blind fastener plate (246) by a blind fastener 248.

A fluid block full assembly embodiment of the disclosure is illustrated assembled in FIG. 18 and in an exploded view in FIG. 19. The assembly includes essentially three components, namely a serpentine fluid passageway 250, a tile 184 and flexible frame assembly 186, and a TEC array 116. The serpentine fluid passageway includes a fluid block 252 for each TEC and connected in series to the next fluid block by a tube 228. Each fluid block has a tube fitting 226 to connect to the tubes.

Each TEC 180 is mounted to the tile 184. The fluid block 252 is fastened to its respective TEC mechanically to create a thermal contact area to dissipate heat from the TEC into the fluid block. Thereby the TEC can be in direct contact with the fluid circulating in the fluid passageway. Alternatively, a thin layer of highly thermally conductive material can be used between the fluid and the TEC.

A portion of a HEM assembly of the present disclosure is illustrated in cross-section in FIG. 20. Referring thereto, a TEC 180 having a (bottom) user side and a (top) fluid side is provided. The tile illustrated in this figure is a segmented sheet 254 which extends out to form tiles for other TECs in the assembly. (Most other embodiments in this disclosure have individual and separated tiles, each for a different TEC. However, a single sheet can be used with all embodiments.) Also, the sheet is illustrated to have hinge features 256 between TECs to provide flexibility to the sheet and thereby to the HEM assembly so that the HEM assembly will better fit ergonomically to the user's body parts. The hinge feature lines can be in the pattern of a grid to provide flexibility in both the X and Y directions. The hinge feature lines cause the sheet to be a segmented sheet.

The temperature of the user 132 is measured by a thermistor 182 mounted on the heat-conductive tile, which is positionable on and against the user's skin.

A fluid block 252 is used to circulate fluid 258 to the TEC 180. The fluid block is shown in additional detail in FIGS. 21 and 22. The fluid block includes an enlarged box, which is depicted as having six sides, but other shapes are within the scope of this disclosure. The lid of the box is adhesive 260 bonded to the walls of the open base of the box to create a watertight seal. A seal can also be accomplished using a mechanical fastener.

Tube fittings 226 extend out from opposing sides of the fluid block 252, where tubing 228 is attached. Other forms of fluid channels may also be used.

FIGS. 23-25 is another embodiment of the present disclosure, whereby the fluid channel assembly forms a continuous fluid path 262 as shown by the dark arrow in FIG. 23. A continuous fluid channel is formed by joining, by RF weld 264 or otherwise, multiple sheets of material, including but not limited to TPU. Inlet and outlet tubes 228 made from the same material, are joined, by RF weld 264 or other process, into the assembly to connect to an external interface. Cuts in the material 266 may also be used to increase flexibility of the fluid channel 144 specifically, and the HEM generally 104. Inside the fluid channel, standoffs 268, made from the same material can be attached to the inner layer of material, by RF weld 264 or otherwise, to maintain fluid flow and prevent channel collapse when the fluid channel assembly is flexed.

FIG. 24 is a longitudinal cross section of a typical fluid channel of FIG. 23. Plates 188 are embedded between two layers of materials 270, including but not limited to fabric-backed TPU. The first layer of material has cut outs 282 directly under the plate to allow the plate to be in direct contact with the fluid, thus increasing heat transfer. Standoffs 268 may be attached, via RF weld 264 or otherwise, to the material on the side opposite to the plates' elevated platform 272. A second sheet of material 270, is attached, via RF weld 264 or otherwise, onto the assembly to create a continuous fluid path 262. The plates 188, which directly contact fluid flowing in the channel, can be made of any thermally conductive material, including but not limited to aluminum, with or without an adhesion promoting primer coating.

FIG. 25 is a transverse cross section of a typical fluid channel, such as that illustrated in FIG. 23. Illustrated therein are standoffs 268 in the fluid channel which form continuous flow paths 262 and which allow fluid to flow unobstructed even when the fluid channel assembly is flexed.

FIG. 26 shows a method of attaching the plate 188 to the materials 270. The plates can be sealed, hereinafter referred to as embedded 274, onto the material 270 by a variety of sealing processes, including but not limited to heat pressing, RF weld, a combination of both (with or without the use of an adhesion promoting primer), or other methods. A second sheet of material 236 is attached, via RF weld (264) or otherwise, onto the first water channel layer 234 to create a sealed continuous flow path 262.

Apertures in the base sheet allow fluid flowing in the channel to directly contact the thermally conductive surface of the plate.

FIG. 27 shows a double-sided embedding in contrast to the single-side embedding of FIG. 26. Plates 188 are embedded 274 between two sheets of materials 270.

In the embodiment of FIG. 28, a slotted plate 276 is used. The slots 278, also shown in FIG. 29, are designed for use of TPU or other thermoplastic material 280. If the embedding process 274 is completed using heat pressing or RF Weld (or a combination thereof), the slots 278 allow the melted thermoplastic material 280 to create a bond through the slot.

The embodiment of FIG. 30 is similar to that of FIG. 27 except that the material 270 of FIG. 27 covers the plate 188 entirely. Fluid does not come into direct contact with the plate, but heat is still transmitted through the material 270. The material can be thin (between 1 mil to 10 mil) and thermally conductive to increase heat transfer.

FIG. 31 shows a plate 188 having raised features 284, including but not limited to fins, nubs or extrusions extending up from its upper surface.

These features 284 not only prevent the channel or fluid flow area 262 from collapsing like standoffs 268, but also provide additional heat transfer surface area.

FIGS. 32A-e show alternative standoff configurations, namely, straight (FIG. 32A), bowtie (FIG. 32B), double straight (FIG. 32C), double cut v1 (FIG. 32D), and double cut v2 (FIG. 32E). The standoffs prevent channel collapse when the fluid channel assembly is flexed. Each standoff can be connected, by RF weld 264 or otherwise, to the inner layer of the fluid channel 144 allowing fluid to flow around it while pressurized.

FIG. 33 shows an embodiment of the disclosure with blind fasteners 248 being used to retain the thermistor 182 and/or a rigid retainer 286 which holds the flexible frame 186 to the tile 184.

An alternative embodiment to the attachment means of FIG. 33 is illustrated in FIGS. 34A and 34B. Referring to these two figures, thin-walled features 288 in the tile 184 can be deformed by applying compressive force. The deformation can be used to captivate the thermistor 182 and/or frame retainer 286. FIG. 34A shows the assembly before the crushing force is applied and FIG. 34B is an after force application figure.

FIG. 35 shows that the flexible frame 186 can be embedded 274 directly onto the tile.

FIG. 36 illustrates that the flexible frame 186 can be fastened to the tile 184 by a retainer 286 that is adhered to the tile 184 with an adhesive 260, such as epoxy or other rigid adhesive.

The thermistor 182 can similarly be secured to the tile 184 with an adhesive 260, such as epoxy or a thermally conductive adhesive 292.

FIG. 37 is an alternative embodiment of the disclosure, where a thermally conductive material 290 is placed between the tile 184 and the user 132. The thermally conductive material 290 can be used to provide comfort or padding to the user, can be shaped in a variety of ways and thicknesses. The thermally conductive material 290 can be a silicone, foam, gel, or liquid.

FIG. 38 is an embodiment of HEM assembly showing a TEC 180 bonded with thermally conductive adhesive 292 to a plate 188. Foam insulation 294 can be infilled between the TECs 180 to prevent heat dissipation and condensation because of humidity. The user-facing side of the TEC is adhesive bonded to a continuous surface of segmented sheet 254 that transfers heat to or from the user 132. A thermistor 182 is attached to the inside face of the segmented sheet 254.

In the embodiment of FIG. 39, the user-facing side of the TEC 180 is bonded to a flexible thermally conductive material 296, including but not limited to graphite, carbon fiber, carbon fiber mesh, carbon nanotubes, or other thermally conductive synthetic materials.

In the embodiment of FIG. 40, the TEC 180 is bonded with a thermally conductive adhesive 292 to a plate 188 and tile 184. The plate 188 is embedded 274 into one or between two layers of material 270. The circulating fluid 258 is in direct contact with the plate 188. A thermistor 182 is attached to the inside face of the tile 184.

FIG. 41 is an alternative embodiment of HEM assembly that uses a horizontal snap. A horizontal snap assembly of this assembly disclosure is illustrated in assembled cross-section in FIG. 41, in assembled perspective view in FIG. 42 and in ready-for-assembly separated condition in FIG. 43. Referring to these drawings, the horizontal snap assembly is seen to include three components, namely a plate 188, a TEC 180 and a tile 184. Snap hooks 298 on the tile 184 and plate 188 engage with one another horizontally captivating the TEC 180. Thermally conductive paste 300 can be applied to each side of the TEC 180 to improve thermal transfer.

FIGS. 44-46 are an alternative embodiment of HEM assembly that use vertical snaps. Referring to the embodiment of FIGS. 44-46, the plate 188 has downwardly-descending snap hooks 298 engaging with a thermally insulating snap clip 302. A compressible thermally conductive material 304 can be used to ensure thermal contact between TEC 180, tile 184 and plate 188.

FIG. 47 is an alternative embodiment of HEM assembly that uses a screw attachment. A non-thermally conductive screw 306 is threaded through holes in the tile 184, through a TEC 180 (which can be modified to have a hole in the center), and into the plate 188. A compressible thermally conductive material 304 or a thermally conductive paste 300 can be used to ensure thermal contact between TEC 180 and tile 184, and TEC 180 and plate 188. For HEMs 104 with larger TECs 180, multiple screws may be used.

FIGS. 48-50 is an alternative embodiment of HEM assembly that uses a screw attachment with an electrical and thermal insulator 306. The embodiment of FIGS. 48-50 is similar to that of FIG. 38 as follows. A screw 214 is threaded through holes in the tile 184, the TEC 180 and the plate 188. A compressible thermally conductive material 304 or a thermally conductive paste 300 can be used to ensure thermal contact between TEC 180 and tile 184, and TEC 180 and plate 188. A thermistor 182 is mounted to the tile.

The differences are that in FIG. 48 a screw 214 of any material can be used, because it is insulated from the TEC 180, tile 184, and user 132 by an electrical and thermal insulator 314. And an additional layer of electrically insulative material 308 can be used between the user-side surface of the TEC 180 and the inside surface of the tile to minimize the possibility of dielectric breakdown between the TEC 180 and the tile surface 184. The use of an electrically insulative material 308 is not limited to this embodiment, and can be used in all figures set forth herein.

FIGS. 51-56 illustrate an HEM assembly of the present disclosure which uses a screw method of assembly. FIG. 51 is a bottom perspective view of the assembly showing its three-by-four array of tiles. FIG. 52 is an exploded perspective view of the HEM assembly. Referring thereto, the TECs 180, thermal interface layer (300 or 304), and thermistor wire harness 310 (consisting of multiple thermistors wired together) are captured between the fluid channel 144 and tile and flexible frame subassembly 312 and non-thermally conductive screw 306. The fluid channel tubes and thermistor wires are routed through a molded cosmetic cover 316 to be inserted into the HEM connector 198.

FIG. 53 is a bottom perspective view of the fluid channel assembly of FIG. 52, and FIG. 52 is an exploded perspective view of the fluid channel assembly.

FIG. 55 is a top perspective view of the tile and flexible frame assembly 312 of FIG. 52, and FIG. 56 is an exploded perspective view thereof. Referring thereto, retainers 286 attach the flexible frame 186 to the tiles 184. Thin-walled crush posts in the tiles can be deformed by applying compressive force to hold the retainers in place.

FIG. 57 is a flow chart showing the steps of producing an HEM assembly. The flow chart has two paths, namely fluid channel assembly and tile and flexible frame assembly paths which come together at the bottom of the page, and are explained below. FIG. 58 is a flow chart showing the steps for producing a finished good of the present disclosure and has three paths at the top of the page, namely one for the umbilical, one starting with the HEM assembly from FIG. 57 and one for the soft good. The process is discussed below.

1. Fluid Channel Assembly
   (a) Plates are machined or cast from a thermally conductive metal or material
   (b) Detailed or high tolerance features are post-machined
   (c) Plates can be sandblasted to increase surface roughness and promote adhesion
   (d) Plates are coated with an adhesion promoting primer
   (e) Plates are dried
   (f) Embedding materials are laser or die cut to shape
   (g) Embedding materials and plates are loaded into embedding tool such as heat press or RF weld machine
   (h) Components are embedded at precise temperature and pressure duration for a set time
   (i) Embedded channel is removed from tool
   (j) Standoffs are die cut
   (k) Standoffs are adhered to, by RF weld or otherwise, to reinforced material of the channel per layout drawing
   (l) Reinforced material top sheet is heat pressed or RF welded to embedded layer to form channel path
   (m) TPU tubes are welded into inlet/outlet of channel
   (n) Fluid channel is tested for leaks with air pressure
2. Tile and Flexible Frame Assembly
   (a) Tiles are machined or cast from a thermally conductive metal or material
   (b) Detailed or high tolerance features are post-machined
   (c) Tiles are sandblasted for appearance
   (d) Tiles may be anodized for durability and appearance
   (e) Retainers are machined, laser cut, or stamped from stainless steel alloy
   (f) Flexible frame is thermoformed
   (g) Formed flexible frame is laser or die cut to shape
   (h) Tiles and retainers are installed into the flexible frame using PEM inserts or crush posts
3. Soft Good
   (a) Textile patterns are laser or die cut
   (b) Pull tabs and grommets are injection molded Branding and logos are applied
   (c) Outer textile layers are joined
   (d) Secondary straps are joined to textiles
   (e) Air bladder and tube are RF welded together Air bladder is joined into textile assembly Inner fabric layer is joined
   (f) Zipper is joined
   (g) Edge binding is applied
   (h) Soft good undergoes cosmetic inspection
4. Assembly
   (a) Thermistors are attached to tile using PEM inserts or crush posts
   (b) Thermistors harness is routed
   (c) Thermal transfer layer is applied to plate and tile platform surfaces
   (d) TECs are placed onto plate
   (e) Tile and flexible frame assembly is placed on top of TECs
   (f) Screw insulators are installed into through-holes of tiles
   (g) Tiles are screwed into plates
   (h) Screws are covered with insulating cap or potting compound
   (i) Tubes and wires are routed through umbilical sleeve material and tube outlet
   (j) Tube outlet is aligned to edge of fluid channel/tile and flexible frame to conceal tube RF area and visible wiring
   (k) Quick-disconnect connectors are attached to fluid channel tubes
   (l) Thermistor harnesses are connected to HEM PCB
   (m) HEM PCB and TEC power cables are soldered to electrical connector
   (n) Pass-thru air fittings are assembled
   (o) HEM connector housing is assembled, captivating electrical, fluid, and air connectors
   (p) Edges of fluid channel, tile and flexible frame, and tube outlet are bound to finish assembly
   (q) HEM undergoes final inspection and testing
5. Finishing
   (a) Completed HEM is placed inside soft good
   (b) Air bladder is connected to air inlet on HEM connector
   (c) HEM is filled with fluid and anti-microbial additive
   (d) HEM is packaged for shipping FIGS. 59a-59g illustrate a variety of tile shapes that can be used to improve ergonomics for HEMs used on different areas of the anatomy. As shown, the tiles 184 can be square or have chamfered edges, for example. Tiles can also be curved as shown by the direction of curvature 318 or flat. For assembly embodiments that use screws, a through-hole 320 is formed in the center of the tile 184. One of ordinary skill will understand that any shape may be attained using the methods set forth in this disclosure. The desired purpose will motivate one of skill in the art to determine the best shape needed.

FIG. 60 shows a cross section of a curved tile using an insulative screw 306 assembly method. The areas of the tile 184 in contact with the TEC 180 and the thermistor 182 are flat. Material is removed in all surrounding areas to minimize material thickness. The curvature of the tile matches the curvature of the user's skin surface 322.

FIG. 61 is a diagram of an HEM of the disclosure inserted into a soft good for a back.

FIG. 62 is a diagram of an HEM of the disclosure inserted into a soft good for a knee.

FIG. 63 is a diagram of an HEM of the disclosure inserted into a soft good for a shoulder.

FIG. 64 is a diagram of an HEM of the disclosure inserted into a soft good for an ankle.

FIG. 65 is a diagram of an HEM of the disclosure inserted into a soft good utility pad.

FIG. 66 shows an exploded view of an air bladder contained within a soft good (in this case a Utility HEM) showing the air bladder 176 relative to the other components. The air bladder is a standalone component located between a first soft good layer 192, which contains the HEM 104, and a second soft good layer 192. The two soft good layers can be stitched together.

FIG. 67 shows an exploded view of an air bladder 176 contained within an HEM 104 assembly (in this case a Utility HEM). In this embodiment, the air bladder 176 is a part of the HEM itself. The current method is another material layer 270 joined, by RF weld or otherwise, to the existing fluid channels 144.

FIG. 68A-i show different applications of the technology, such as virtual reality, car seat temperature control, and full body cooling and are further described below.

FIG. 68A shows front and back views of a temperature control suit 334 as being worn by a user 132. As shown, the temperature control suit 334 can be a single piece of material (or multiple pieces such as a shirt and pants, which may or may not connect together). Built into or attached to this suit as a plurality of HEMs 104. A preferred HEM construction is illustrated in FIG. 5 of this disclosure. Each of the HEMs 104 is illustrated as including an array of TECs 116. In this figure each module is shown to include a three by four array of TECs 116, though more or less and even one can be used. The modules are connected by lines, which include fluid and electrical connections. The modules can be individually controlled or controlled together.

FIG. 68B shows an alternative to the embodiment of FIG. 68A. This embodiment includes just a shirt with interconnected HEMs 104 contained in the shirt at spaced locations. These HEMs 104 can then be controlled from a remote wireless unit 328 so the person is free to move about.

FIG. 68C shows a TEC array 116 built into an HEM helmet 330. The helmet 330 is physically connected to a control unit 100 by an umbilical 102. Examples of uses of this embodiment include medical use for patients to avoid side effects of chemotherapy, such as hair loss, and treatment for stroke. The TEC arrays 116 can be configured in any arrangement in the HEM helmet 330.

FIG. 68D shows an embodiment consisting of an HEM chair 332. The HEMs 104 in this embodiment are arranged in three different zones (a, b, and c). Each of the zones is separately controlled by the control unit 100. Thereby the temperature in each of the zones can be individually and separately controlled. For example, a user (or manufacturer) may want zone b to be cooler than zone a and zone c warmer than zone a. The HEM chair 332 can be made to have a single zone or multiple zones, and the HEMs 104 can be configured in any arrangement.

FIG. 68E shows an HEM chair 332 adapted to be used in an automobile. The HEMs 104 are built into a car seat or is added on after manufacture. Similar to FIG. 68D the HEMs 104 can be configured into separate zones.

FIG. 68F is a variation of the embodiment of FIG. 68A showing a temperature control suit 334 for use in hot environments, including but not limited to race cars and military vehicles. The temperature control suit 334 contains an array of HEMs 104 and can be worn by the user 132. The HEM system is operatively connected to a control unit 100. The control unit 100 can be remotely controlled.

FIG. 68G shows an example of the wide range of applications that can provide temperature control by an HEM 104. Shown therein are a bed embodiment 336, a stretcher embodiment 338 and a neck brace embodiment 340.

FIG. 68H shows an embodiment with two HEMs 104 used on a single user 132. One HEM 104 is on the leg of the user 132, and the other HEM 104 is on the arm of the user 132. Each is connected to and operated by a single control unit 100. This allows different temperatures to be applied to the leg and the arm as shown in the graph 342.

FIG. 68I shows an HEM 104 being used as part of a VR system. This allows different bursts of cold or heat to be applied to the user 132 at different locations on the body. It can be applied as a temperature control suit 334, or through a vest or other soft good.

FIG. 69 shows a drawing of a liquid container 324, in this case a keg, and a comparative illustration of one embodiment of the invention in which two HEMs 104 are attached to the container. That is, another embodiment of the disclosure is to take advantage of the metallic fabrication, typically aluminum, of kegs. For a common sized keg, the embodiment can be used to wrap HEM shaped as belts 326 at various heights of the keg. In a current embodiment, two belts consisting of eight TEC arrays 116 are tightly attached to a keg. The tiles 184 are in direct contact with the keg and have the same curvature. Not shown in the figure is a soft good wrap 192 that covers the entire container and tightens the belts against the keg surface. Other embodiments tailored for various sizes of kegs, with more or less than two belts, or with smaller or larger TECs, with different numbers of TECs, using other conductive materials, are all additional variations of this embodiment.

A smaller, lighter portable version the device that allows for greater mobility is illustrated in FIG. 70.

I. Soft Goods

As a further embodiment of the disclosure, the disclosure comprises soft goods. For purposes of the disclosure, "soft good" means a subclass of nondurable goods as represented especially by textile products including but not limited to clothing, fabrics, and bedding.

It will be understood by one of ordinary skill in the art, that the soft good can be washable either by machining or hand and will be made from a plurality of materials including but not limited to, nylon, polyester, cotton, linen, elastic, neoprene, thermoplastic polyurethane (TPU), thermoplastic elastomer (TPE), and any biocompatible material in compliance with ISO 10993.

One of ordinary skill in the art will understand that a soft good of the present disclosure will be adjustable such that the HEM of the present disclosure can conform to a user's body in a way to maximize surface area contact. See, for example, FIG. 59, which shows several embodiments of tile geometry to conform to a user's body. In addition, the soft good will have a later of biocompatible material between the user's skin and all heating and cooling surface area.

Accordingly, in a preferred embodiment of the present disclosure, the soft good comprises the following two-pronged manufacturing steps. First, the soft good material is cut to fit a certain specification using methods known in the art (e.g. laser, die cut, etc.). Second, the inner and outer layer of an air bladder is welded using methods known in the art (e.g. ultrasonic welding, thermosonic bonding, etc.). Third, an air tube is welded using methods known in the art. Fourth, the air bladder is joined. Fifth, the inner fabric of a soft good is joined. Sixth, a zipper to the soft good is joined. Seventh, edge binding is applied using methods known in the art.

Concurrently, a first step of producing the tooling for a soft good is made using methods known in the art. Second, pull tabs and grommets are injected using methods known in the art. Third, branding/logos are applied using methods known in the art. Fourth, secondary straps are joined. Fifth, the air bladder is joined. Sixth, the inner fabric of a soft good is joined. Seventh, a zipper to the soft good is joined. Eighth, edge binding is applied using methods known in the art.

It will be generally understood that a final step of cosmetic inspection will be preferred (although not required) to validate conformance with a soft good specification. A schematic of the two-pronged process for making a soft good of the disclosure is set forth in FIG. 58. It will be apparent to one of ordinary skill in the art, that a step may be optional or added, depending on the design specification for a soft good of the disclosure.

In one embodiment, the HEM of the present disclosure is placed inside the soft good.

In another embodiment, the HEM is integrated into the soft good.

In yet another embodiment, the HEM is mounted inside the soft good such that accurate and repeatable alignment to the user's anatomy is maintained.

One of ordinary skill in the art will appreciate that a HEM device of the present disclosure will be removable from a particular soft good.

Removability will allow for replacement or modification of an HEM to conform for its intended purpose and allow for the soft good to be cleaned. Furthermore, the complete subassembly of TECs, tile and flexible frame, and fluid channel can be packaged within a soft good. The soft good provides a biocompatible material that serves as a comfort layer between the user and the tiles, Velcro straps and/or elements necessary for affixing the device to the user's body, and an air bladder to adjust pressure.

A. Soft Good Back Wrap

In yet another embodiment of the present disclosure, the soft good forms a wrap to be used on a user's back. It will be generally understood that back pain in humans occurs in the lower back; however, other areas of the back may experience pain.

Accordingly, one embodiment of the present disclosure comprises methods of managing pain and inflammation using the HEM of the present disclosure on a human back. It will be understood by one of ordinary skill in the art that the HEM(s) of the present disclosure are placed in the soft good in an optimal pattern using a combination of the users back muscle groups and the users anthropometric data. This is important since each user will differ in height, weight, girth, etc. However, one of ordinary skill in the art will understand and be enabled to use the HEM of the present disclosure within a user's acceptable range of body size. Using the HEMs of the present disclosure, the soft good will conform to the natural curvature of the user's back.

It will be understood by one of ordinary skill that a one size fits approach can be designed; however, the disclosure comprises and contemplates a sizing schema to account for larger or smaller individuals. An embodiment of a back wrap of the present disclosure is set forth in FIG. 61. It will be understood that the back wrap is fit and secured around a user's back via a tightener such as Velcro or other fasteners known in the art. One of ordinary skill in the art will understand that an optional embodiment of the disclosures comprises the use of an air bladder that sits between the user's back and the HEM and is used to optimize the contact of the HEM surface area.

B. Soft Good Knee Wrap

In yet another embodiment of the present disclosure, the soft good forms a wrap to be used on a user's knee. It will be generally understood that knee pain management in humans presents challenges given the unique curvature of the human knee and relates joints.

Accordingly, one embodiment of the present disclosure comprises methods of managing pain and inflammation using the HEM of the present disclosure on a human knee. It will be understood by one of ordinary skill in the art that the HEM(s) of the present disclosure are placed in the soft good in an optimal pattern to establish cooling zones in area of the Suprapatella Bursa, LCL, Patella Tendon, MCL, Gastronemius, and Bicep Femorus. This is important since each user will differ in height, weight, girth, etc. However, one of ordinary skill in the art will understand and be enabled to use the HEM of the present disclosure within a user's acceptable range of body size.

Using the HEMs of the present disclosure, the soft good will conform to the natural disparate sizing of a human knee. It will be understood by one of ordinary skill that a one size fits approach can be designed; however, the disclosure comprises and contemplates a sizing schema to account for larger or smaller individuals. This is especially true since the knee circumference in individuals can range from 0-8 cm. An embodiment of a back wrap of the present disclosure is set forth in FIG. 62. It will be understood that the back wrap is fit and secured around a user's back via a tightener such as Velcro or other fasteners known in the art. One of ordinary skill in the art will understand that an optional embodiment of the disclosures comprises the use of an air bladder that sits between the user's back and the HEM and is used to optimize the contact of the HEM surface area.

C. Soft Good Shoulder Wrap

In yet another embodiment of the present disclosure, the soft good forms a wrap to be used on a user's shoulder. It will be generally understood that shoulder pain management in humans presents challenges given the complex geometry of the shoulder. Thus, one of ordinary skill in the art will appreciate that alternative HEM tiles will be preferred. In a preferred embodiment, the HEM utilizes a cropped tile of the disclosure and a spherical tile of the disclosure.

Accordingly, one embodiment of the present disclosure comprises methods of managing pain and inflammation using the HEM of the present disclosure on a human shoulder. It will be understood by one of ordinary skill in the art that the HEM(s) of the present disclosure are placed in the soft good in an optimal pattern to establish cooling zones in area of the Trapezius, Rear Deltoid, Pectoralis Major, and Anterior Deltoid. This is important since each user will differ in height, weight, girth, etc. However, one of ordinary skill in the art will understand and be enabled to use the HEM of the present disclosure within a user's acceptable range of body size. Using the HEMs of the present disclosure, the soft good will conform to the natural disparate sizing of a human shoulder. It will be understood by one of ordinary skill that a one size fits approach can be designed; however, the disclosure comprises and contemplates a sizing schema to account for larger or smaller individuals.

An embodiment of a shoulder wrap of the present disclosure is set forth in FIG. 63. It will be understood that the shoulder wrap is fit and secured around a user's shoulder via a tightener such as a chest strap or bi-directional arm strap or other fasteners known in the art. One of ordinary skill in the art will understand that an optional embodiment of the disclosures comprises the use of an air bladder that sits between the user's shoulder and the HEM and is used to optimize the contact of the HEM surface area. This is especially important given the complex geometry of the human shoulder.

D. Soft Good Ankle Wrap

In yet another embodiment of the present disclosure, the soft good forms a wrap to be used on a user's ankle. It will be generally understood that ankle pain management in humans presents challenges given the plurality of injuries which may occur in the ankle. The most common injuries are sprains, and in particular, an inversion sprain. However, a skilled artisan will appreciate that a HEM of the disclosure can be used to manage eversion and high ankle sprains, as well as swelling and inflammation in the ankle.

Accordingly, one embodiment of the present disclosure comprises methods of managing pain and inflammation using the HEM of the present disclosure on a human ankle. It will be understood by one of ordinary skill in the art that the HEM(s) of the present disclosure are placed in the soft good in an optimal pattern to establish cooling zones in area of the malleolar zone (high ankle sprains) and the midfoot zone (common sprains, such as inversion and eversion). This is important since each user will differ in height, weight, girth, as well as swelling of the ankle. However, one of ordinary skill in the art will understand and be enabled to use the HEM of the present disclosure within a user's acceptable range of body size.

Using the HEMs of the present disclosure, the soft good will conform to the natural disparate sizing of a human ankle. It will be understood by one of ordinary skill that a one size fits approach can be designed; however, the disclosure comprises and contemplates a sizing schema to account for larger or smaller individuals. An embodiment of an ankle wrap of the present disclosure is set forth in FIG. 64. It will be understood that the ankle wrap is fit and secured around a user's ankle via a tightener such as a Velcro fastener or other fasteners known in the art. One of ordinary skill in the art will understand that an optional embodiment of the disclosures comprises the use of an air bladder that sits between the user's ankle and the HEM and is used to optimize the contact of the HEM surface area. Given the ankle geometry and the fact that mobility is critical several embodiments of the ankle HEMs are contemplated in the present disclosure.

E. Soft Good Utility Pad

In yet another embodiment of the present disclosure, the soft good forms a wrap enclosing an HEM which can be used worn on a user's body part back in the form of a generic utility pad. The utility pad allows for the HEM of the present disclosure to be used on a user's body in an area which may not be specifically contoured as in the preceding embodiments carried in close contact with the soft goods for each individual wrap. It will be understood by one of ordinary skill that a one size fits approach can be designed; however, the disclosure comprises and contemplates a sizing schema to account for larger or smaller individuals.

An embodiment of a utility pad of the present disclosure is set forth in FIG. 65. It will be understood that the utility pad is fit and secured around a user via a tightener such as a Velcro fastener or other fasteners known in the art. Examples of a utility pad include HEMs of the disclosure worn for a head (cryo pad), vests, C-T spine wraps, hands, wrists, hips, groins, total leg, and half leg.

F. Soft Good Wearable Suit(s)

In yet another embodiment of the present disclosure, the soft good forms a bodysuit enclosing an HEM or a plurality of HEMs as the case may be. It will be understood by one of ordinary skill in the art, that the number of HEMs is functional to the intended purpose. One of ordinary skill will understand and be enabled to render multiple HEMs in concert using the system requirements of the present disclosure (See, FIGS. 68A and 68B.) The bodysuit of the present disclosure can be used for a plurality of consumer and industrial uses, some embodiments of which are set forth herein. It will be understood by one of ordinary skill that a one size fits approach can be designed; however, the disclosure comprises and contemplates a sizing schema to account for larger or smaller individuals.

An embodiment of a bodysuit of the present disclosure is set forth in FIGS. 68A, 68B, 68H, and 68I. It will be understood that the bodysuit is fit and secured around a user via a tightener such as a Velcro fastener or other fasteners known in the art.

II. Air Bladder

In another embodiment, the HEM and/or soft good, as the case may be, comprises and air bladder. Generally, an air bladder is contained within the soft good, separated from the mechanical subassemblies by a layer of fabric material (See, FIG. 5). Air pressure inside the bladder can be varied to control pressure of the HEM against the user's body. The air pressure is controlled by a pump inside the umbilical connector (See, FIG. 2) or optionally by a pump located in another area within the HEM of the disclosure (See, FIG. 67).

FIG. 67 shows an air bladder 176 located above the fluid channel assembly 144 so as to come in contact with the user's skin or body. In the alternative, an air bladder can be positioned between the body portions of the inner and outer layers and on the opposite side of the pocket and thereby the module when in place in the pocket. Tubing from the air bladder passes out through a hole in the outer layer. An air inflation bulb is located at the end of the tubing and thereby outside of the soft good wrap. With the wrap in place the bladder can be inflated to the desired size/pressure by squeezing the bulb, and thereby compressing the module against the body part for improved performance.

In one embodiment of the disclosure, the HEM device shall contain an air pressure inside the air bladder can range from O psi to 3 psi. In another embodiment, the HEM device shall contain an air pressure in the air bladder can range from 1 psi to 3 psi. In yet another preferred embodiment, the HEM device shall contain an air bladder capable of generating compression up to 2 psi. It will be understood by one of skill in the art that the air bladder will contain at least one interface from the HEM connector for air flow to/from the HEM to the air bladder. An air hose connects the air bladder inside the soft good to a user-accessible fitting on the HEM connector. Furthermore, it will be understood by one in the art that the air hose must be manually disconnected when removing the HEM assembly from the soft good.

III. Consumer/Industrial Goods/Uses

In yet another embodiment of the present disclosure, the soft good forms a bodysuit/consumer good enclosing an HEM or a plurality of HEMs as the case may be. It will be understood by one of ordinary skill in the art, that the number of HEMs is functional to the intended purpose. One of ordinary skill will understand and be enabled to render multiple HEMs in concert using the system requirements of the present disclosure (See, FIGS. 2 and 5, and FIGS. 68A-68I. The bodysuit/consumer good of the present disclosure can be used for a plurality of consumer and industrial uses, including but not limited to consumer and industrial bedding, temperature controlled containers/vessels, furniture, headwear, headgear, temperature controlled passenger seating, consumer wearable technology, gaming, first aid, medical treatment. It will be understood by one of ordinary skill that a one size fits approach can be designed; however, the disclosure comprises and contemplates a sizing schema to account for larger or smaller individuals.

A. Headwear

In one use, the embodiments of the present disclosure can be used as headwear via a helmet or hat wearing apparatus. The user can adjust the temperature using the system(s) of the present disclosure whereby the desired temperature can achieved. Non-limiting uses of the headwear of the present disclosure comprise medical treatment, such as treatment for cancer patients to reduce or eliminate side effects of chemotherapy, gaming technologies such as virtual reality, etc. An embodiment of the headwear of the disclosure is set forth in FIG. 68C.

B. Furniture

In one use, the embodiments of the present disclosure can be used as furniture via chairs, sofas, etc. The user can adjust the temperature using the system(s) of the present disclosure whereby the desired temperature can achieved. Non-limiting uses of the furniture of the present disclosure comprise medical treatment, gaming technologies such as virtual reality, passenger seating in automobiles, driving seats in racecars, boats, passenger seats for pilots, surgical bedding, hospital recovery bedding, bedding in natural disasters, camping equipment (sleeping bags), etc. Non-limiting examples of an embodiment of the furniture of the disclosure is set forth in FIGS. 68D, 68E, 68F and 68G.

C. Gaming Systems/Virtual Reality (VR)

In one use, the embodiments of the present disclosure can be used as VR system component for gaming. The system can automatically adjust the temperature using the system(s) of the present disclosure whereby the desired temperature can achieved during the course of play. Non-limiting examples of an embodiment of the furniture of the disclosure is set forth in FIG. 68I.

D. Temperature-Controlled Container(s)/Vessels

In one use, the embodiments of the present disclosure can be used as temperature controlled container/vessel for cooling liquids. The user can adjust the temperature using the system(s) of the present disclosure whereby the desired temperature can achieved. Non-limiting uses of the temperature controlled containers/vessels of the present disclosure comprise kegs, coolers, medical transport coolers, food transport containers, temperature controlled freight and cargo containers, etc. Non-limiting examples of an embodiment of the temperature controlled containers/vessels of the disclosure are set forth in FIG. 69.

IV. Kits/Articles of Manufacture

For use in input/output systems, kits are within the scope of the disclosure. Such kits can comprise a carrier, package, or container that is compartmentalized to receive one or more containers such as boxes, shrink wrap, and the like, each of the container(s) comprising one of the separate elements to be used in the method, along with a program or insert comprising instructions for use, such as a use described herein.

The kit of the disclosure will typically comprise the container described above and one or more other containers associated therewith that comprise materials desirable from a commercial and user standpoint, programs listing contents and/or instructions for use, and package inserts with instructions for use.

Directions and or other information can also be included on an insert(s) which is included with or on the kit. The terms "kit" and "article of manufacture" can be used as synonyms.

The article of manufacture typically comprises at least one container and at least one program. The containers can be formed from a variety of materials such as glass, metal or plastic.

A. Soft Good Comprising Console

In yet another embodiment of the present disclosure, the soft good forms a wrap enclosing the Console of the present disclosures (See, FIG. 70) which can be carried or worm on a user's back in the form of a backpack, briefcase, suitcase, garment case, carry case, and/or other packing modality known in the art. The preferred purpose of the console comprising a soft good offers system mobility.

The soft good comprising a console allows for the console of the present disclosure to be carried in close contact with the soft goods for each individual wrap (See, FIGS. 61-65). In one embodiment of the disclosure, the soft good comprising a console of the disclosures is worn by the technician/medical provider administering the pain management treatment and/or medical treatment. In yet another embodiment, the soft good comprising a console of the disclosure is worn by the user (patient, athlete, etc.). It will be understood by one of ordinary skill that a one size fits approach can be designed; however, the disclosure comprises and contemplates a sizing schema to account for larger or smaller individuals.

An embodiment of a soft good comprising a control unit 100 of the disclosure is set forth in FIG. 70. It will be understood that the soft good comprising a console of the disclosure is fit and secured around a user via a tightener such as a Velcro fastener or other fasteners known in the art. This is a smaller, lighter portable version the device that allows for greater mobility.

EXAMPLES

Various aspects of the disclosure are further described and illustrated by way of the several examples that follow, none of which is intended to limit the scope of the disclosure.

Example X

Methods of Making a Soft Good

As previously set forth, the disclosure contemplates the manufacturing of soft goods comprising the HEMs of the present disclosure. The methods for producing a soft good of the disclosure comprise the following steps: (i) the soft good material is cut to fit a certain specification using methods known in the art (e.g. laser, die cut, etc.). As previously described the specification can be formed to fit any individual body part, such as the back (FIG. 61), the knee (FIG. 62), the ankle (FIG. 64), and the shoulder (FIG. 63) as well as any other consumer/industrial good, such as bodysuits (FIGS. 68A, 68B and 68H), furniture (FIGS. 68D and 68E), vessels (FIG. 69), etc.; (ii) the tube is welded to the inner layer using methods known in the art (e.g. ultrasonic welding, thermosonic bonding, etc.); (iii) the air bladder is welded to the outer layer using the aforementioned methods known in the art; (iv) pull tabs are attached; and (vi) the inner layer and outer layer are stitched together using methods known in the art. A schematic of the process for making a soft good of the disclosure is set forth in FIG. 58.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heat exchange module comprising:
   a thermoelectric cooler (TEC) assembly with a heat transfer fluid channel configured for retaining a heat transfer fluid;
   at least one thermoelectric cooler (TEC) having a reference side in thermal contact with at least one thermally conductive plate;
   a flexible frame having one or more openings;
   at least one thermal transfer tile retained within said flexible frame and held in thermal contact with a user side of the TEC which is opposite to said reference side of the TEC, and the module being configured to be operatively positionable with the tile in heat transfer relation with skin of a patient;
   one or more temperature sensors, each said temperature sensor in thermal communication with one of said at least one thermally conductive tile for detecting temperature of the skin of the patient; and
   wherein a liquid chamber box of said thermoelectric cooler (TEC) assembly comprises a first and second sheet of thermoplastic material that is formed and adhered together forming the heat-transfer channel therebetween, and in which said second sheet of thermoplastic material is configured with one or more openings, wherein each of said at least one thermally conductive plate is received by and seals over a respective opening of said one or more openings in said second sheet of thermoplastic material; whereby each of said at least one thermally conductive plate is positioned to be in direct contact with heat transfer fluid flowing through said heat transfer fluid channel.

2. The heat exchange module of claim 1, wherein said at least one TEC is held in sandwich relation between said at least one thermally conductive plate and said at least one thermal tile.

3. The heat exchange module of claim 2, further comprising a screw passing through one of said at least one thermal tile and one of said at least one thermoelectric cooler (TEC), into one of said at least one thermally conductive plate; wherein one said thermal tile and one said thermoelectric cooler are retained to one said thermally conductive plate.

4. The heat exchange module of claim 2, wherein each said at least one thermoelectric cooler (TEC) is configured to be held in a sandwich relation between said at least one thermally conductive plate and said at least one thermal tile which interconnect with a snap-fit mechanism.

5. The heat exchange module of claim 4:
   wherein said snap-fit mechanism comprises a first hook attached to said at least one thermally conductive plate provides a snap-fit engagement with a second hook attached to said at least one thermal tile, between which one of said at least one thermoelectric cooler (TEC) is retained; and
   wherein said snap-fit mechanism is configured for being engaged by bringing said at least one thermally conductive plate and said at least one thermal tile into either horizontal or vertical engagement to retain each said TEC.

6. The heat exchange module of claim 1, further comprising a third sheet of thermoplastic material attached to said first and second sheets of thermoplastic material and formed to attach to a distal portion of each of said at least one thermally conductive plate.

7. A heat exchange assembly, comprising:
   a liquid chamber box configured with a heat-transfer fluid channel;
   a plurality of thermally conductive plates retained on the heat transfer fluid channel and configured for heat transfer relation with fluid in the fluid channel;
   a plurality of thermoelectric coolers (TECs), the reference side of each in thermal contact with an associated thermally conductive plate;
   a flexible frame having a plurality of openings;
   a plurality of thermally conductive tiles, each of which is retained within said flexible frame in thermal contact with a user side of one of said plurality of thermoelectric coolers (TECs) with said module configured to be operatively positionable with the tile in heat transfer relation with skin of a patient;
   wherein each of said plurality of thermoelectric coolers (TECs) is configured for being sandwiched between one of said plurality of thermally conductive plates and one of said plurality of thermally conductive tiles;
   wherein each of said plurality of thermally conductive plates and each of said plurality of thermally conductive tiles are configured with a snap-fit mechanism in which at least a first hook on one of said plurality of thermally conductive plates is configured for snap-fit engagement with at least a second hook on said plurality of thermal tiles;
   a plurality of temperature sensors, each said temperature sensor in thermal communication with each of said plurality of thermally conductive tiles for detecting temperature of the skin of the patient;
   wherein said liquid chamber box comprises a first and second sheet of thermoplastic material that are formed and adhered together forming a heat-transfer fluid channel therebetween, and in which said second sheet of thermoplastic material is configured with one or more openings, wherein each of said plurality of conductive plates is received by and seals over a respective opening of said one or more openings in said second sheet of thermoplastic material; and
   wherein each of said plurality of thermally conductive plates is positioned to be in direct contact with heat transfer fluid flowing through said heat transfer fluid channel.

8. The assembly of claim 7,
   wherein each of said thermally conductive plates comprise fins, nubs or extrusions extending up from each of said plurality of thermally conductive plates into said liquid chamber box to prevent the heat-transfer fluid channel from collapsing when said liquid chamber box is flexed and providing additional heat transfer surface area between the fluid in said heat-transfer fluid channel and each of said plurality of thermally conductive plates.

9. The assembly of claim 7, further comprising a third sheet of thermoplastic material attached to said first and second sheets of thermoplastic material and formed to attach to a distal portion of each of said plurality of thermally conductive plates.

10. The assembly of claim 7, further comprising an air bladder proximal said liquid chamber box and configured for being pressurized and deflated to increase user comfort and improved thermal contact between said heat exchange module and the skin of the patient.

11. The assembly of claim 7, wherein each of said at least one thermally conductive plate is configured with perimeter slots into which said second and third sheets of thermoplastic material are heat pressed or RF welded to create a bond through the slot.

\* \* \* \* \*